(12) United States Patent
Pidaparthi et al.

(10) Patent No.: US 8,247,180 B2
(45) Date of Patent: *Aug. 21, 2012

(54) MEASURING RECEPTOR HOMODIMERIZATION

(75) Inventors: Sailaja Pidaparthi, Cupertino, CA (US); Yining Shi, San Jose, CA (US); Rajiv Dua, Manteca, CA (US); Po-Ying Chan-Hui, Oakland, CA (US); Sharat Singh, Los Altos, CA (US)

(73) Assignee: Monogram Biosciences, Inc., S. San Francisco, CA (US)

( * ) Notice: Subject to any disclaimer, the term of this patent is extended or adjusted under 35 U.S.C. 154(b) by 285 days.

This patent is subject to a terminal disclaimer.

(21) Appl. No.: 12/176,245

(22) Filed: Jul. 18, 2008

(65) Prior Publication Data

US 2009/0155818 A1 Jun. 18, 2009

Related U.S. Application Data

(60) Division of application No. 10/946,816, filed on Sep. 22, 2004, now Pat. No. 7,402,398, which is a continuation-in-part of application No. 10/623,057, filed on Jul. 17, 2003, now Pat. No. 7,105,308.

(60) Provisional application No. 60/508,034, filed on Oct. 1, 2003, provisional application No. 60/566,352, filed on Apr. 28, 2004, provisional application No. 60/577,256, filed on Jun. 3, 2004.

(51) Int. Cl.
*G01N 33/53* (2006.01)
*G01N 33/532* (2006.01)
*G01N 33/554* (2006.01)
*C07K 1/10* (2006.01)
*C07K 1/14* (2006.01)

(52) U.S. Cl. ......... 435/7.1; 436/544; 436/161; 436/824; 530/402; 530/412; 530/389.8

(58) Field of Classification Search ........................ None
See application file for complete search history.

(56) References Cited

U.S. PATENT DOCUMENTS 2,153,059 A    4/1939 Eckert et al.
(Continued)

FOREIGN PATENT DOCUMENTS

AU    2001279222    8/2001
(Continued)

OTHER PUBLICATIONS

Autiero et al., "Role of PlGF in the Intra- and Intermolecular Cross Talk Between VEGF Receptors Flt1 and Flk1," Nature Medicine, Jun. 8, 2003, pp. 936-943, vol. 9.

(Continued)

*Primary Examiner* — Shafiqul Haq
(74) *Attorney, Agent, or Firm* — Kilpatrick Townsend & Stockton LLP

(57) ABSTRACT

The invention provides methods and kits for detecting and/or measuring receptor homodimers on a cell surface membrane. In one aspect, the methods employ pairs of probes comprising binding compounds and a cleaving probe, such that at least one binding compound binds specifically to the same epitope of a membrane-bound analyte as the cleaving probe. The binding compound includes one or more molecular tags attached through a cleavable linkage, and the cleaving probe includes a cleavage-inducing moiety that can cleave the linkage when within a defined proximity thereto. Binding of the two probes to a homodimer of a cell surface molecules results in release of molecular tags from the binding compounds, providing a measure of formation of the homodimeric complex.

14 Claims, 26 Drawing Sheets

U.S. PATENT DOCUMENTS

| | | | |
|---|---|---|---|
| 2,242,572 A | 5/1941 | Eckert et al. | |
| 3,932,415 A | 1/1976 | Reynolds | |
| 4,230,558 A | 10/1980 | Fulwyler | |
| 4,274,240 A | 6/1981 | Soum | |
| 4,318,846 A | 3/1982 | Khanna et al. | |
| 4,375,407 A | 3/1983 | Kronick | |
| 4,452,773 A | 6/1984 | Molday | |
| 4,650,750 A | 3/1987 | Giese | |
| 4,675,300 A | 6/1987 | Zare et al. | |
| 4,795,698 A | 1/1989 | Owen et al. | |
| 4,811,218 A | 3/1989 | Hunkapiller et al. | |
| 4,879,012 A | 11/1989 | Kambara et al. | |
| 4,997,928 A | 3/1991 | Hobbs, Jr. | |
| 5,091,652 A | 2/1992 | Mathies et al. | |
| 5,274,240 A | 12/1993 | Mathies et al. | |
| 5,288,514 A | 2/1994 | Ellman | |
| 5,324,401 A | 6/1994 | Yeung et al. | |
| 5,340,716 A | 8/1994 | Ullman et al. | |
| 5,360,819 A | 11/1994 | Giese | |
| 5,374,527 A | 12/1994 | Grossman | |
| 5,480,968 A | 1/1996 | Kraus et al. | |
| 5,508,164 A | 4/1996 | Kausch et al. | |
| 5,516,636 A | 5/1996 | McCapra | |
| 5,516,931 A | 5/1996 | Giese et al. | |
| 5,536,834 A | 7/1996 | Singh et al. | |
| 5,543,026 A | 8/1996 | Hoff et al. | |
| 5,552,028 A | 9/1996 | Madabhushi et al. | |
| 5,560,811 A | 10/1996 | Briggs et al. | |
| 5,565,324 A | 10/1996 | Still et al. | |
| 5,565,552 A | 10/1996 | Magda et al. | |
| 5,597,531 A | 1/1997 | Liberti et al. | |
| 5,599,681 A | 2/1997 | Epstein et al. | |
| 5,602,273 A | 2/1997 | Giese et al. | |
| 5,622,929 A | 4/1997 | Willner et al. | |
| 5,624,800 A | 4/1997 | Grossman et al. | |
| 5,646,001 A | 7/1997 | Terstappen et al. | |
| 5,665,582 A | 9/1997 | Kausch et al. | |
| 5,677,171 A | 10/1997 | Hudziak et al. | |
| 5,691,208 A | 11/1997 | Miltenyi et al. | |
| 5,698,271 A | 12/1997 | Liberti et al. | |
| 5,709,994 A | 1/1998 | Pease et al. | |
| 5,750,015 A | 5/1998 | Soane et al. | |
| 5,756,726 A | 5/1998 | Hemmi et al. | |
| 5,763,602 A | 6/1998 | Li et al. | |
| 5,772,997 A | 6/1998 | Hudziak et al. | |
| 5,811,098 A | 9/1998 | Plowman et al. | |
| 5,856,107 A | 1/1999 | Ostresh et al. | |
| 5,900,130 A | 5/1999 | Benvegnu et al. | |
| 5,945,526 A | 8/1999 | Lee et al. | |
| 5,968,511 A | 10/1999 | Akita et al. | |
| 5,986,076 A | 11/1999 | Rothschild et al. | |
| 5,998,224 A | 12/1999 | Rohr et al. | |
| 6,001,673 A | 12/1999 | Marcinkiewicz | |
| 6,007,690 A | 12/1999 | Nelson et al. | |
| 6,045,676 A | 4/2000 | Mathies et al. | |
| 6,048,515 A | 4/2000 | Kreese et al. | |
| 6,096,723 A | 8/2000 | Menchen et al. | |
| 6,142,162 A | 11/2000 | Arnold | |
| 6,191,278 B1 | 2/2001 | Lee et al. | |
| 6,245,937 B1 | 6/2001 | Cheng et al. | |
| 6,251,581 B1 | 6/2001 | Ullman et al. | |
| 6,322,980 B1 | 11/2001 | Singh | |
| 6,346,384 B1 | 2/2002 | Pollner | |
| 6,365,362 B1 | 4/2002 | Terstappen et al. | |
| 6,372,907 B1 | 4/2002 | Lee et al. | |
| 6,488,390 B1 | 12/2002 | Lebens et al. | |
| 6,514,700 B1 | 2/2003 | Singh | |
| 6,547,654 B2 | 4/2003 | Del Raso | |
| 6,627,400 B1 | 9/2003 | Singh et al. | |
| 6,630,296 B2 | 10/2003 | Xue et al. | |
| 6,649,351 B2 | 11/2003 | Matray et al. | |
| 6,673,550 B2 | 1/2004 | Matray et al. | |
| 6,682,877 B2 | 1/2004 | Singh | |
| 6,686,152 B2 | 2/2004 | Singh et al. | |
| 6,770,439 B2 | 8/2004 | Singh et al. | |
| 6,818,399 B2 | 11/2004 | Singh et al. | |
| 6,846,645 B2 | 1/2005 | Xue et al. | |
| 6,916,612 B2 | 7/2005 | Singh et al. | |
| 6,949,347 B2 | 9/2005 | Singh et al. | |
| 6,955,874 B2 | 10/2005 | Singh et al. | |
| 7,001,725 B2 | 2/2006 | Singh et al. | |
| 7,037,654 B2 | 5/2006 | Chenna et al. | |
| 7,041,459 B2 | 5/2006 | Singh et al. | |
| 7,045,311 B2 | 5/2006 | Ciambrone et al. | |
| 7,105,308 B2 | 9/2006 | Chan-Hui et al. | |
| 7,135,300 B2 | 11/2006 | Chan Hui et al. | |
| 7,160,735 B2 | 1/2007 | Dehlinger et al. | |
| 7,217,531 B2 | 5/2007 | Singh et al. | |
| 7,255,999 B2 | 8/2007 | Singh et al. | |
| 7,279,585 B2 | 10/2007 | Singh et al. | |
| 7,312,034 B2 | 12/2007 | Virgos et al. | |
| 7,358,052 B2 | 4/2008 | Singh | |
| 7,402,397 B2 * | 7/2008 | Chan-Hui et al. ............. 435/7.1 |
| 7,402,398 B2 * | 7/2008 | Pidaparthi et al. ............. 435/7.1 |
| 7,402,399 B2 | 7/2008 | Mukherjeei et al. | |
| 7,537,938 B2 | 5/2009 | Kirakossian et al. | |
| 7,648,828 B2 * | 1/2010 | Chan-Hui et al. ............ 435/7.23 |
| 7,771,929 B2 | 8/2010 | Singh et al. | |
| 2002/0045738 A1 | 4/2002 | Singh et al. | |
| 2002/0058263 A1 | 5/2002 | Singh et al. | |
| 2003/0092012 A1 | 5/2003 | Chenna et al. | |
| 2003/0170734 A1 | 9/2003 | Williams et al. | |
| 2003/0175747 A1 | 9/2003 | Singh | |
| 2003/0203408 A1 | 10/2003 | Williams et al. | |
| 2003/0207300 A1 | 11/2003 | Matray et al. | |
| 2003/0235832 A1 | 12/2003 | Chenna et al. | |
| 2004/0029139 A1 | 2/2004 | Singh | |
| 2004/0067498 A1 | 4/2004 | Chenna et al. | |
| 2004/0091850 A1 | 5/2004 | Boone et al. | |
| 2004/0106161 A1 | 6/2004 | Bossenmaier et al. | |
| 2004/0166529 A1 | 8/2004 | Singh et al. | |
| 2004/0175765 A1 | 9/2004 | Singh et al. | |
| 2004/0197815 A1 | 10/2004 | Singh et al. | |
| 2004/0229293 A1 | 11/2004 | Chan-Hui et al. | |
| 2004/0229294 A1 | 11/2004 | Chan-Hui et al. | |
| 2004/0229299 A1 | 11/2004 | Badal et al. | |
| 2004/0229380 A1 | 11/2004 | Chan-Hui et al. | |
| 2004/0248150 A1 | 12/2004 | Singh et al. | |
| 2004/0265858 A1 | 12/2004 | Singh et al. | |
| 2005/0048553 A1 | 3/2005 | Chenna et al. | |
| 2005/0079565 A1 | 4/2005 | Chan-Hui et al. | |
| 2005/0130238 A1 | 6/2005 | Chan-Hui et al. | |
| 2005/0130246 A1 | 6/2005 | Salimi-Moosavi et al. | |
| 2005/0170438 A1 | 8/2005 | Chan-Hui et al. | |
| 2006/0199231 A1 | 9/2006 | Moore et al. | |
| 2006/0223107 A1 | 10/2006 | Chenna et al. | |
| 2008/0187948 A1 | 8/2008 | Chan-Hui et al. | |
| 2008/0233602 A1 * | 9/2008 | Chan-Yui et al. ................ 435/15 |
| 2008/0254497 A1 | 10/2008 | Singh | |
| 2008/0311674 A1 | 12/2008 | Singh et al. | |
| 2009/0011432 A1 * | 1/2009 | Chan-Hui et al. ............. 435/7.4 |
| 2009/0011440 A1 | 1/2009 | Mukherjee et al. | |
| 2009/0111127 A1 | 4/2009 | Chan-Hui et al. | |
| 2009/0155818 A1 | 6/2009 | Pidaparthi et al. | |
| 2009/0173631 A1 | 7/2009 | Boone et al. | |
| 2009/0191559 A1 | 7/2009 | Huang et al. | |
| 2010/0143927 A1 | 6/2010 | Sperinde et al. | |
| 2010/0210034 A1 | 8/2010 | Bates et al. | |
| 2010/0233732 A1 | 9/2010 | Bates et al. | |
| 2010/0291594 A1 | 11/2010 | Chan-Hui et al. | |
| 2011/0180408 A1 | 7/2011 | Badal et al. | |

FOREIGN PATENT DOCUMENTS

| | | |
|---|---|---|
| CA | 2403326 | 11/2001 |
| EP | 0510688 | 10/1992 |
| EP | 0484027 | 12/1996 |
| EP | 1278760 | 6/2008 |
| EP | 1540347 | 9/2009 |
| WO | WO 91/19735 | 12/1991 |
| WO | WO 92/00091 | 1/1992 |
| WO | WO 93/20242 | 10/1993 |
| WO | WO 98/45693 | 10/1998 |
| WO | WO 99/15876 | 4/1999 |
| WO | WO 99/19717 | 4/1999 |
| WO | WO 00/66607 | 11/2000 |
| WO | WO 01/83502 | 11/2001 |
| WO | WO 01/84157 | 11/2001 |

| | | |
|---|---|---|
| WO | WO 02/12547 | 2/2002 |
| WO | WO 02/30944 | 4/2002 |
| WO | WO 02/094998 | 11/2002 |
| WO | WO 02/095356 | 11/2002 |
| WO | WO 03/006947 | 1/2003 |
| WO | WO 03/032867 | 4/2003 |
| WO | WO 03/033741 | 4/2003 |
| WO | WO 03/042398 | 5/2003 |
| WO | WO 03/042657 | 5/2003 |
| WO | WO 03/042658 | 5/2003 |
| WO | WO 03/042699 | 5/2003 |
| WO | WO 03/051669 | 6/2003 |
| WO | WO 03/076649 | 9/2003 |
| WO | WO 03/076649 A1 | 9/2003 |
| WO | WO 03/085374 | 10/2003 |
| WO | WO 2004/010842 | 2/2004 |
| WO | WO 2004/011900 | 2/2004 |
| WO | WO 2004/061131 | 7/2004 |
| WO | WO 2004/061446 | 7/2004 |
| WO | WO 2004/063700 | 7/2004 |
| WO | WO 2004/068116 | 8/2004 |
| WO | WO 2004/087887 | 10/2004 |
| WO | WO 2004/091384 | 10/2004 |
| WO | WO 2004/092353 | 10/2004 |
| WO | WO 2005/019470 | 3/2005 |
| WO | WO 2005/037071 | 4/2005 |
| WO | WO 2005/045058 | 5/2005 |
| WO | WO 2005/072507 | 8/2005 |
| WO | WO 2006/044748 | 4/2006 |
| WO | WO 2006/052788 | 5/2006 |
| WO | WO 2006/084018 | 8/2006 |
| WO | WO 2009/070772 | 6/2009 |
| WO | WO 2009/086197 | 7/2009 |
| WO | WO 2010/065568 | 6/2010 |
| WO | WO 2010/083463 | 7/2010 |
| WO | WO 2010/083470 | 7/2010 |

OTHER PUBLICATIONS

Burmer, G.C. et al., Frequency and Spectrum of c-Ki-*ras* Mutations in Human Sporadic Colon Carcinoma, Carinomas Arising in Ulcerative Colitis, and Pancreatic Adenocarcinoma, Environmental Health Perspectives, 1991, pp. 27-31, vol. 93.
Buskens, C. et al., "Adenocarcinomas of the Gastro-Esophageal Junction: A Comparative Study of the Gastric Cardia and the Esophagus with Respect to Cycloxygenase-2 Expression," Digestive Disease Week Abstracts and Itinerary Planner, 2003, Abstract No. 850.
Drexler, H.G., "Recent Results on the Biology of Hodgkin and Reed-Sternberg Cells, II. Continuous Cell Lines," Leukemia and Lymphoma, 1993, pp. 1-25, vol. 9.
Embleton, M.J. et al., "Monoclonal Antibodies to Osteogenic Sacroma Antigens," Immunol. Ser., 1984, pp. 181-207, vol. 23.
European Examination Report, European Application EP 03771670.1, Dec. 14, 2007, 4 pages.
European Examination Report, European Application EP 03771670.1, Mar. 8, 2007, 6 pages.
European Search Report, European Application EP 03771670.1, Jul. 18, 2006, 2 pages.
Hsu, T.C., "Karyology of Cells in Culture," Tissue Culture Methods and Applications, Kruse and Patterson, Eds., Academic Press, N.Y., 1973, p. 764.
Hudelist, G. et al., "Co-expression of ErbB-family Members in Human Breast Cancer: Her-2/neu is the Preferred Dimerization Candidate in Notal-Positive Tumors," Breast Cancer Research and Treatment, 2003, pp. 353-361, vol. 80, Kluwer Academic Publishers, Netherlands.
Kunkel, P. et al., "Expression and Localization of Scatter Factor/Hepatocyte Growth Factor in Human Astrocytomas," Neuro-Oncology, Apr. 2001, pp. 82-88, vol. 3, No. 2.
Lundy, J. et al., "Expression of *neu* Protein, Epidermal Growth Factor Receptor, and Transforming Growth Factor Alpha in Breast Cancer," American Journal of Pathology, Jun. 1991, vol. 138, No. 6.
Montesano, R. et al., "Genetic Alterations in Esophageal Cancer and Their Relevance to Etiology and Pathogenesis: A Review," Intl. J. Cancer, 1996, pp. 225-235, vol. 69, No. 3.
Rios, C.D. et al., "G-Protein-Coupled Receptor Dimerization: Modulation of Receptor Function," Pharmacology and Therapeutics, Nov. 2001, pp. 71-87, vol. 92, No. 2/3.
Slamon, D.J. et al., "Human Breast Cancer: Correlation of Relapse and Survival with Amplification of the HER-2/*neu* Oncogene," Science, Jan. 9, 1987, pp. 177-182, vol. 235.
Tian, J. et al., "The Expression of Native and Cultured RPE Grown on Difference Matrices," Physiol. Genomics, Feb. 24, 2004, pp. 170-182, vol. 17.
Tockman, M.S. et al., "Considerations in Bringing a Cancer Biomarker to Clinical Application," Cancer Research, May 1, 1992, pp. 2711s-2718s, vol. 52.
Van Dyke, D. et al., "Monosomy 21 in Hematologic Diseases," Cancer Genetics and Cytogenetics, 2003, pp. 137-141, vol. 241.
Whitaker, G.B. et al., "Vascular Endothelial Growth Factor Receptor-2 and Neuropilin-1 Form a Receptor Complex That is Responsible for the Differential Signaling Potency of $VEGF_{165}$ and $VEGF_{121}$," The Journal of Biological Chemistry, Jul. 6, 2001, pp. 25520-25531, vol. 276.
Wildi, S. et al., "Overexpression of Activin A in Stage IV Colorectal Cancer," Gut Online, Sep. 2001, pp. 409-471, vol. 49.
Yakes, F.M. et al., "Herceptin-Induced Inhibition of Phosphatidylinositol-3 Kinase and Akt is Required for Antibody-mediated Effects on p27, Cyclin D1, and Antitumor Action," Cancer Research, Jul. 15, 2002, pp. 4132-4141, vol. 62.
Yarden, Y., "Biology of HER2 and its Importance in Breast Cancer," Oncology, 2001, pp. 1-13, vol. 61, Suppl. 2.
Zaslav, A.L. et al., "Significance of a Prenatally Diagnosed del(10)(q23)," American Journal of Medical Genetics, 2002, pp. 174-176, vol. 107.
Adam, W. and Liu, J., "Photooxygenation (Singlet Oxygen) of Tetrathioethylenes," 1972, J. Am. Chem. Soc., 94: 1206-1209.
Adam, W. et al., "Photooxygenation of Vinyl Sulfides: Substituent Effects on the [2+2] Cycloaddition versus Schenck Ene Reaction Modes," Tetrahedron Letters, 1995, 36:7853-7854.
Angers, S. et al., "Detection of $\beta_2$-adrenergic receptor dimerization in living cells using bioluminescence resonance energy transfer (BRET)," 2000, Proc. Natl. Acad. Sci. USA, 97:3684-3689.
Antibodies: A Laboratory Manual, Harlow, E. and Lane, D. eds., Cold Spring Harbor Laboratory Press; New York 1988.
Ando, W. et al., "Photosensitized Oxygenation of Vinylic Sulphides," J. Chem. Soc. Chem. Comm., 1972, pp. 477-478.
Ando, W. et al., "Singlet Oxygen Reaction. III. 'Solvent and Temperature Effects' on the Photosensitized Oxygenation of Vinyl Sulfides and Vinyl Ethers," J. Am. Chem. Soc., 1974, 96:6766-6768.
Ando, W. et al., "Singlet Oxygen Reaction. IV. Photooxygenation of Enamines Involving a Two-Step Cleavage of a 1,2-Dioxetane Intermediate," J. Am. Chem. Soc., 1975, 97:5028-5029.
Ando, W. et al., "Singlet Oxygen Reaction V. Ring Size Effects on the Decomposition of Sulfur Substituted 1,2-Dioxetane," Tetrahedron Lett., 1975, 47:4127-4130.
Ando, W. et al., "Singlet oxygen reaction—II: Alkylthiosubstituted ethylene," Tetrahedron, 1973, 29(11): 15071513.
Bangham, A. et al., "Diffusion of Univalent Ions Across the Lamellae of Swollen Phospholipids," J. Mol. Biol., 1965, 13:238-252.
Basic Methods in Antibody Production and Characterization, Howard, C. and Bethell, D. eds., CRC Press, 2001.
Guide to Molecular Cloning Techniques, Berger, S. and Kimmel, A. eds., Methods in Enzymology, vol. 152, Academiic Press, New York, 1987.
Beutner, S. et al., "Synthetic Singlet Oxygen Quenchers," Methods Enzymol., Packer, L. and Sies, H., eds., 2000, 319:226-241.
Bioconjugate Techniques, Hermanson, G., ed., Academic Press, New York, 1996.
Blume-Jensen, P. and Hunter, T., "Oncogenic kinase signalling," Nature, 2001, 411:355-365.
Burlingame, A. et al., "Mass Spectrometry," Anal. Chem., 1998, 70:647R-716R.
Cambpell, D. and Bermak, J., "Phosphonate Ester Synthesis Using a Modified Mitsunobu Condensation," J. Org. Chem., 1994, 59:658-660.

Chen, C. et al., "'Analogous' Organic Synthesis of Small-Compound Libraries: Validation of Combinatorial Chemistry in Small-Molecule Synthesis," J. Am. Chem. Soc., 1994, 116:2661-2662.

Cho, C. et al., "An Unnatural Biopolymer," Science, 1993, 261:1303-1305.

Column Handbook for Size Exclusion Chromatography, 1999, Wu, C., ed., Academic Press, San Diego, CA.

Cuatrecasas, P., "Protein Purification by Affinity Chromatography. Derivatizations of Agarose and Polyacrylamide Beads," J. Biol. Chem., 1970, 245:3059-3065.

Demas, J. and DeGRAFF, B.A., "Interactions of Transition-Metal-Complex Photosensitizers with Polymers and Organized Media," J. Macromol. Sci.-Chem., 1988, A25:1189-1214.

Di Mascio, P. et al., "Singlet Molecular Oxygen Production in the Reaction of Peroxynitrite with Hydrogen Peroxide," FEBS Letters, 1994, 355:287-289.

Gel Electrophoresis of Proteins: A Practical Approach, Hames B. and Rickwood, D. eds., 1981, IRL Press, Oxford.

George, S. et al., "G-Protein-Coupled Receptor oligomerization and its Potential for Drug Discovery," 2002, Nature Reviews Drug Discovery, 1:808-820.

Ghossein, R. and Bhattacharya, S., "Molecular Detection and Characterization of Circulating Tumor Cells and Micrometastases in Prostatic, Urothelial, and Renal Cell Carcinomas," Semin. Surg. Oncol., 2001, 20:304-311.

Gordon, E. et al., "Applications of Combinatorial Technologies to Drug Discovery. 2. Combinatorial Organic Synthesis, Library Screening Strategies, and Future Directions," J. Med. Chem., 1994, 37:1385-1401.

Capillary Electrophoresis: Theory and Practice, Grossman, P. and Colburn, J., eds., Academic Press, New York, 1992.

Haber, P. et al., "Computer Simulation for the Simultaneous Optimization of Any Two Variables and Any Chromatographic Procedure," J. Chromatogr. Sci., 2000, 38:386-392.

Hagihara, M. et al., "Vinylogous Polypeptides: An Alternative Peptide Backbone," J. Am. Chem. Soc., 1992,114:6568-6570.

Haugland, R., Handbook of Fluorescent Probes and Research Products, Ninth Edition, Molecular Probes, Eugene, OR, 2002.

Heizmann, G. and Eberle, A., "Xanthines as a Scaffold for Molecular Diversity," Mol. Divers., 1996, 2:171-174.

Herbst, R. and Shin, D., "Monoclonal Antibodies to Target Epidermal Growth Factor Receptor-Positive Tumors: A New Paradigm for Cancer Therapy," Cancer, 2002, 94:1593-1611.

Hirschmann, R. et al., "Nonpeptidal Peptidomimetics with a β-D-Glucose Scaffolding. A Partial Somatostatin Agonist Bearing a Close Structural Relationship to a Potent, Selective Substance P Antagonist," 1992, J. Am. Chem. Soc., 114:9217-9218.

Hobbs Dewitt, S. et al., "'Diversomers': An Approach to Nonpeptide, Nonoligomeric Chemical Diversity," Proc. Nat. Sci. USA, 1993, 90:6909-6913.

PCR Protocols: A Guide to Methods and Applications, Innis. M. et al. eds., Academic Press, NY, 1990.

Schaap, A. et al., "Polymer-Based Sensitizers for Photooxidations. II," J. Amer. Chem. Soc., 1975, 97:3741-3745.

Jones, K. et al., "GABA$_B$ Receptors Function as a Heteromeric Assembly of the Subunits GABA$_B$R1 and GABA$_B$R2," Nature, 1998, 396:674-679.

Kanofsky, J., "Singlet Oxygen Production by Lactoperoxidase: Evidence from 1270 nm Chemiluminescence," 1983, J. Biol. Chem., 258:5991-5993.

Kaupmann, K. et al., "GABA$_B$Receptor Subtypes Assemble Into Functional Heteromeric Complexes," Nature, 1998, 396:683-687.

High Resolution Chromatography: A Practical Approach, 1999, Millner, P., ed., Oxford University Press, New York.

HPLC of Macromolecules: A Practical Approach, Oliver, R., ed., Oxford University Press, Oxford, England, 1989.

Immobilized Enzymes: Research and Development, Chibata, I., ed., Halsted Press, John Wiley & Sons, New York, 1978.

Krylov, S. and Dovichi, N., "Capillary Electrophoresis for the Analysis of Biopolymers," Anal. Chem., 2000, 72:111R-128R.

Lee, L. et al., "New Energy Transfer Dyes for DNA Sequencing," Nucleic Acids Res., 1997, 25:2816-2822.

Lewis, J.A., et al., "Computer Simulation for the Prediction of Separation as a Function of pH for Reversed-Phase High-Performance Liquid Chromatography. I. Accuracy of a Theory-Based Model," 1992, J. Chromatogr., 592:183-95.

Lewis, J.A., et al., "Computer Simulation for the Prediction of Separation as a Function of pH for Reversed-Phase High-Performance Liquid Chromatography. II. Resolution as a Function of Simultaneous Change in pH and Solvent Strength," 1992, J. Chromatogr., 592:197-208.

Madison, R., et al., "Latex Nanosphere Delivery System (LNDS): Novel Nanometer-Sized Carriers of Fluorescent Dyes and Active Agents Selectively Target Neuronal Subpopulations Via Uptake and Retrograde Transport," Brain Research, 1990, 522:90-98.

Manual of Histologic Staining Methods of the Armed Forces Institute of Pathology, Third Edition, Luna, L., ed., McGraw-Hill Book Company, New York, 1960.

Martin, J. and Burch, P., "Production of Oxygen Radicals by Photosensitization," 1990, Methods Enzymol., Packer, L. and Glazer, A., eds., 186:635-645.

McVey, M. et al., "Monitoring Receptor Oligomerization Using Time-resolved Fluorescence Resonance Energy Transfer and Bioluminescence Resonance Energy Transfer," 2001, J. Biol. Chem., 276:14092-14099.

Mellado, M. et al., "Chemokine Signaling and Functional Responses: The Role of Receptor Dimerization and TK Pathway Activation," 2001, Annu. Rev. Immunol., 19:397-421.

Milligan, G. and White, J., "Protein-Protein Interactions at G-Protein-Coupled Receptors," Trends Pharmacological Sciences, 2001, 22(10):513-518.

Miltenyi, S. et al., "High Gradient Magnetic Cell Separation With MACS," 1990, Cytometry, 11:231-238.

Moreno, J. et al., "Changes in Circulating Carcinoma Cells in Patients with Metastatic Prostate Cancer Correlate with Disease Status," 2001, Urology, 58:386-392.

Modern Molecular Photochemistry, Turro, N., ed., University Science Books, Mill Valley, CA, USA, 1991.

Nakamura, M. et al., "Separation of a Breast Cancer Cell Line from Human Blood Using a Quadrupole Magnetic Flow Sorter," 2001, Biotechnol. Prog., 17:1145-1155.

Outinen, K. et al., "Optimization of Selectivity in High-Performance Liquid Chromatography Using Desirability Functions and Mixture Designs According to PRISMA," 1998, Eur. J. Pharm. Sci., 6:197-205.

Papahadjopoulos, D. and Miller, N. "Phospholipid Model Membranes. I. Structural Characteristics of Hydrated Liquid Crystals." Biochim. Biophys. Acta., 1967,135:624-638.

Pavia, M,. et al., "The Design and Synthesis of Substituted Biphenyl Libraries," 1996, Bioorg. Med. Chem., 4:659-666.

Pearse, A., Histochemistry: Theoretical and Applied, vol. 1, Preparative and Optical Technology, 4$^{th}$ Ed., 1980, Churchill Livingstone, Edinburgh.

Pierlot, C. et al., "Naphthalene Endoperoxides as Generators of Singlet Oxygen in Biological Media," 2000, Methods Enzymol., 319:3-20.

Polo, E. et al., "Entrapping of Iron(III) Porphyrins in a Polystyrene Matrix and Their Photocatalytic Activity in Oxidation Reactions by Molecular Oxygen," Inorganica Chimica Acta, 1992, 192:1-3.

Practical HPLC Method Development, Snyder, L. et al., eds., John Wiley and Sons, New York, 1998.

Price, D. et al., "Methods for the Study of Protein-Protein Interactions in Cancer Cell Biology," Methods Mol. Biol., D. Terrian, ed., 2003, 218:255-267.

Protective Groups in Organic Synthesis, 3$^{th}$ ed., Greene, T. and Wuts, P. eds., John Wiley & Sons, New York, 1999.

Protein Sequencing and Identification Using Tandem Mass Spectrometry, M. Kinter and N. Sherman, eds., Wiley Interscience, New York, 2000.

Proteome Research: Two-Dimensional Gel Electrophoresis and Identification Methods, Rabilloud, T., Springer-Verlag, Berlin, 2000.

Racila, E. et al., "Detection and Characterization of Carcinoma Cells in the Blood," Proc. Natl. Acad. Sci. USA, 1998, 95:4589-4594.

Radbruch, A. et al., "High-Gradient Magnetic Cell Sorting," Methods in Cell Biology, Ch. 23, 1994, Darzynkiewicz, Z. et al., eds., 42:387-403.

Safarik, L. and Safarikova, M., "Use of Magnetic Techniques for the Isolation of Cells," J. Chromatogr. B., 1999, 722:33-53.

Salim, K. et al., "Oligomerization of G-protein-coupled Receptors Shown by Selective Co-immunoprecipitation," 2002, J. Biol. Chem., 277:15482-15485.

Molecular Cloning: A Laboratory Manual, Sambrook, J. and Russell, D. eds., Cold Spring Harbor Laboratory, 3rd ed., NY, 2001.

Schlessinger, J., "Cell Signaling by Receptor Tyrosine Kinases," Cell, 2000, 103:211-225.

Schlessinger, J., "Ligand-Induced, Receptor-Mediated Dimerization and Activation of EGF Receptor," 2002, Cell, 110:669-672.

Scopes, R., Protein Purification: Principles and Practice, Springer-Verlag, New York, 1982.

Sessler, J. et al., "Tripyrroledimethine-Derived ("Texaphyrin"-Type) Macrocycles: Potential Photosensitizers Which Absorb in the Far-Red Spectral Region," SPIE—Proceedings of Optical Methods for Tumor Treatment and Early Diagnosis: Mechanisms and Techniques, Dougherty, T., ed., 1991, 1426:318-329.

Singlet Oxygen, Wasserman, H. and Murray, R., eds., Academic Press, New York, 1979.

Baumstark, A., "The 1,2-Dioxetane Ring System: Preparation, Thermolysis, and Insertion Reactions," Singlet Oxygen, vol. 2, CRC Press Inc., Boca Raton, FL, 1983.

Smith, M. and March, J., March's Advanced Organic Chemistry: Reactions, Mechanisms, and Structure, $5^{th}$ Ed., Wiley-Interscience, NY, 2001.

Strong, L. et al., "Antibody-Targeted Photolysis: Photophysical, Biochemical, and Pharmacokinetic Properties of Antibacterial Conjugates," Ann. N.Y. Acad. Sci., 1994, 745:297-320.

Svec, F., "Capillary Electrochromatography: A Rapidly Emerging Separation Method," Adv. Biochem. Eng. Biotchnol., 2002, 76:1-47.

The Armed Forces Institute of Pathology Advanced Laboratory Methods in Histology and Pathology, Armed Forces Institute of Pathology, American Registry of Pathology, Mikel, U., ed., Washington, D.C., 1994.

Theory and Practice of Histological Techniques, Bancroft, J. and Stevens, A., eds., Churchill Livingston, New York, 1977.

The Immunoassay Handbook, Wild, D. ed., Stockton Press, New York, 1994.

Advances in Biomagnetic Separation, Uhlen, M. et al., eds., Eaton Publishing Company/Biotechniques Books, Natick, 1994.

Ullman, E. et al., "Luminescent oxygen channeling immunoassay: Measurement of particle binding kinetics by chemiluminescence," 1994, Proc. Natl. Acad. Sci. USA, 91:5426-5430.

Vanhoenacker, G. et al., "Recent Applications of Capillary Electrochromatography," Electrophoresis, 2001, 22:4064-4103.

White, T. et al., "Heterodimerization is Required for the Formation of a Functional $GABA_B$ Receptor," Nature, 1998, 396:679-682.

Wasserman, H. and Terao, S., "Enamine-Singlet Oxygen Reactions. α-Diketones From Intermediate Amino Dioxetanes," Tetrahedron Lett., 1975, 16:1735-1738.

Wheeless, L. and Kay, D., "Optics, Light Sources, Filters, and Optical Systems," Flow Cytometry: Instrumentation and Data Analysis, Van Dilla, M. et al., eds., Academic Press, New York, 1985, pp. 21-76.

Wohrle, D., "Porphyrins, Phthalocyanines, and Naphthalocyanines for Various Processes of Visible Light Driven Conversion Processes," Chimia, 1991, 45:307-310.

Wold, F., "Posttranslational Protein Modifications: Perspectives and Prospectives," Posttranslational Covalent Modifications of Proteins, Johnson, B., ed. Academic Press, New York, 1983, pp. 1-12.

Yarden, Y. and Sliwkowski, M., "Untangling the ErbB Signalling Network," Nat. Rev. Mol. Cell. Biol., 2001, 2:127-137.

Yarden, Y., "The EGFR Family and its Ligands in Human Cancer: Signalling Mechanisms and Therapeutic Opportunities," Eur. J. Cancer, 2001, 37:S3-S8.

Yarmush, L. et al., "Antibody Targeted Photolysis," Crit. Rev. Ther. Drug Carrier Syst., 1993, 10:197-252.

Zaklika, K. et al., "Mechanisms of 1,2-Dioxetane Decomposition: The Role of Electron Transfer," Photochemistry and Photobiology, 1979, 30:35-44.

Zhang, X. et al., "Synthesis of Releasable Electrophore Tags for Applications in Mass Spectrometry," Bioconjug. Chem., 2002, 13:1002-1012.

Zigeuner, R. et al., "Isolation of Circulating Cancer Cells From Whole Blood by Immunomagnetic Cell Enrichment and Unenriched Immunocytochemistry In Vitro," J. Urol., 2003, 169:701-705.

International Search Report mailed Apr. 8, 2004 corresponding to PCT application PCT/US2003/022611.

International Search Report and Written Opinion mailed Nov. 2, 2005 corresponding to PCT application PCT/US2004/009715.

International Search Report and Written Opinion mailed Apr. 25, 2005 corresponding to PCT application PCT/US2004/025945.

* cited by examiner

MEASURING RECEPTOR HOMODIMERIZATION

This patent application is a divisional of U.S. patent application Ser. No. 10/946,816, filed on 22 Sep. 2004, now U.S. Pat. No. 7,402,398, which is a continuation-in-part of U.S. patent application Ser. No. 10/623,057, filed 17 Jul. 2003, now U.S. Pat. No. 7,105,308, and claims priority from U.S. Provisional Application Ser. No. 60/508,034, filed 1 Oct. 2003; U.S. Provisional Application Ser. No. 60/566,352, filed 28 Apr. 2004; and U.S. Provisional Application Ser. No. 60/577,256, filed 3 Jun. 2004, all of which are incorporated herein by reference in their entireties, and from which priority is claims.

FIELD OF THE INVENTION

The present invention relates to methods for measuring oligomerization of cell surface molecules, particularly homodimers of cell surface membrane receptors.

BACKGROUND OF THE INVENTION

The interactions of cell surface membrane components play crucial roles in transmitting extracellular signals to a cell in normal physiology, and in disease conditions. In particular, many types of cell surface receptors undergo dimerization or oligomerization in connection with the transduction of an extracellular event or signal, e.g. ligand-receptor binding, into a cellular response, such as proliferation, increased or decreased gene expression, or the like, e.g. George et al, Nature Reviews Drug Discovery, 1: 808-820 (2002); Mellado et al, Ann. Rev. Immunol., 19: 397-421 (2001); Schlessinger, Cell, 103: 211-225 (2000); Yarden, Eur. J. Cancer, 37: S3-S8 (2001). The role of such signal transduction events in diseases, such as cancer, has been the object of intense research and has led to the development of several new drugs and drug candidates, e.g. Herbst and Shin, Cancer, 94: 1593-1611 (2002); Yarden and Sliwkowski, Nature Reviews Molecular Cell Biology, 2: 127-137 (2001).

A wide variety of techniques have been used to study dimerization and oligomerization of cell surface receptors, including immunoprecipitation, chemical cross-linking, bioluminescence resonance energy transfer (BRET), fluorescence resonance energy transfer (FRET), and the like, e.g. Price et al, Methods in Molecular Biology, 218: 255-267 (2003); McVey et al, J. Biol. Chem., 17: 14092-14099 (2001); Salim et al, J. Biol. Chem., 277: 15482-15485 (2002); Angers et al, Proc. Natl. Acad. Sci., 97: 3684-3689 (2000). Unfortunately, despite the importance of receptor dimerization and oligomerization in signal transduction processes, the techniques for measuring such interactions are difficult to apply, lack flexibility, and lack sensitivity. The lack of a convenient and sensitive technique for analyzing the oligomerization of cell surface molecules has greatly increased the difficulty of developing new therapeutics or diagnostic methods based on such phenomena.

In view of the above, the availability of a convenient, sensitive, and cost effective technique for detecting or measuring the dimerization or oligomerization of cell surface analytes would advance the art in many fields where such measurements are becoming increasingly important, including life science research, medical research and diagnostics, drug discovery, and the like.

SUMMARY OF THE INVENTION

The invention provides methods of detecting and/or measuring oligomers of membrane-bound molecules, and especially, homodimers and homo-oligomers of cell membrane receptors. In one aspect, the method of the invention uses at least two reagents that are specific for members of a dimer or oligomer: one member, referred to herein as a cleaving probe, has a cleavage-inducing moiety that may be induced to cleave susceptible bonds within its immediate proximity; and the other member, referred to herein as a binding compound, has one or more molecular tags attach by linkages that are cleavable by the cleavage-inducing moiety. In accordance with the method, whenever a homodimer or homo-oligomer forms, a fraction of such complexes, especially homodimers, will have specifically bound at least one cleaving probe and at least one binding compound. Under such conditions, the cleavable linkages of the binding compounds are brought within the effective cleaving proximity of the cleavage-inducing moieties so that molecular tags can be released. The released molecular tags are then separated from the reaction mixture and quantified to provide a measure of homodimerization or homo-oligomerization.

In another aspect, the method of the invention may comprising the following steps:
(a) providing a binding compound specific for a membrane-associated analyte forming a homodimer, the binding compound having one or more molecular tags each attached thereto by a cleavable linkage, the one or more molecular tags each having a separation characteristic;
(b) providing a cleaving probe specific for the membrane-associated analyte, the cleaving probe having a cleavage-inducing moiety with an effective proximity, and the cleaving probe and the binding compound being selected such that only one of either the cleaving probe or the binding composition can specifically bind to the same membrane-associated analyte at a time;
(c) combining the cleaving probe, the binding compound, and the cell membrane such that the cleaving probe and the binding compound specifically bind to membrane-associated analytes and such that cleavable linkages of the binding compound are within the effective proximity of the cleavage-inducing moiety whenever a homodimer is present and the cleaving probe and the binding compound specifically bind to different membrane-associated analytes thereof, so that molecular tags are released; and (d) separating and identifying the released molecular tags to determine the presence or absence or the amount of homodimer in the cell membrane.

In another aspect the method of the invention comprises the following steps:
(a) providing one or more binding compounds specific for different antigenic determinants of a homodimer, each binding compound having one or more molecular tags each attached thereto by a cleavable linkage, and the molecular tags of different binding compounds having different separation characteristics; (b) providing a cleaving probe specific for an antigenic determinant of the homodimer the same as at least one antigenic determinant that the one or more binding compounds are specific for, the cleaving probe having a cleavage-inducing moiety with an effective proximity; (c) mixing the cleaving probe, the one or more binding compounds, and the cell membrane such that the cleaving probe and the one or more binding compounds specifically bind to their respective antigenic determinants and the cleavable linkages of the one or more binding compounds are within the effective proximity of the cleavage-inducing moiety whenever a homodimer is present and the cleaving probe and at least one binding compound specifically bind to different antigenic determinants thereof, so that molecular tags are released; and (d) separating and identifying the released molecular tags to determine the presence or absence or the amount of homodimer in the cell membrane.

In another aspect, the invention includes kits for carrying out the methods of the invention. Such kits comprise at least one cleaving probe and one or more binding compounds having appropriate specificities for the homodimers to be detected or measured. In one embodiment, cleaving probes and at least one binding compound of the kit comprise the same antibody binding composition. In another embodiment, such kits are design for the detection of receptor tyrosine kinase homodimers. In another embodiment, such kits are designed for the detection of GPCR homodimers or EGFR homodimers.

In one aspect, the method of the invention uses at least two reagents that are specific for different members of a dimer or oligomer: one member, referred to herein as a cleaving probe, has a cleavage-inducing moiety that may be induced to cleave susceptible bonds within its immediate proximity; and the other member, referred to herein as a binding compound, has one or more molecular tags attach by linkages that are cleavable by the cleavage-inducing moiety. In accordance with the method, whenever such different members form a dimer or oligomer, the cleavable linkages are brought within the effective cleaving proximity of the cleavage-inducing moiety so that molecular tag can be released. The molecular tags are then separated from the reaction mixture and quantified to provide a measure of dimerization or oligomerization.

In another aspect, the method of the invention comprises the following steps: providing a cleaving probe specific for a first receptor type of a plurality of receptor types, the cleaving probe having a cleavage-inducing moiety with an effective proximity; providing one or more binding compounds each specific for a different second receptor type of the plurality, each binding compound having one or more molecular tags each attached thereto by a cleavable linkage, and the molecular tags of different binding compounds having different separation characteristics; mixing the cleaving probe, the one or more binding compounds, and a cell membrane containing the first and second receptor types such that the cleaving probe and the one or more binding compounds specifically bind to their respective receptors and the cleavable linkages of the one or more binding compounds are within the effective proximity of the cleavage-inducing moiety so that molecular tags are released; and separating and identifying the released molecular tags to determine the presence or absence or the amount of oligomerization of the receptor types in the cell membrane.

In another aspect, the invention provides a method of detecting dimers of membrane-associated analytes in a cell membrane, the method comprising the steps of: providing a binding compound specific for a first membrane-associated analyte of a dimer, the dimer comprising the first membrane-associated analyte and a second membrane-bound analyte, and the binding compound having one or more molecular tags each attached thereto by a cleavable linkage, the one or more molecular tags each having a separation characteristic; providing a cleaving probe specific for the second membrane-bound analyte, the cleaving probe having a cleavage-inducing moiety with an effective proximity; mixing the cleaving probe, the binding compound, and the cell membrane such that the cleaving probe specifically binds to the first membrane-associated analyte and the binding compound specifically binds to the second membrane-associated analyte and such that cleavable linkages of the binding compound are within the effective proximity of the cleavage-inducing moiety so that molecular tags are released; and separating and identifying the released molecular tags to determine the presence or absence or the amount of dimer in the cell membrane.

In another aspect, the invention provides a method for profiling the frequencies of dimers among a plurality of receptor types on the surfaces of cells.

The present invention provides a method of detecting or measuring the dimerization or oligomerization of membrane-associated analytes, especially homodimers thereof, that has several advantages over current techniques including, but not limited to, (1) the detection and/or measurement of molecular tags that are separated from an assay mixture provide greatly reduced background and a significant gain in sensitivity; and (2) the use of molecular tags that are specially designed for ease of separation and detection thereby providing convenient multiplexing capability.

DEFINITIONS

Figure 1A:
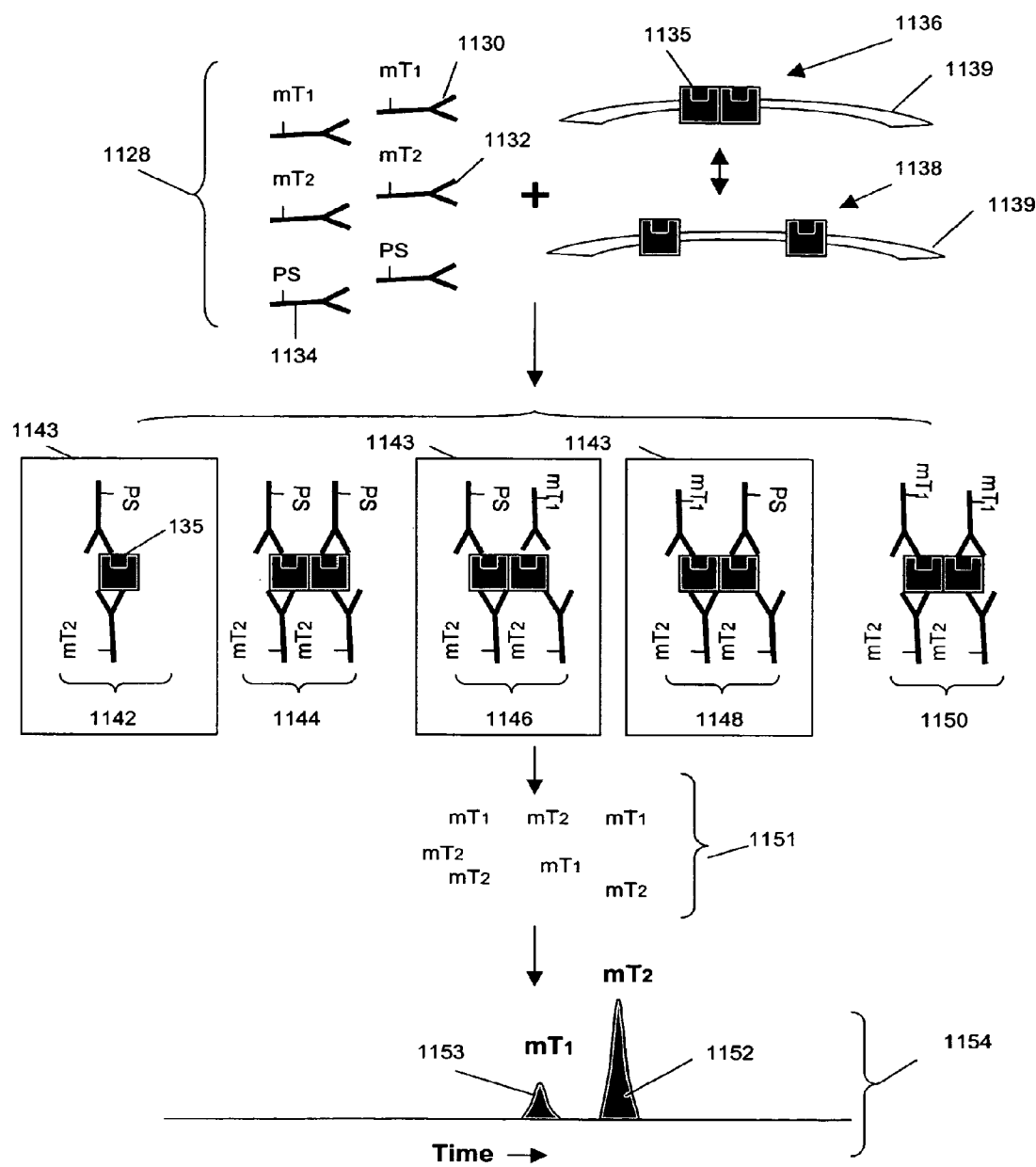
FIGS. 1A-1F illustrate diagrammatically the use of releasable molecular tags to measure receptor dimer populations.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained. Guidance in the production and selection of antibodies for use in immunoassays, including such assays employing releasable molecular tag (as described below) can be found in readily available texts and manuals, e.g. Harlow and Lane, Antibodies: A Laboratory Manual (Cold Spring Harbor Laboratory Press, New York, 1988); Howard and Bethell, Basic Methods in Antibody Production and Characterization (CRC Press, 2001); Wild, editor, The Immunoassay Handbook (Stockton Press, New York, 1994), and the like.

"Antibody binding composition" means a molecule or a complex of molecules that comprises one or more antibodies, or fragments thereof, and derives its binding specificity from such antibody or antibody fragment. Antibody binding compositions include, but are not limited to, (i) antibody pairs in which a first antibody binds specifically to a target molecule and a second antibody binds specifically to a constant region of the first antibody; a biotinylated antibody that binds specifically to a target molecule and a streptavidin protein, which protein is derivatized with moieties such as molecular tags or photosensitizers, or the like, via a biotin moiety; (ii) antibodies specific for a target molecule and conjugated to a polymer, such as dextran, which, in turn, is derivatized with moieties such as molecular tags or photosensitizers, either directly by covalent bonds or indirectly via streptavidin-biotin linkages; (iii) antibodies specific for a target molecule and conjugated to a bead, or microbead, or other solid phase support, which, in turn, is derivatized either directly or indirectly with moieties such as molecular tags or photosensitizers, or polymers containing the latter.

"Antigenic determinant," or "epitope" means a site on the surface of a molecule, usually a protein, to which a single antibody molecule binds; generally a protein has several or many different antigenic determinants and reacts with antibodies of many different specificities. A preferred antigenic determinant is a phosphorylation site of a protein.

"Binding moiety" means any molecule to which molecular tags can be directly or indirectly attached that is capable of specifically binding to an analyte. Binding moieties include, but are not limited to, antibodies, antibody binding compositions, peptides, proteins, nucleic acids, and organic molecules having a molecular weight of up to 1000 daltons and consisting of atoms selected from the group consisting of hydrogen, carbon, oxygen, nitrogen, sulfur, and phosphorus. Preferably, binding moieties are antibodies or antibody binding compositions.

"Capillary-sized" in reference to a separation column means a capillary tube or channel in a plate or microfluidics device, where the diameter or largest dimension of the separation column is between about 25-500 microns, allowing efficient heat dissipation throughout the separation medium, with consequently low thermal convection within the medium.

"Chromatography" or "chromatographic separation" as used herein means or refers to a method of analysis in which the flow of a mobile phase, usually a liquid, containing a mixture of compounds, e.g. molecular tags, promotes the separation of such compounds based on one or more physical or chemical properties by a differential distribution between the mobile phase and a stationary phase, usually a solid. The one or more physical characteristics that form the basis for chromatographic separation of analytes, such as molecular tags, include but are not limited to molecular weight, shape, solubility, pKa, hydrophobicity, charge, polarity, and the like. In one aspect, as used herein, "high pressure (or performance) liquid chromatography" ("HPLC") refers to a liquid phase chromatographic separation that (i) employs a rigid cylindrical separation column having a length of up to 300 mm and an inside diameter of up to 5 mm, (ii) has a solid phase comprising rigid spherical particles (e.g. silica, alumina, or the like) having the same diameter of up to 5 µm packed into the separation column, (iii) takes place at a temperature in the range of from 35° C. to 80° C. and at column pressure up to 150 bars, and (iv) employs a flow rate in the range of from 1 µL/min to 4 mL/min. Preferably, solid phase particles for use in HPLC are further characterized in (i) having a narrow size distribution about the mean particle diameter, with substantially all particle diameters being within 10% of the mean, (ii) having the same pore size in the range of from 70 to 300 angstroms, (iii) having a surface area in the range of from 50 to 250 $m^2/g$, and (iv) having a bonding phase density (i.e. the number of retention ligands per unit area) in the range of from 1 to 5 per $nm^2$. Exemplary reversed phase chromatography media for separating molecular tags include particles, e.g. silica or alumina, having bonded to their surfaces retention ligands, such as phenyl groups, cyano groups, or aliphatic groups selected from the group including $C_8$ through $C_{18}$. Chromatography in reference to the invention includes "capillary electrochromatography" ("CEC"), and related techniques. CEC is a liquid phase chromatographic technique in which fluid is driven by electroosmotic flow through a capillary-sized column, e.g. with inside diameters in the range of from 30 to 100 µm. CEC is disclosed in Svec, Adv. Biochem. Eng. Biotechnol. 76: 1-47 (2002); Vanhoenacker et al, Electrophoresis, 22: 4064-4103 (2001); and like references. CEC column may use the same solid phase materials as used in conventional reverse phase HPLC and additionally may use so-called "monolithic" non-particular packings. In some forms of CEC, pressure as well as electroosmosis drives an analyte-containing solvent through a column.

"Complex" as used herein means an assemblage or aggregate of molecules in direct or indirect contact with one another. In one aspect, "contact," or more particularly, "direct contact" in reference to a complex of molecules, or in reference to specificity or specific binding, means two or more molecules are close enough so that attractive noncovalent interactions, such as Van der Waal forces, hydrogen bonding, ionic and hydrophobic interactions, and the like, dominate the interaction of the molecules. In such an aspect, a complex of molecules is stable in that under assay conditions the complex is thermodynamically more favorable than a non-aggregated, or non-complexed, state of its component molecules. As used herein, "complex" usually refers to a stable aggregate of two or more proteins, and is equivalently referred to as a "protein-protein complex." Most typically, a "complex" refers to a stable aggregate of two proteins. As used herein, an "intracellular complex" or "intracellular protein-protein complex," refers to a complex of proteins normally found in the cytoplasm or nucleus of a biological cell, and may include complexes of one or more intracellular proteins and a surface membrane receptor. Exemplary intracellular proteins that may be part of such complexes include, but are not limit to, PI3K proteins, Grb2 proteins, Grb7 proteins, Shc proteins, and Sos proteins, Src proteins, Cbl proteins, PLCγ proteins, Shp2 proteins, GAP proteins, Nck proteins, Vav proteins, and Crk proteins. In one aspect, such complexes include PI3K or Shc proteins. In another aspect, a complex is a stable aggregate comprising two proteins, or from 2 to 4 proteins, or from 2 to 6 proteins. As used herein, a "signaling complex" is an intracellular protein-protein complex that is a component of a signaling pathway.

"Dimer" in reference to cell surface membrane receptors means a complex of two or more membrane-bound receptor proteins that may be the same or different. Dimers of identical receptors are referred to as "homodimers" and dimers of different receptors are referred to as "heterodimers." Dimers usually consist of two receptors in contact with one another. Dimers may be created in a cell surface membrane by passive processes, such as Van der Waal interactions, and the like, as described above in the definition of "complex," or dimers may be created by active processes, such as by ligand-induced dimerization, covalent linkages, interaction with intracellular components, or the like, e.g. Schlessinger, Cell, 103: 211-225 (2000). As used herein, the term "dimer" is understood to refer to "cell surface membrane receptor dimer," unless understood otherwise from the context.

"Isolated" in reference to a polypeptide or protein means substantially separated from the components of its natural environment. Preferably, an isolated polypeptide or protein is a composition that consists of at least eighty percent of the polypeptide or protein identified by sequence on a weight basis as compared to components of its natural environment; more preferably, such composition consists of at least ninety-five percent of the polypeptide or protein identified by sequence on a weight basis as compared to components of its natural environment; and still more preferably, such composition consists of at least ninety-nine percent of the polypeptide or protein identified by sequence on a weight basis as compared to components of its natural environment. Most preferably, an isolated polypeptide or protein is a homogeneous composition that can be resolved as a single spot after conventional separation by two-dimensional gel electrophoresis based on molecular weight and isoelectric point. Protocols for such analysis by conventional two-dimensional gel electrophoresis are well known to one of ordinary skill in the art, e.g. Hames and Rickwood, Editors, Gel Electrophoresis of Proteins: A Practical Approach (IRL Press, Oxford, 1981); Scopes, Protein Purification (Springer-Verlag, New York, 1982); Rabilloud, Editor, Proteome Research: Two-Dimensional Gel Electrophoresis and Identification Methods (Springer-Verlag, Berlin, 2000).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

The term "ligand" is also used herein to refer to a secreted protein or protein thereof which binds to a given receptor, through a ligand-receptor interaction.

"Membrane-associated analyte" means a substance, compound, molecule, or component or part of any of the foregoing that is directly or indirectly attached to a membrane, especially a biological membrane such as the cell surface membrane of a mammalian cell or tissue. The attachment may be direct, for example, when a membrane-associated analyte has a lipophilic moiety, or is attached to another molecule that has a lipophilic moiety, capable of anchoring it in a membrane. The attachment may also be indirect, for example, when a membrane-associated analyte is a soluble ligand that binds to, and forms a stable complex with, a cell surface receptor. A membrane-associated analyte may be, but is not limited to, a peptide, protein, polynucleotide, polypeptide, oligonucleotide, organic molecule, hapten, epitope, part of a biological cell, a posttranslational modification of a protein, a receptor, a complex sugar attached to a membrane component such as a receptor, a soluble compound forming a stable complex with a membrane such as a vitamin, a hormone, a cytokine, or the like, forming and the like. There may be more than one analyte associated with a single molecular entity, e.g. different phosphorylation sites on the same protein. Membrane-associated analytes include cell surface molecules, such as cell membrane receptors. In one aspect of the invention, membrane-associated analytes are cell membrane receptors selected from the group consisting of epidermal growth factor receptors and G-protein coupled receptors. In particular, epidermal growth factor receptors include Her1, Her2, Her3, and Her4 receptors, e.g. Yarden (cited above); Yarden and Sliwkowski (cited above). "Dimer" in reference to membrane-associated analytes means a stable, usually non-covalent, association of two membrane-associated analytes. A dimer of membrane-associated analytes may form as the result of interaction with a ligand, i.e. ligand-induced dimerization, e.g. Schlessinger, Cell, 110: 669-672 (2002). "Oligomer" in reference to membrane-associated analytes means a stable, usually non-covalent, association of at least two membrane-associated analytes.

"Polypeptide" refers to a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides. There is no clear-cut distinction between polypeptides and peptides. For convenience, in this disclosure and claims, the term "polypeptide" will be used to refer generally to peptides and polypeptides. The amino acid residues may be natural or synthetic.

"Protein" refers to a polypeptide, usually synthesized by a biological cell, folded into a defined three-dimensional structure. Proteins are generally from about 5,000 to about 5,000,000 or more in molecular weight, more usually from about 5,000 to about 1,000,000 molecular weight, and may include post-translational modifications, such acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, farnesylation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, phosphorylation, prenylation, racemization, selenoylation, sulfation, and ubiquitination, e.g. Wold, F., Post-translational Protein Modifications: Perspectives and Prospects, pgs. 1-12 in Post-translational Covalent Modification of Proteins, B. C. Johnson, Ed., Academic Press, New York, 1983. In one aspect, post-translational modifications are usually phosphylations of proteins that are components of a signaling pathway. Proteins include, by way of illustration and not limitation, cytokines or interleukins, enzymes such as, e.g., kinases, proteases, galactosidases and so forth, protamines, histones, albumins, immunoglobulins, scleroproteins, phosphoproteins, mucoproteins, chromoproteins, lipoproteins, nucleoproteins, glycoproteins, T-cell receptors, proteoglycans, and the like.

"Receptor complex" means a complex that comprises at least one cell surface membrane receptor. Receptor complexes may include a dimer of cell surface membrane receptors, or one or more intracellular proteins, such as adaptor proteins, that form links in the various signaling pathways. Exemplary intracellular proteins that may be part of a receptor complex includes, but is not limit to, PI3K proteins, Grb2 proteins, Grb7 proteins, Shc proteins, and Sos proteins, Src proteins, Cbl proteins, PLCγ proteins, Shp2 proteins, GAP proteins, Nck proteins, Vav proteins, and Crk proteins. In one aspect, receptor complexes include PI3K or Shc proteins.

"Receptor tyrosine kinase," or "RTK," means a human receptor protein having intracellular kinase activity and being selected from the RTK family of proteins described in Schlessinger, Cell, 103: 211-225 (2000); and Blume-Jensen and Hunter (cited above). "Receptor tyrosine kinase dimer" means a complex in a cell surface membrane comprising two receptor tyrosine kinase proteins. In some aspects, a receptor tyrosine kinase dimer may comprise two covalently linked receptor tyrosine kinase proteins. Exemplary RTK dimers are listed in Table I. RTK dimers of particular interest are Her receptor dimers and VEGFR dimers.

"Sample" or "tissue sample" or "patient sample" or "patient cell or tissue sample" or "specimen" each means a collection of similar cells obtained from a tissue of a subject or patient. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. The tissue sample may contain compounds which are not naturally intermixed with the tissue in nature such as preservatives, anticoagulants, buffers, fixatives, nutrients, antibiotics, or the like. In one aspect of the invention, tissue samples or patient samples are fixed, particularly conventional formalin-fixed paraffin-embedded samples. Such samples are typically used in an assay for receptor complexes in the form of thin sections, e.g. 3-10 μm thick, of fixed tissue mounted on a microscope slide, or equivalent surface. Such samples also typically undergo a conventional re-hydration procedure, and optionally, an antigen retrieval procedure as a part of, or preliminary to, assay measurements.

"Separation profile" in reference to the separation of molecular tags means a chart, graph, curve, bar graph, or other representation of signal intensity data versus a parameter related to the molecular tags, such as retention time, mass, or the like, that provides a readout, or measure, of the number of molecular tags of each type produced in an assay. A separation profile may be an electropherogram, a chromatogram, an electrochromatogram, a mass spectrogram, or like graphical representation of data depending on the separation technique employed. A "peak" or a "band" or a "zone" in reference to a separation profile means a region where a separated compound is concentrated. There may be multiple separation profiles for a single assay if, for example, different molecular tags have different fluorescent labels having distinct emission spectra and data is collected and recorded at multiple wavelengths. In one aspect, released molecular tags are separated by differences in electrophoretic mobility to form an electropherogram wherein different molecular tags correspond to distinct peaks on the electropherogram. A measure of the distinctness, or lack of overlap, of adjacent peaks in an electropherogram is "electrophoretic resolution," which may be taken as the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of molecular tags whose members have electrophoretic mobilities that differ by at least a peak-resolving amount, such quantity depending on several factors well known to those of ordinary skill, including signal detection system, nature of the fluorescent moieties, the diffusion coefficients of the tags, the presence or absence of sieving matrices, nature of the electrophoretic apparatus, e.g. presence or absence of channels, length of separation channels, and the like. Electropherograms may be analyzed to associate features in the data with the presence, absence, or quantities of molecular tags using analysis programs, such as disclosed in Williams et al, U.S. patent publication 2003/0170734 A1.

"Specific" or "specificity" in reference to the binding of one molecule to another molecule, such as a binding compound, or probe, for a target analyte or complex, means the recognition, contact, and formation of a stable complex between the probe and target, together with substantially less recognition, contact, or complex formation of the probe with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In one aspect, this largest number is at least fifty percent of all such complexes form by the first molecule. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like.

DETAILED DESCRIPTION OF THE INVENTION

The present invention provides methods and kits for detecting and/or measuring dimers and/or oligomers of cell surface receptors, particularly homodimers or homo-oligomers of cell surface receptors.

Figure 1B:
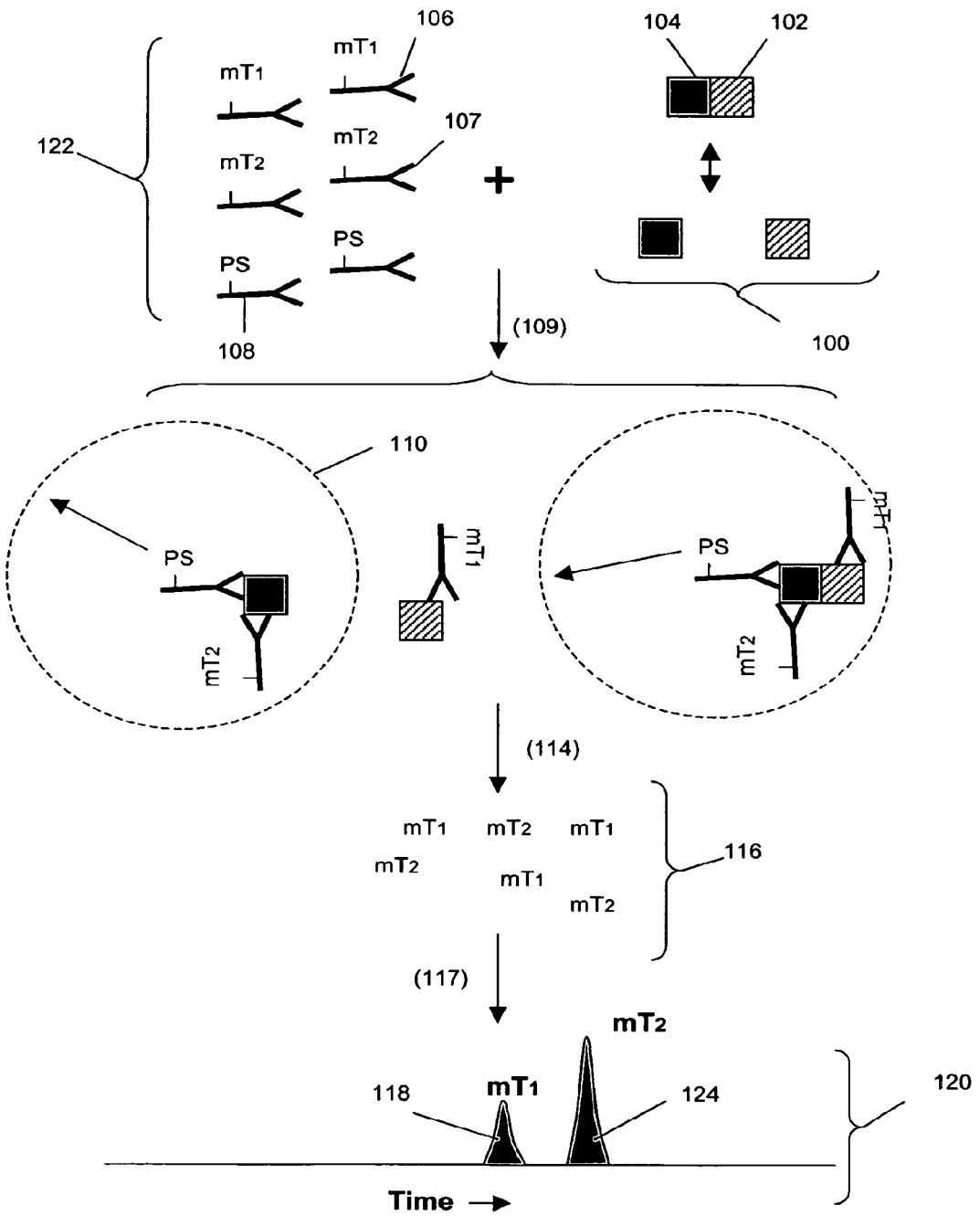

In one aspect of the invention, homodimeric complexes may be measured as illustrated in FIG. 1A. An assay may comprise three reagents (1128): cleaving probes (1134), first binding compound (1130), and second binding compound (1132). First binding compound (1130) and cleaving probe (1134) are constructed to be specific for the same antigenic determinant (1135) on protein (1138) that exists in a membrane as either a homodimer (1136) or a monomer (1138). After reagents (1128) are combined with a sample under conditions that promote the formation of stable complexes between the reagents and their respective targets, multiple complexes (1142 through 1150) form in the assay mixture. Because cleaving probe (1134) and binding compound (1130) are specific for the same antigenic determinant (1135), four different combinations (1144 through 1150) of reagents may form complexes with homodimers. Of the complexes in the assay mixture, only those (1143) with both a cleaving probe (1134) and at least one binding compound will contribute released molecular tags (1151) for separation and detection (1154). In this embodiment, the size of peak (1153) is proportional to the amount of homodimer in the assay mixture, while the size of peak (1152) is proportional to the total amount of protein (1138) in the assay mixture, both in monomeric form (1142) or in homodimeric form (1146 and 1148). FIG. 1B illustrates the analogous measurements for cell surface receptors that form heterodimers in a cell surface membrane. One skilled in the art would understand that dimmers may be measured in either lysates of cells or tissues, or in fixed samples whose membranes have been permeabilized or removed by the fixing process. In such cases, binding compounds may be specific for either extracellular or intracellular domains of cell surface membrane receptors. Optionally, prior to illumination the binding buffer may be removed and replaced with a buffer more suitable for separation, i.e. a separation buffer. For example, binding buffers typically have salt concentrations that may degrade the performance of some separation techniques, such as capillary electrophoresis, for separating molecular tags into distinct peaks. In one embodiment, such exchange of buffers may be accomplished by membrane filtration.

As mentioned above, a method of measuring signaling complexes comprising heterodimers is illustrated in FIG. 1B. Heterodimeric complex (100) forms by the binding of proteins (104) and (102), e.g. Akt and PDK 1. Reagents (122) of the invention, comprising cleaving probes (108) (in this illustration having photosensitizer "PS" attached) and binding compounds (106), are mixed (109) with a sample containing complex (100) under conditions that permit the specific binding (112) of cleaving probes (108) and binding compounds (106) to their respective antigenic determinants on complex (100) that are on different proteins of the complex. After binding, and optionally washing or buffer exchange, cleaving probes (108) are activated to generate an active species that, e.g. in the case of singlet oxygen, diffuses out from a photosensitizers to an effective proximity (110). Cleavable linkages within this proximity are cleaved and molecular tags are released (114). Released molecular tags (116) are then separated (117) and a separation profile (120), such as an electropherogram, is produced, in which peak (118) is identified and correlated to molecular tag, "$mT_1$" and peak (124) is identified and correlated with molecular tag, "$mT_2$." By employing additional binding compounds and molecular tags, additional complexes may be measured. As with the ratiometric measure of an activated effector protein, the amount of heterodimeric complexes may be provided as a ratio of peak areas. FIG. 1D illustrates the analogous measurements for cell surface receptors that form heterodimers in cell surface membrane (161).

Figure 1C:
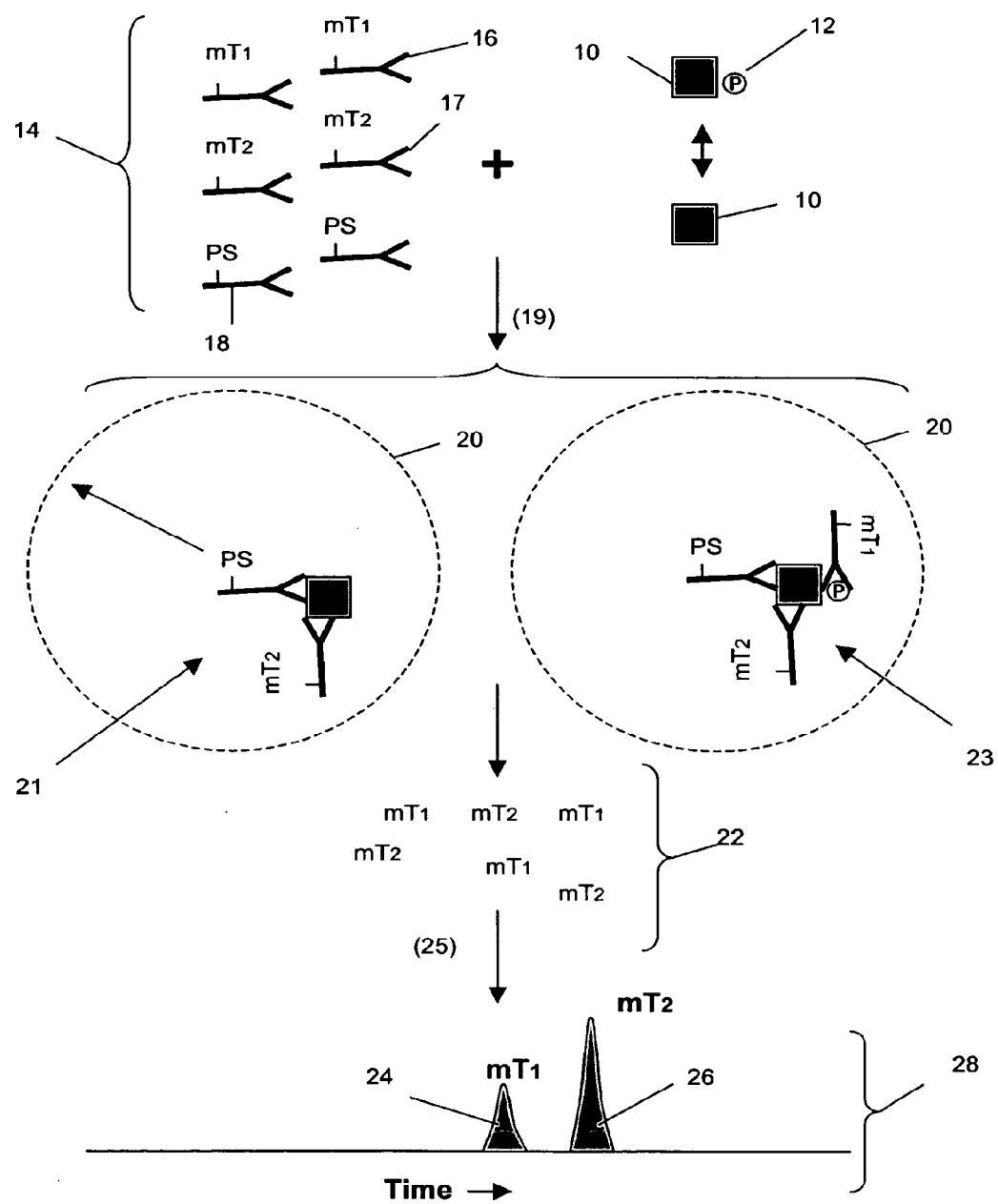
Figure 1D:
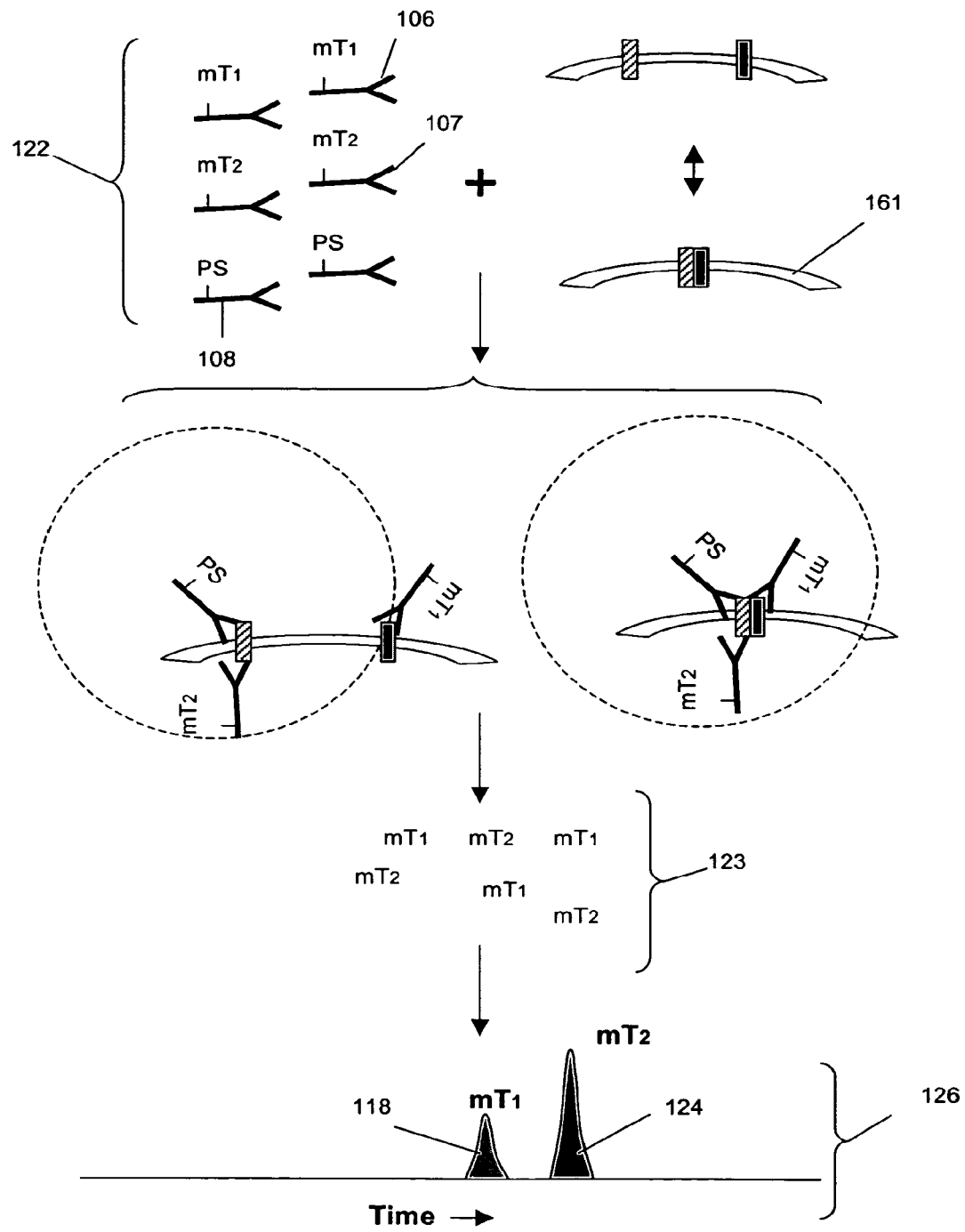

In some embodiments of the invention, ratiometric measurements may be made on effector proteins or receptor components having post-translational modifications, such as phosphoylation, as illustrated in FIG. 1C. Effector protein or receptor component (10) exists in two states in a cell, one having a post-translational modification, e.g. such as a phosphate group (12), and the other not having such a post-translational modification. Reagents (14) of the invention, comprising cleaving probes (18) (in this illustration having photosensitizer "PS" attached) and binding compounds (16), are mixed (19) with a sample containing both the activated and inactivated forms of effector protein or receptor component (10) under conditions that permit the specific binding of cleaving probes (18) and binding compounds (16) to their respective antigenic determinants on the activated and inactivated forms of effector protein or receptor component (10) resulting in the formation of either complex (21) or complex (23). After binding, and optionally washing or buffer exchange, cleaving probes (18) are activated to generate an active species that, e.g. in the case of singlet oxygen, diffuses out from a photosensitizers to an effective proximity (20). Cleavable linkages within this proximity are cleaved and molecular tags are released (22). Released molecular tags (22) are then separated (25) and a separation profile (28), such as an electropherogram, is produced, in which peak (24) is identified and correlated to molecular tag, "$mT_1$" and peak (26) is identified and correlated to molecular tag, "$mT_2$." In one aspect, a ratiometric measure of activated effector protein or receptor component (10) is provided as the ratio of areas of peaks (24) and (26).

Figure 1E:
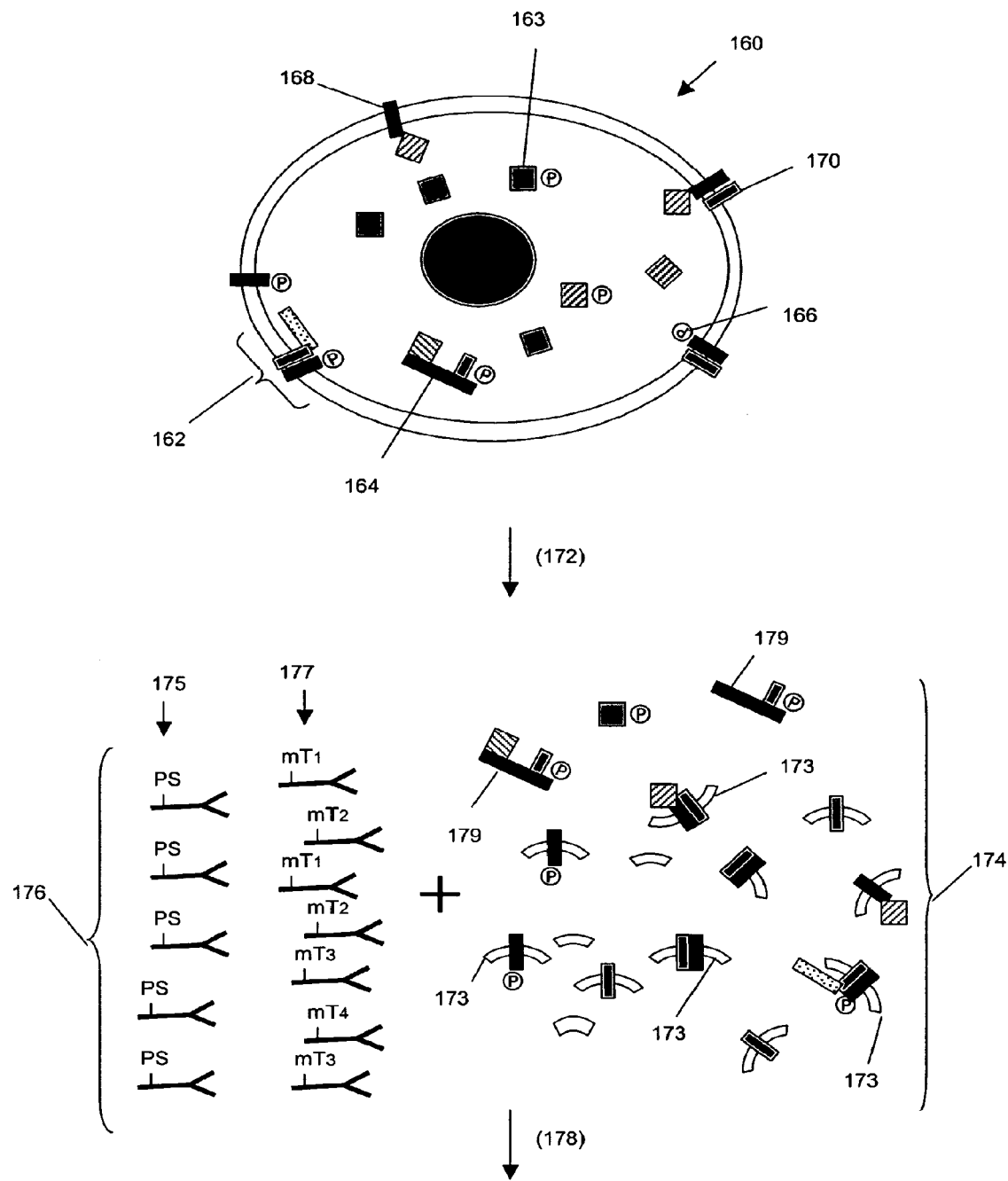
Figure 1F:
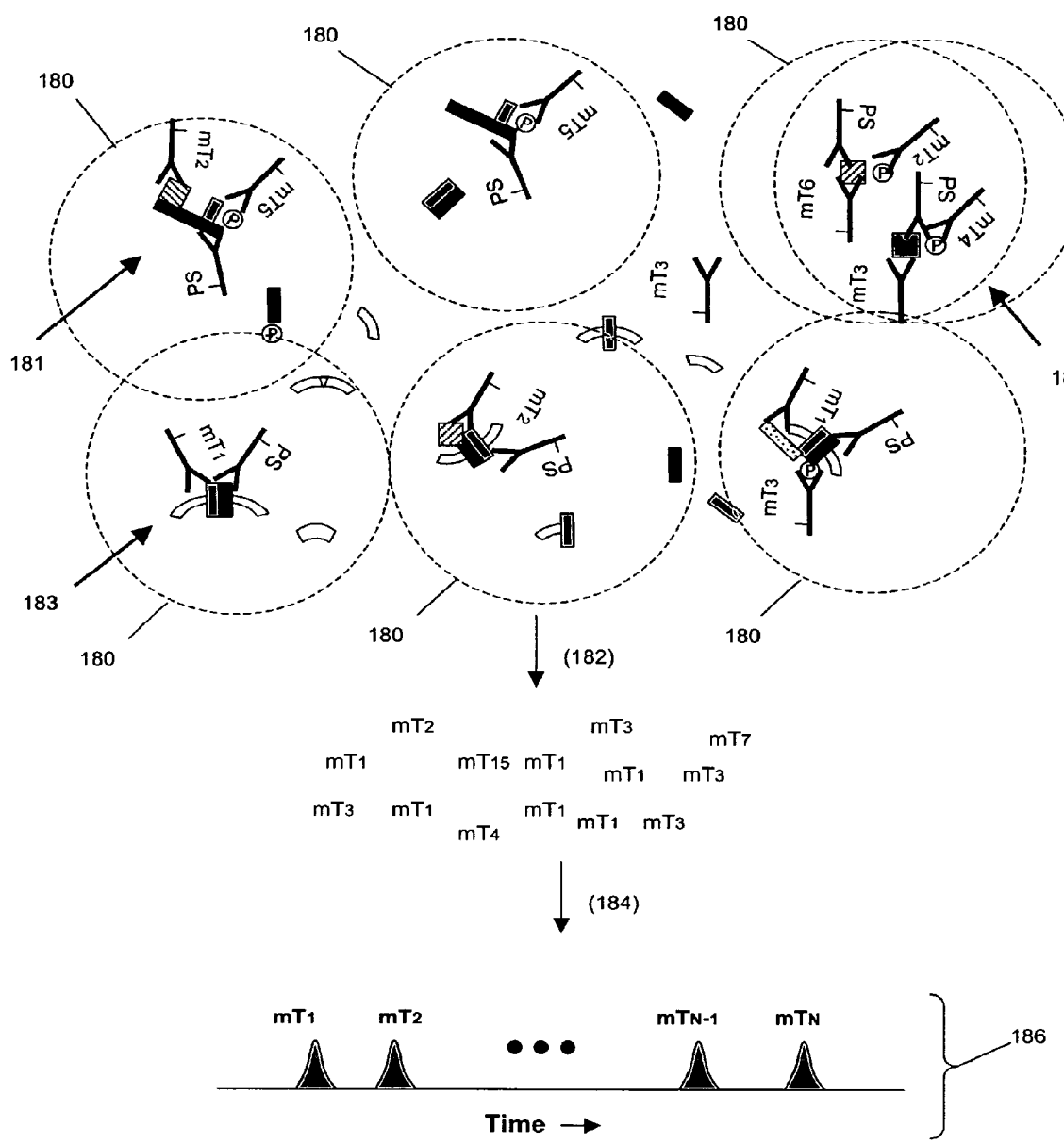

Another aspect of the invention is illustrated in FIGS. 1E and 1F, which provides for the simultaneous detection or measurement of multiple complexes, dimers, and activated effector proteins in a cellular sample. Cells (160), which may be from a sample from in vitro cultures or from a specimen of patient tissue, are lysed (172) to form lysate (174) in which cellular components are rendered accessible, such components including molecular complexes associated with the cell membrane (173), and/or within the cytosol (179), and/or within the cell nucleus. Complexes associated with signaling pathways include, but are not limited to, surface receptor complexes, such as receptor dimers (162 or 170), receptor complexes including adaptor or scaffold molecules of various types (162, 168, or 170), dimers and higher order complexes of intracellular proteins (164), phosphorylation sites of proteins in such complexes (166), phosphorylated effector proteins (163), and the like. After lysing, the resulting lysate (174) is combined with assay reagents (176) that include multiple cleaving probes (175) and multiple binding compounds (177). Assay conditions are selected (178) that allow reagents (176) to specifically bind to their respective targets, so that upon activation cleavable linkages within the effective proximity (180) of the cleavage-inducing moieties are cleaved and molecular tags are released (182). Also illustrated are intracellular complexes, e.g. signaling complexes (181), receptor dimers (183), and effector proteins (185). As above, after cleavage, the released molecular tags are separated (184) and identified in a separation profile (186), such as an electropherogram, and based on the number and quantities of molecular tags measured, a profile is obtained of the selected molecular complexes, RTK dimers, and/or effector proteins in the cells of the sample. One skilled in the art would understand that dimers may be measured in either lysates of cells or tissues, or in fixed samples whose membranes have been permeabilized or removed by the fixing process. In such cases, binding compounds may be specific for either extracellular or intracellular domains of cell surface membrane receptors.

Figure 1G:
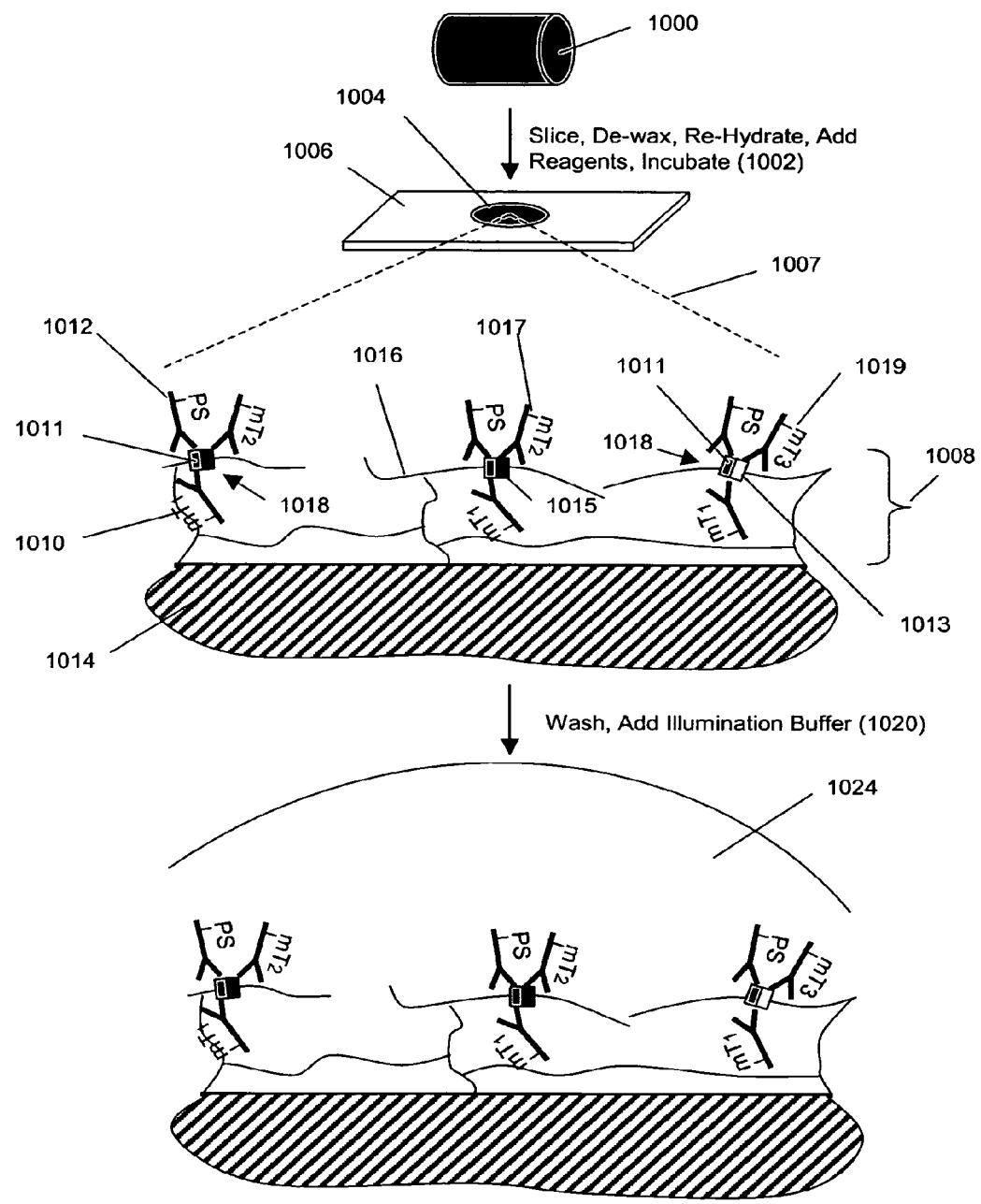
FIGS. 1G-1H illustrate diagrammatically the use of releasable molecular tags to measure cell surface receptor complexes in fixed tissue specimens.
Figure 1H:
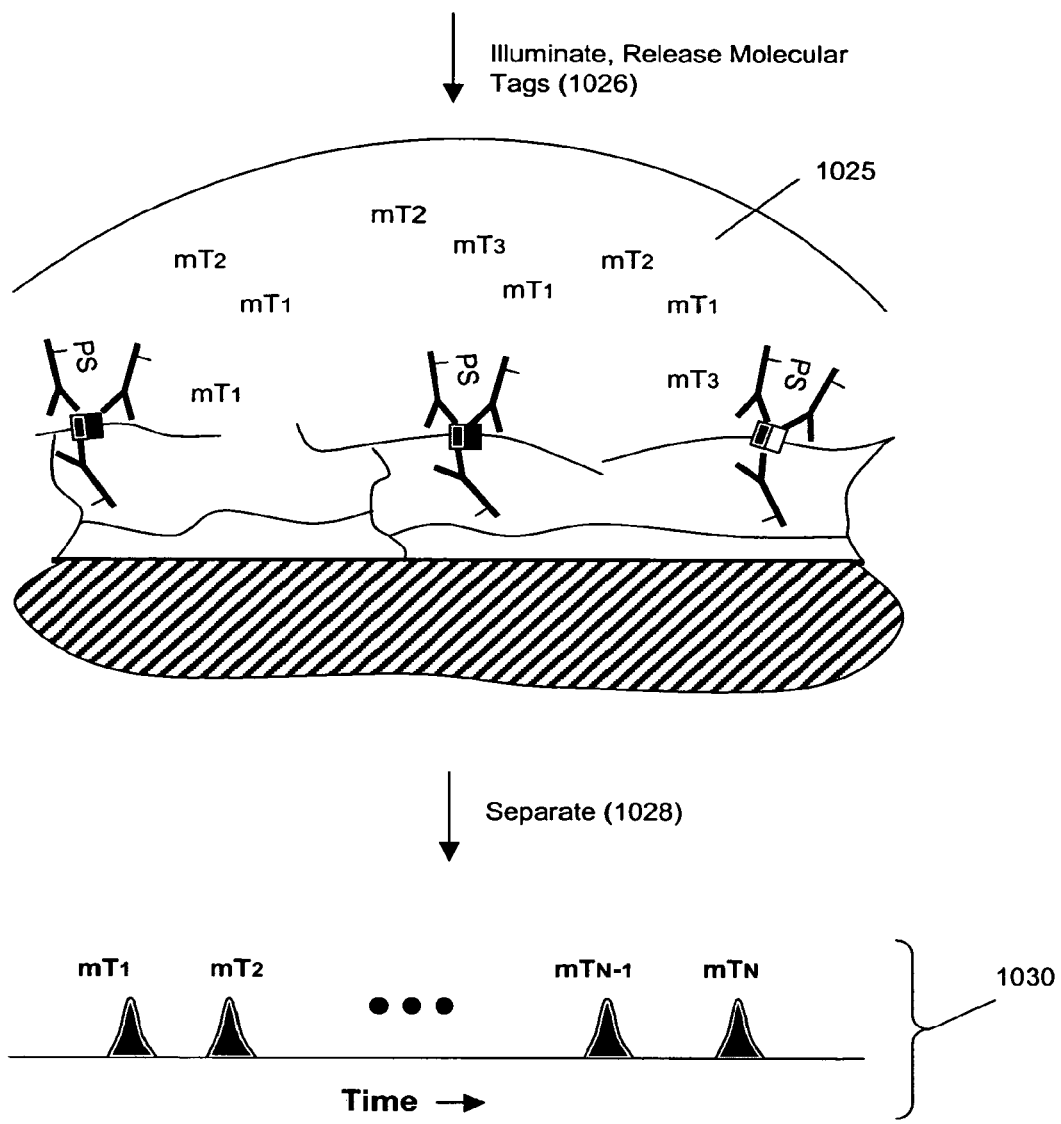

FIGS. 1G and 1H illustrate an embodiment of the invention for measuring receptor complexes in fixed or frozen tissue samples. Fixed tissue sample (1000), e.g. a formalin-fixed paraffin-embedded sample, is sliced to provide a section (1004) using a microtome, or like instrument, which after placing on surface (1006), which may be a microscope slide, it is de-waxed and re-hydrated for application of assay reagents. Enlargement (1007) shows portion (1008) of section (1004) on portion (1014) of microscope slide (1006). Receptor dimer molecules (1018) are illustrated as embedded in the remnants of membrane structure (1016) of the fixed sample. In accordance with this aspect of the invention, cleaving probe and binding compounds are incubated with the fixed sample so that they bind to their target molecules. For example, cleaving probes (1012)(illustrated in the figure as an antibody having a photosensitizer ("PS") attached) and first binding compound (1010)(illustrated as an antibody having molecular tag "$mT_{11}$" attached) specifically bind to receptor (1011) common to all of the dimers shown, second binding compound (1017)(with "mT₂") specifically binds to receptor (1015), and third binding compound (1019)(with "mT₃") specifically binds to receptor (1013). After washing to remove binding compounds and cleaving probe that are not specifically bound to their respective target molecules, buffer (1024) (referred to as "illumination buffer" in the figure) is added. For convenience, buffer (1024) may be contained on section (1004), or a portion thereof, by creating a hydrophobic barrier on slide (1006), e.g. with a wax pen. After illumination of photosensitizers and release of molecular tags (1026), buffer (1024) now containing release molecular tags (1025) is transferred to a separation device, such as a capillary electrophoresis instrument, for separation (1028) and identification of the released molecular tags in, for example, electropherogram (1030). Although the illustrations of FIGS. 1G and 1H describe measurement of heterodimers, one of ordinary skill in the art would appreciate that homodimers can be measured using similar techniques following the process described above, e.g. in relation to FIG. 1A.

Measurements made directly on tissue samples, particularly as illustrated in FIGS. 1G and 1H, may be normalized by including measurements on cellular or tissue targets that are representative of the total cell number in the sample and/or the numbers of particular subtypes of cells in the sample. The additional measurement may be preferred, or even necessary, because of the cellular and tissue heterogeneity in patient samples, particularly tumor samples, which may comprise substantial fractions of normal cells. For example, in FIG. 1H, values for the total amount of receptor (1011) may be given as a ratio of the following two measurements: area of peak (1032) of molecular tag ("mT₁") and the area of a peak corresponding to a molecular tag correlated with a cellular or tissue component common to all the cells in the sample, e.g. tubulin, or the like. In some cases, where all the cells in the sample are epithelial cells, cytokeratin may be used. Accordingly, detection methods based on releasable molecular tags may include an additional step of providing a binding compound (with a distinct molecular tag) specific for a normalization protein, such as tubulin.

Preparation of Samples

Samples containing molecular complexes may come from a wide variety of sources for use with the present invention to relate receptor complexes populations to disease status or health status, including cell cultures, animal or plant tissues, patient biopsies, or the like. Preferably, samples are human patient samples. Samples are prepared for assays of the invention using conventional techniques, which may depend on the source from which a sample is taken. A. Solid Tissue Samples. For biopsies and medical specimens, guidance is provided in the following references: Bancroft J D & Stevens A, eds. Theory and Practice of Histological Techniques (Churchill Livingstone, Edinburgh, 1977); Pearse, Histochemistry. Theory and applied. 4$^{th}$ ed. (Churchill Livingstone, Edinburgh, 1980).

In the area of cancerous disease status, examples of patient tissue samples that may be used include, but are not limited to, breast, prostate, ovary, colon, lung, endometrium, stomach, salivary gland or pancreas. The tissue sample can be obtained by a variety of procedures including, but not limited to surgical excision, aspiration or biopsy. The tissue may be fresh or frozen. In one embodiment, assays of the invention are carried out on tissue samples that have been fixed and embedded in paraffin or the like; therefore, in such embodiments a step of deparaffination is carried out. A tissue sample may be fixed (i.e. preserved) by conventional methodology [See e.g., "Manual of Histological Staining Method of the Armed Forces Institute of Pathology," 3$^{rd}$ edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C. One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample.

Generally, a tissue sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may have a thickness in a range from about three microns to about twelve microns, and preferably, a thickness in a range of from about 5 microns to about 10 microns. In one aspect, a section may have an area of from about 10 mm² to about 1 cm². Once cut, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De® (CMS, Houston, Tex.) may be used.

For mammalian tissue culture cells, fresh tissues, or like sources, samples may be prepared by conventional cell lysis techniques (e.g. 0.14 M NaCl, 1.5 mM MgCl₂, 10 mM Tris-Cl (pH 8.6), 0.5% Nonidet P-40, and protease and/or phosphatase inhibitors as required). For fresh mammalian tissues, sample preparation may also include a tissue disaggregation step, e.g. crushing, mincing, grinding, sonication, or the like.

B. Magnetic Isolation of Cells. In some applications, such as measuring dimers on rare metastatic cells from a patient's blood, an enrichment step may be carried out prior to conducting an assay for surface receptor dimer populations. Immunomagnetic isolation or enrichment may be carried out using a variety of techniques and materials known in the art, as disclosed in the following representative references that are incorporated by reference: Terstappen et al, U.S. Pat. No. 6,365,362; Terstappen et al, U.S. Pat. No. 5,646,001; Rohr et al, U.S. Pat. No. 5,998,224; Kausch et al, U.S. Pat. No. 5,665,582; Kresse et al, U.S. Pat. No. 6,048,515; Kausch et al, U.S. Pat. No. 5,508,164; Miltenyi et al, U.S. Pat. No. 5,691,208;

Molday, U.S. Pat. No. 4,452,773; Kronick, U.S. Pat. No. 4,375,407; Radbruch et al, chapter 23, in Methods in Cell Biology, Vol, 42 (Academic Press, New York, 1994); Uhlen et al, Advances in Biomagnetic Separation (Eaton Publishing, Natick, 1994); Safarik et al, J. Chromatography B, 722: 33-53 (1999); Miltenyi et al, Cytometry, 11: 231-238 (1990); Nakamura et al, Biotechnol. Prog., 17: 1145-1155 (2001); Moreno et al, Urology, 58: 386-392 (2001); Racila et al, Proc. Natl. Acad. Sci., 95: 4589-4594 (1998); Zigeuner et al, J. Urology, 169: 701-705 (2003); Ghossein et al, Seminars in Surgical Oncology, 20: 304-311 (2001).

The preferred magnetic particles for use in carrying out this invention are particles that behave as colloids. Such particles are characterized by their sub-micron particle size, which is generally less than about 200 nanometers (nm) (0.20 microns), and their stability to gravitational separation from solution for extended periods of time. In addition to the many other advantages, this size range makes them essentially invisible to analytical techniques commonly applied to cell analysis. Particles within the range of 90-150 nm and having between 70-90% magnetic mass are contemplated for use in the present invention. Suitable magnetic particles are composed of a crystalline core of superparamagnetic material surrounded by molecules which are bonded, e.g., physically absorbed or covalently attached, to the magnetic core and which confer stabilizing colloidal properties. The coating material should preferably be applied in an amount effective to prevent non specific interactions between biological macromolecules found in the sample and the magnetic cores. Such biological macromolecules may include sialic acid residues on the surface of non-target cells, lectins, glyproteins and other membrane components. In addition, the material should contain as much magnetic mass/nanoparticle as possible. The size of the magnetic crystals comprising the core is sufficiently small that they do not contain a complete magnetic domain. The size of the nanoparticles is sufficiently small such that their Brownian energy exceeds their magnetic moment. As a consequence, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698, 5,597,531 and 5,698,271, which patents are incorporated by reference.

Assays Using Releasable Molecular Tags

Many advantages are provided by measuring dimer populations using releasable molecular tags, including (1) separation of released molecular tags from an assay mixture provides greatly reduced background and a significant gain in sensitivity; and (2) the use of molecular tags that are specially designed for ease of separation and detection provides a convenient multiplexing capability so that multiple receptor complex components may be readily measured simultaneously in the same assay. Assays employing such tags can have a variety of forms and are disclosed in the following references: Singh et al, U.S. Pat. No. 6,627,400; U.S. patent publications Singh et al, 2002/0013126; and 2003/0170915, and Williams et al, 2002/0146726; and Chan-Hui et al, International patent publication WO 2004/011900, all of which are incorporated herein by reference. For example, a wide variety of separation techniques may be employed that can distinguish molecules based on one or more physical, chemical, or optical differences among molecules being separated including but not limited to electrophoretic mobility, molecular weight, shape, solubility, pKa, hydrophobicity, charge, charge/mass ratio, polarity, or the like. In one aspect, molecular tags in a plurality or set differ in electrophoretic mobility and optical detection characteristics and are separated by electrophoresis. In another aspect, molecular tags in a plurality or set may differ in molecular weight, shape, solubility, pKa, hydrophobicity, charge, polarity, and are separated by normal phase or reverse phase HPLC, ion exchange HPLC, capillary electrochromatography, mass spectroscopy, gas phase chromatography, or like technique.

Sets of molecular tags are provided that are separated into distinct bands or peaks by a separation technique after they are released from binding compounds. Identification and quantification of such peaks provides a measure or profile of the kinds and amounts of receptor dimers. Molecular tags within a set may be chemically diverse; however, for convenience, sets of molecular tags are usually chemically related. For example, they may all be peptides, or they may consist of different combinations of the same basic building blocks or monomers, or they may be synthesized using the same basic scaffold with different substituent groups for imparting different separation characteristics, as described more fully below. The number of molecular tags in a plurality may vary depending on several factors including the mode of separation employed, the labels used on the molecular tags for detection, the sensitivity of the binding moieties, the efficiency with which the cleavable linkages are cleaved, and the like. In one aspect, the number of molecular tags in a plurality for measuring populations of receptor dimers is in the range of from 2 to 10. In other aspects, the size of the plurality may be in the range of from 2 to 8, 2 to 6, 2 to 4, or 2 to 3.

Receptor dimers may be detected in assays having homogeneous formats or a non-homogeneous, i.e. heterogeneous, formats. In a homogeneous format, no step is required to separate binding compounds specifically bound to target complexes from unbound binding compounds. In a preferred embodiment, homogeneous formats employ reagent pairs comprising (i) one or more binding compounds with releasable molecular tags and (ii) at least one cleaving probe that is capable of generating an active species that reacts with and releases molecular tags within an effective proximity of the cleaving probe.

Receptor dimers may also be detected by assays employing a heterogeneous format. Heterogeneous techniques normally involve a separation step, where intracellular complexes having binding compounds specifically bound are separated from unbound binding compounds, and optionally, other sample components, such as proteins, membrane fragments, and the like. Separation can be achieved in a variety of ways, such as employing a reagent bound to a solid support that distinguishes between complex-bound and unbound binding compounds. The solid support may be a vessel wall, e.g., microtiter well plate well, capillary, plate, slide, beads, including magnetic beads, liposomes, or the like. The primary characteristics of the solid support are that it (1) permits segregation of the bound and unbound binding compounds and (2) does not interfere with the formation of the binding complex, or the other operations in the determination of receptor dimers. Usually, in fixed samples, unbound binding compounds are removed simply by washing.

With detection using molecular tags in a heterogeneous format, after washing, a sample may be combined with a solvent into which the molecular tags are to be released. Depending on the nature of the cleavable bond and the method of cleavage, the solvent may include any additional reagents for the cleavage. Where reagents for cleavage are not required, the solvent conveniently may be a separation buffer, e.g. an electrophoretic separation medium. For example, where the cleavable linkage is photolabile or cleavable via an active species generated by a photosensitizer, the medium may be irradiated with light of appropriate wavelength to release the molecular tags into the buffer.

In either format, if the assay reaction conditions interfere with the separation technique employed, it may be necessary to remove, or exchange, the assay reaction buffer prior to cleavage and separation of the molecular tags. For example, in some embodiments, assay conditions include salt concentrations (e.g. required for specific binding) that degrade separation performance when molecular tags are separated on the basis of electrophoretic mobility. In such embodiments, an assay buffer is replaced by a separation buffer, or medium, prior to release and separation of the molecular tags.

Assays employing releasable molecular tags and cleaving probes can be made in many different formats and configurations depending on the complexes that are detected or measured. Based on the present disclosure, it is a design choice for one of ordinary skill in the art to select the numbers and specificities of particular binding compounds and cleaving probes.

A. Binding Compounds

As mentioned above, mixtures containing pluralities of different binding compounds may be provided, wherein each different binding compound has one or more molecular tags attached through cleavable linkages. The nature of the binding compound, cleavable linkage and molecular tag may vary widely. A binding compound may comprise an antibody binding composition, an antibody, a peptide, a peptide or non-peptide ligand for a cell surface receptor, a protein, an oligonucleotide, an oligonucleotide analog, such as a peptide nucleic acid, a lectin, or any other molecular entity that is capable of specific binding or stable complex formation with an analyte of interest, such as a complex of proteins. In one aspect, a binding compound, which can be represented by the formula below, comprises one or more molecular tags attached to a binding moiety.

$$B\text{-}(L\text{-}E)_k$$

wherein B is binding moiety; L is a cleavable linkage; and E is a molecular tag. In homogeneous assays, cleavable linkage, L, may be an oxidation-labile linkage, and more preferably, it is a linkage that may be cleaved by singlet oxygen. The moiety "-(L-E)$_k$" indicates that a single binding compound may have multiple molecular tags attached via cleavable linkages. In one aspect, k is an integer greater than or equal to one, but in other embodiments, k may be greater than several hundred, e.g. 100 to 500, or k is greater than several hundred to as many as several thousand, e.g. 500 to 5000. Usually each of the plurality of different types of binding compound has a different molecular tag, E. Cleavable linkages, e.g. oxidation-labile linkages, and molecular tags, E, are attached to B by way of conventional chemistries.

Preferably, B is an antibody binding composition that specifically binds to a target, such as a predetermined antigenic determinant of a target protein, such as a cell surface receptor. Such compositions are readily formed from a wide variety of commercially available antibodies, both monoclonal and polyclonal, specific for proteins of interest. In particular, antibodies specific for epidermal growth factor receptors are disclosed in the following patents, which are incorporated by reference: U.S. Pat. Nos. 5,677,171; 5,772,997; 5,968,511; 5,480,968; 5,811,098. U.S. Pat. No. 6,488,390, incorporated herein by reference, discloses antibodies specific for a G-protein coupled receptor, CCR4. U.S. Pat. No. 5,599,681, incorporated herein by reference, discloses antibodies specific for phosphorylation sites of proteins. Commercial vendors, such as Cell Signaling Technology (Beverly, Mass.), Biosource International (Camarillo, Calif.), and Upstate (Charlottesville, Va.), also provide monoclonal and polyclonal antibodies specific for many receptors.

Cleavable linkage, L, can be virtually any chemical linking group that may be cleaved under conditions that do not degrade the structure or affect detection characteristics of the released molecular tag, E. Whenever a cleaving probe is used in a homogeneous assay format, cleavable linkage, L, is cleaved by a cleavage agent generated by the cleaving probe that acts over a short distance so that only cleavable linkages in the immediate proximity of the cleaving probe are cleaved. Typically, such an agent must be activated by making a physical or chemical change to the reaction mixture so that the agent produces a short lived active species that diffuses to a cleavable linkage to effect cleavage. In a homogeneous format, the cleavage agent is preferably attached to a binding moiety, such as an antibody, that targets prior to activation the cleavage agent to a particular site in the proximity of a binding compound with releasable molecular tags. In such embodiments, a cleavage agent is referred to herein as a "cleavage-inducing moiety," which is discussed more fully below.

In a non-homogeneous format, because specifically bound binding compounds are separated from unbound binding compounds, a wider selection of cleavable linkages and cleavage agents are available for use. Cleavable linkages may not only include linkages that are labile to reaction with a locally acting reactive species, such as hydrogen peroxide, singlet oxygen, or the like, but also linkages that are labile to agents that operate throughout a reaction mixture, such as base-labile linkages, photocleavable linkages, linkages cleavable by reduction, linkages cleaved by oxidation, acid-labile linkages, peptide linkages cleavable by specific proteases, and the like. References describing many such linkages include Greene and Wuts, Protective Groups in Organic Synthesis, Second Edition (John Wiley & Sons, New York, 1991); Hermanson, Bioconjugate Techniques (Academic Press, New York, 1996); and Still et al, U.S. Pat. No. 5,565, 324.

In one aspect, commercially available cleavable reagent systems may be employed with the invention. For example, a disulfide linkage may be introduced between an antibody binding composition and a molecular tag using a heterofunctional agent such as N-succinimidyl 3-(2-pyridyldithio)propionate (SPDP), succinimidyloxycarbonyl-α-methyl-α-(2-pyridyldithio)toluene (SMPT), or the like, available from vendors such as Pierce Chemical Company (Rockford, Ill.). Disulfide bonds introduced by such linkages can be broken by treatment with a reducing agent, such as dithiothreitol (DTT), dithioerythritol (DTE), 2-mercaptoethanol, sodium borohydride, or the like. Typical concentrations of reducing agents to effect cleavage of disulfide bonds are in the range of from 10 to 100 mM. An oxidatively labile linkage may be introduced between an antibody binding composition and a molecular tag using the homobifunctional NHS ester cross-linking reagent, disuccinimidyl tartarate (DST)(available from Pierce) that contains central cis-diols that are susceptible to cleavage with sodium periodate (e.g., 15 mM periodate at physiological pH for 4 hours). Linkages that contain esterified spacer components may be cleaved with strong nucleophilic agents, such as hydroxylamine, e.g. 0.1 N hydroxylamine, pH 8.5, for 3-6 hours at 37° C. Such spacers can be introduced by a homobifunctional cross-linking agent such as ethylene glycol bis(succinimidylsuccinate)(EGS) available from Pierce (Rockford, Ill.). A base labile linkage can be introduced with a sulfone group. Homobifunctional cross-linking agents that can be used to introduce sulfone groups in a cleavable linkage include bis[2-(succinimidyloxycarbonyloxy) ethyl]sulfone (BSOCOES), and 4,4-difluoro-3,3-dinitrophenylsulfone (DFDNPS). Exemplary basic conditions for cleavage include 0.1 M sodium phosphate, adjusted to pH 11.6 by addition of Tris base, containing 6 M urea, 0.1% SDS, and 2 mM DTT, with incubation at 37° C. for 2 hours. Photocleavable linkages include those disclosed in Rothschild et al, U.S. Pat. No. 5,986,076.

When L is oxidation labile, L may be a thioether or its selenium analog; or an olefin, which contains carbon-carbon double bonds, wherein cleavage of a double bond to an oxo group, releases the molecular tag, E. Illustrative oxidation labile linkages are disclosed in Singh et al, U.S. Pat. No. 6,627,400; and U.S. patent publications Singh et al, 2002/0013126; and 2003/0170915, and in Willner et al, U.S. Pat. No. 5,622,929, all of which are incorporated herein by reference.

Molecular tag, E, in the present invention may comprise an electrophoric tag as described in the following references when separation of pluralities of molecular tags are carried out by gas chromatography or mass spectrometry: Zhang et al, Bioconjugate Chem., 13: 1002-1012 (2002); Giese, Anal. Chem., 2: 165-168 (1983); and U.S. Pat. Nos. 4,650,750; 5,360,819; 5,516,931; 5,602,273; and the like.

Molecular tag, E, is preferably a water-soluble organic compound that is stable with respect to the active species, especially singlet oxygen, and that includes a detection or reporter group. Otherwise, E may vary widely in size and structure. In one aspect, E has a molecular weight in the range of from about 50 to about 2500 daltons, more preferably, from about 50 to about 1500 daltons. Preferred structures of E are described more fully below. E may comprise a detection group for generating an electrochemical, fluorescent, or chromogenic signal. In embodiments employing detection by mass, E may not have a separate moiety for detection purposes. Preferably, the detection group generates a fluorescent signal.

Molecular tags within a plurality are selected so that each has a unique separation characteristic and/or a unique optical property with respect to the other members of the same plurality. In one aspect, the chromatographic or electrophoretic separation characteristic is retention time under set of standard separation conditions conventional in the art, e.g. voltage, column pressure, column type, mobile phase, electrophoretic separation medium, or the like. In another aspect, the optical property is a fluorescence property, such as emission spectrum, fluorescence lifetime, fluorescence intensity at a given wavelength or band of wavelengths, or the like. Preferably, the fluorescence property is fluorescence intensity. For example, each molecular tag of a plurality may have the same fluorescent emission properties, but each will differ from one another by virtue of a unique retention time. On the other hand, or two or more of the molecular tags of a plurality may have identical migration, or retention, times, but they will have unique fluorescent properties, e.g. spectrally resolvable emission spectra, so that all the members of the plurality are distinguishable by the combination of molecular separation and fluorescence measurement.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by conventional capillary electrophoresis apparatus, either in the presence or absence of a conventional sieving matrix. Exemplary capillary electrophoresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Electrophoretic mobility is proportional to $q/m^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more. Preferably, in such conventional apparatus, the electrophoretic mobilities of molecular tags of a plurality differ by at least one percent, and more preferably, by at least a percentage in the range of from 1 to 10 percent. Molecular tags are identified and quantified by analysis of a separation profile, or more specifically, an electropherogram, and such values are correlated with the amounts and kinds of receptor dimers present in a sample. For example, during or after electrophoretic separation, the molecular tags are detected or identified by recording fluorescence signals and migration times (or migration distances) of the separated compounds, or by constructing a chart of relative fluorescent and order of migration of the molecular tags (e.g., as an electropherogram). Preferably, the presence, absence, and/or amounts of molecular tags are measured by using one or more standards as disclosed by Williams et al, U.S. patent publication 2003/0170734A1, which is incorporated herein by reference.

Pluralities of molecular tags may also be designed for separation by chromatography based on one or more physical characteristics that include but are not limited to molecular weight, shape, solubility, pKa, hydrophobicity, charge, polarity, or the like, e.g. as disclosed in U.S. patent publication 2003/0235832, which is incorporated by reference. A chromatographic separation technique is selected based on parameters such as column type, solid phase, mobile phase, and the like, followed by selection of a plurality of molecular tags that may be separated to form distinct peaks or bands in a single operation. Several factors determine which HPLC technique is selected for use in the invention, including the number of molecular tags to be detected (i.e. the size of the plurality), the estimated quantities of each molecular tag that will be generated in the assays, the availability and ease of synthesizing molecular tags that are candidates for a set to be used in multiplexed assays, the detection modality employed, and the availability, robustness, cost, and ease of operation of HPLC instrumentation, columns, and solvents. Generally, columns and techniques are favored that are suitable for analyzing limited amounts of sample and that provide the highest resolution separations. Guidance for making such selections can be found in the literature, e.g. Snyder et al, Practical HPLC Method Development, (John Wiley & Sons, New York, 1988); Millner, "High Resolution Chromatography: A Practical Approach", Oxford University Press, New York (1999), Chi-San Wu, "Column Handbook for Size Exclusion Chromatography", Academic Press, San Diego (1999), and Oliver, "HPLC of Macromolecules: A Practical Approach, Oxford University Press", Oxford, England (1989). In particular, procedures are available for systematic development and optimization of chromatographic separations given conditions, such as column type, solid phase, and the like, e.g. Haber et al, J.

Chromatogr. Sci., 38: 386-392 (2000); Outinen et al, Eur. J. Pharm. Sci., 6: 197-205 (1998); Lewis et al, J. Chromatogr., 592: 183-195 and 197-208 (1992); and the like. An exemplary HPLC instrumentation system suitable for use with the present invention is the Agilent 1100 Series HPLC system (Agilent Technologies, Palo Alto, Calif.).

In one aspect, molecular tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, B-L-(M, D)" designates binding compound of either of two forms: "B-L-M-D" or "B-L-D-M."

Detection moiety, D, may be a fluorescent label or dye, a chromogenic label or dye, an electrochemical label, or the like. Preferably, D is a fluorescent dye. Exemplary fluorescent dyes for use with the invention include water-soluble rhodamine dyes, fluoresceins, 4,7-dichlorofluoresceins, benzoxanthene dyes, and energy transfer dyes, disclosed in the following references: Handbook of Molecular Probes and Research Reagents, $8^{th}$ ed., (Molecular Probes, Eugene, 2002); Lee et al, U.S. Pat. No. 6,191,278; Lee et al, U.S. Pat. No. 6,372,907; Menchen et al, U.S. Pat. No. 6,096,723; Lee et al, U.S. Pat. No. 5,945,526; Lee et al, Nucleic Acids Research, 25: 2816-2822 (1997); Hobb, Jr., U.S. Pat. No. 4,997,928; Khanna et al., U.S. Pat. No. 4,318,846; and the like. Preferably, D is a fluorescein or a fluorescein derivative.

Figure 2A:
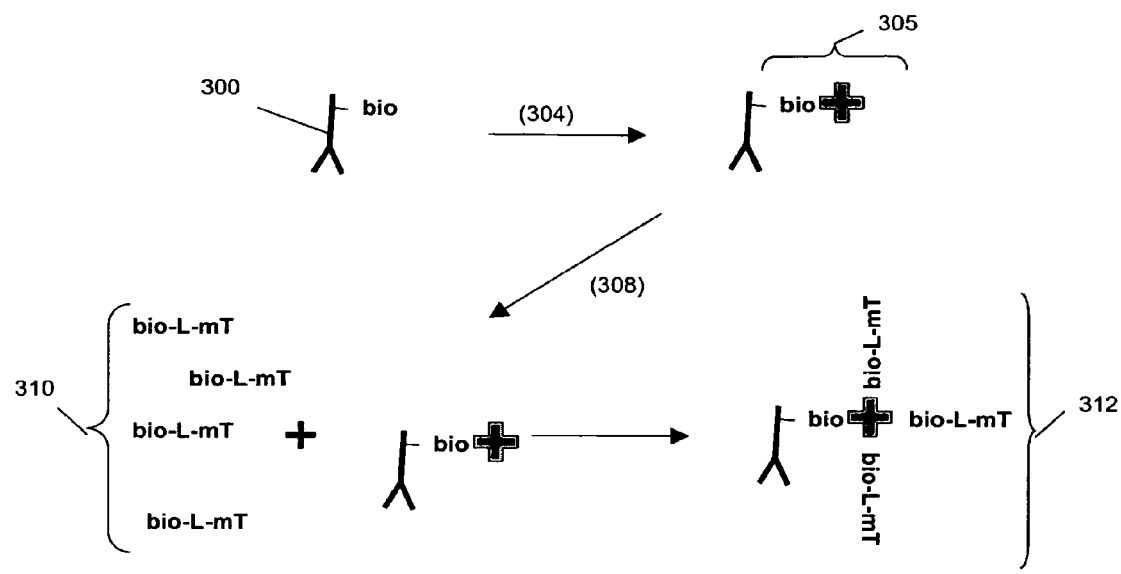
FIGS. 2A-2D illustrate diagrammatically methods for attaching molecular tags to antibodies.

In an embodiment illustrated in FIG. 2A, binding compounds comprise a biotinylated antibody (300) as a binding moiety. Molecular tags are attached to binding moiety (300) by way of avidin or streptavidin bridge (306). Preferably, in operation, binding moiety (300) is first reacted with a target complex, after which avidin or streptavidin is added (304) to form antibody-biotin-avidin complex (305). To such complexes (305) are added (308) biotinylated molecular tags (310) to form binding compound (312).

Figure 2B:
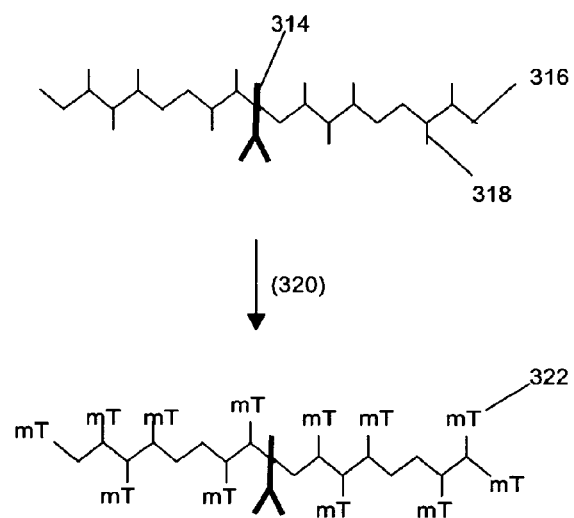

In still another embodiment illustrated in FIG. 2B, binding compounds comprise an antibody (314) derivatized with a multi-functional moiety (316) that contains multiple functional groups (318) that are reacted (320) molecular tag precursors to give a final binding compound having multiple molecular tags (322) attached. Exemplary multi-functional moieties include aminodextran, and like materials.

Once each of the binding compounds is separately derivatized by a different molecular tag, it is pooled with other binding compounds to form a plurality of binding compounds. Usually, each different kind of binding compound is present in a composition in the same proportion; however, proportions may be varied as a design choice so that one or a subset of particular binding compounds are present in greater or lower proportion depending on the desirability or requirements for a particular embodiment or assay. Factors that may affect such design choices include, but are not limited to, antibody affinity and avidity for a particular target, relative prevalence of a target, fluorescent characteristics of a detection moiety of a molecular tag, and the like.

B. Cleavage-Inducing Moiety Producing Active Species

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al, Meth. Enzymol., 319: 226-241 (2000).

An important consideration in designing assays employing a cleavage-inducing moiety and a cleavable linkage is that they not be so far removed from one another when bound to a receptor complex that the active species generated by the cleavage-inducing moiety cannot efficiently cleave the cleavable linkage. In one aspect, cleavable linkages preferably are within 1000 nm, and preferably within 20-200 nm, of a bound cleavage-inducing moiety. More preferably, for photosensitizer cleavage-inducing moieties generating singlet oxygen, cleavable linkages are within about 20-100 nm of a photosensitizer in a receptor complex. The range within which a cleavage-inducing moiety can effectively cleave a cleavable linkage (that is, cleave enough molecular tag to generate a detectable signal) is referred to herein as its "effective proximity." One of ordinary skill in the art recognizes that the effective proximity of a particular sensitizer may depend on the details of a particular assay design and may be determined or modified by routine experimentation.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed in the following references: Di Mascio et al, FEBS Lett., 355: 287 (1994) (peroxidases and oxygenases); Kanofsky, J. Biol. Chem. 258: 5991-5993 (1983)(lactoperoxidase); Pierlot et al, Meth. Enzymol., 319: 3-20 (2000)(thermal lysis of endoperoxides); and the like. Attachment of a binding agent to the cleavage-inducing moiety may be direct or indirect, covalent or non-covalent and can be accomplished by well-known techniques, commonly available in the literature. See, for example, "Immobilized Enzymes," Ichiro Chibata, Halsted Press, New York (1978); Cuatrecasas, J. Biol. Chem., 245:3059 (1970).

As mentioned above, the preferred cleavage-inducing moiety in accordance with the present invention is a photosensitizer that produces singlet oxygen. As used herein, "photosensitizer" refers to a light-adsorbing molecule that when activated by light converts molecular oxygen into singlet oxygen. Photosensitizers may be attached directly or indirectly, via covalent or non-covalent linkages, to the binding agent of a class-specific reagent. Guidance for constructing of such compositions, particularly for antibodies as binding agents, available in the literature, e.g. in the fields of photodynamic therapy, immunodiagnostics, and the like. The following are exemplary references: Ullman, et al., Proc. Natl. Acad. Sci. USA 91, 5426-5430 (1994); Strong et al, Ann. New York Acad. Sci., 745: 297-320 (1994); Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251, 581; McCapra, U.S. Pat. No. 5,516,636; and the like.

A large variety of light sources are available to photoactivate photosensitizers to generate singlet oxygen. Both polychromatic and monochromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flashlamps; and the like. By way of example, a photoactivation device disclosed in Bjornson et al, International patent publication WO 03/051669 is employed. Briefly, the photoactivation device is an array of light emitting diodes (LEDs) mounted in housing that permits the simultaneous illumination of all the wells in a 96-well plate. A suitable LED for use in the present invention is a high power GaAIAs IR emitter, such as model OD-880W manufactured by OPTO DIODE CORP. (Newbury Park, Calif.).

Examples of photosensitizers that may be utilized in the present invention are those that have the above properties and are enumerated in the following references: Singh and Ullman, U.S. Pat. No. 5,536,834; Li et al, U.S. Pat. No. 5,763,602; Martin et al, Methods Enzymol., 186: 635-645 (1990); Yarmush et al, Crit. Rev. Therapeutic Drug Carrier Syst., 10: 197-252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516,636; Thetford, European patent publ. 0484027; Sessler et al, SPIE, 1426: 318-329 (1991); Magda et al, U.S. Pat. No. 5,565,552; Roelant, U.S. Pat. No. 6,001,673; and the like.

As with sensitizers, in certain embodiments, a photosensitizer may be associated with a solid phase support by being covalently or non-covalently attached to the surface of the support or incorporated into the body of the support. In general, the photosensitizer is associated with the support in an amount necessary to achieve the necessary amount of singlet oxygen. Generally, the amount of photosensitizer is determined empirically.

Figure 2C:
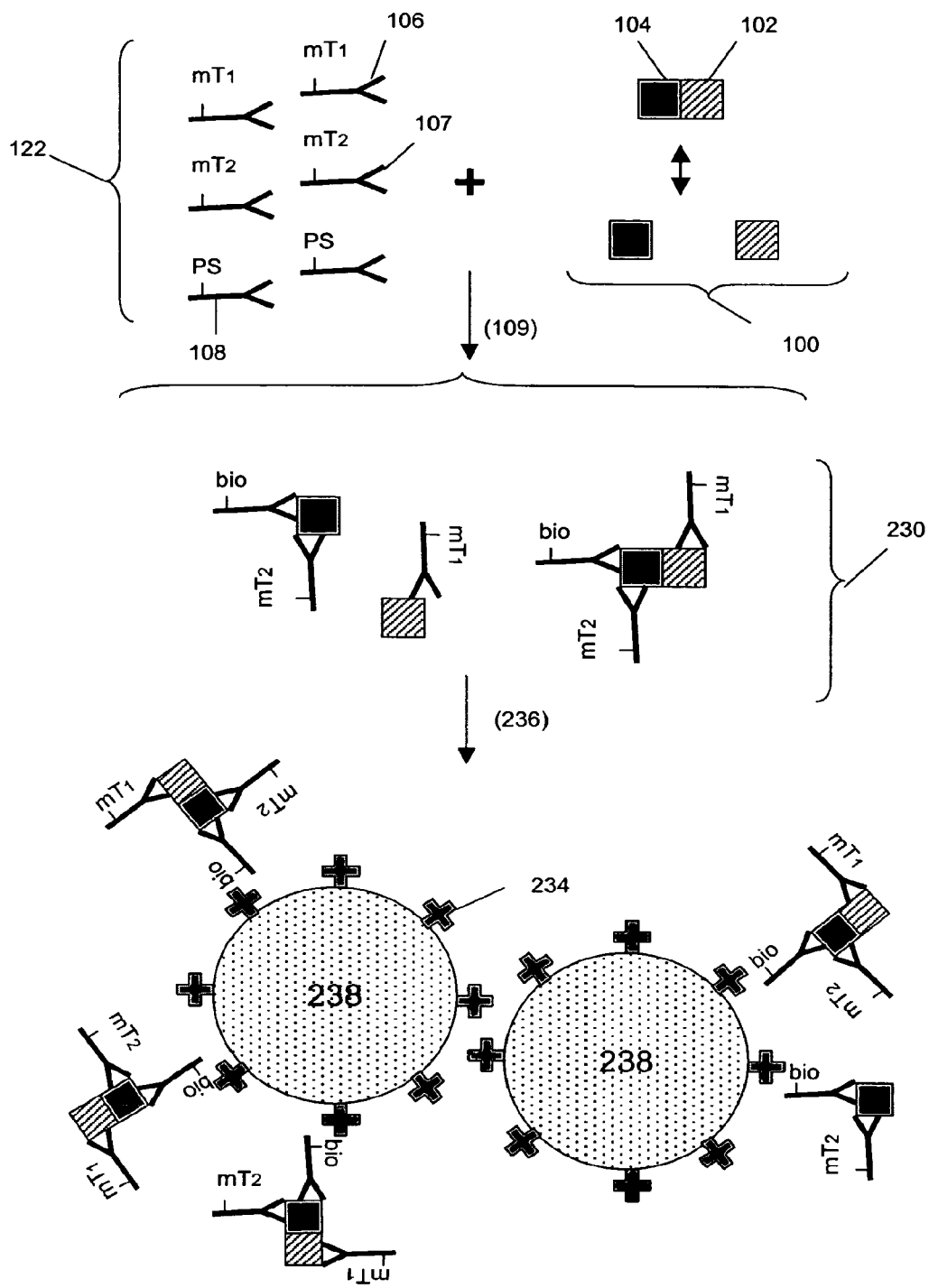
Figure 2D:
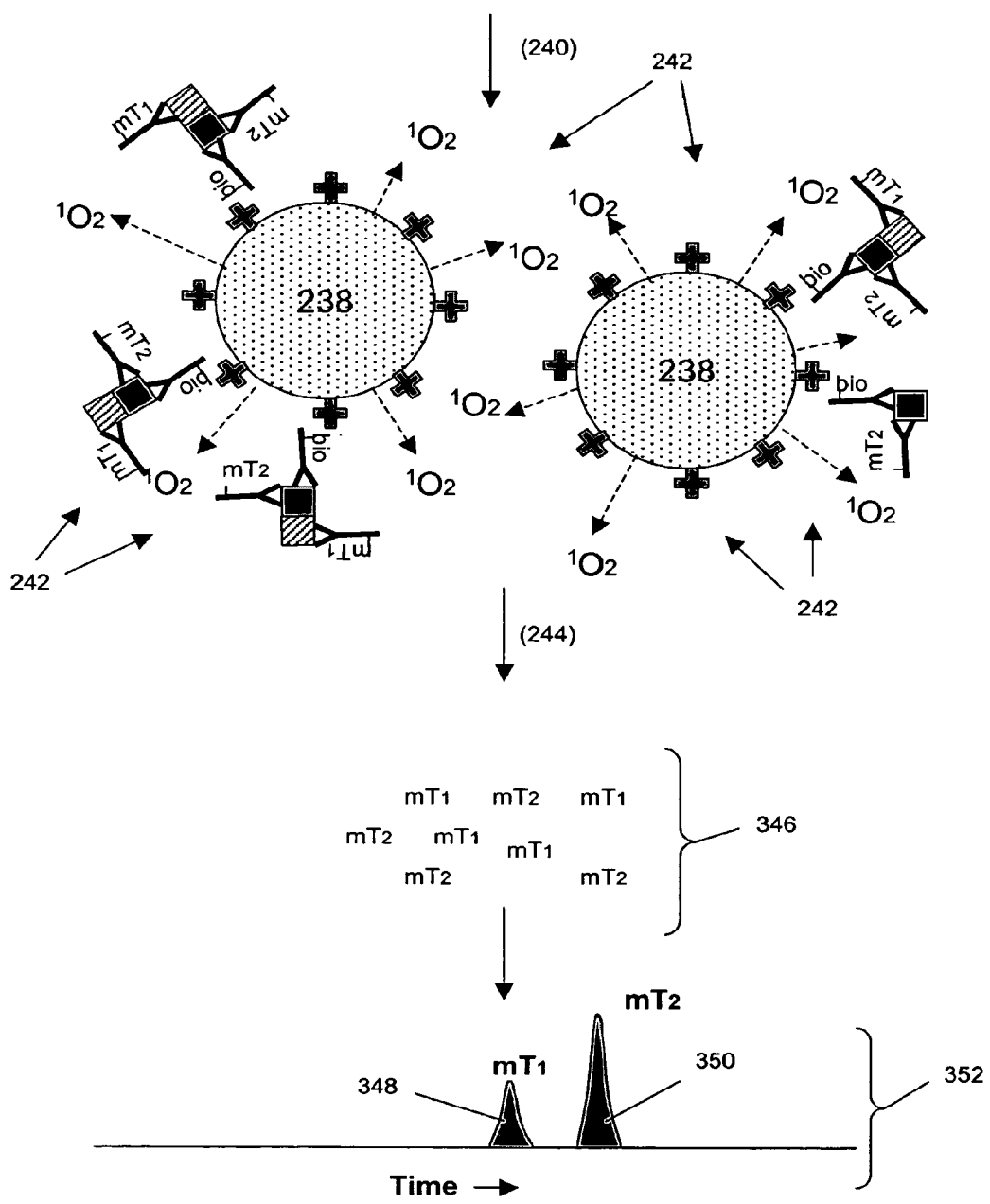

In one embodiment, a photosensitizer is incorporated into a latex particle to form photosensitizer beads, e.g. as disclosed by Pease et al., U.S. Pat. No. 5,709,994; Pollner, U.S. Pat. No. 6,346,384; and Pease et al, PCT publication WO 01/84157. Alternatively, photosensitizer beads may be prepared by covalently attaching a photosensitizer, such as rose bengal, to 0.5 micron latex beads by means of chloromethyl groups on the latex to provide an ester linking group, as described in J. Amer. Chem. Soc., 97: 3741 (1975). Use of such photosensitizer beads is illustrated in FIG. 2C, in which item labels (100)-(122) are described in FIG. 1B. Reactions may be carried out, for example, in a conventional 96-well or 384-well microtiter plate, or the like, having a filter membrane that forms one wall, e.g. the bottom, of the wells that allows reagents to be removed by the application of a vacuum. This allows the convenient exchange of buffers, if the buffer required for specific binding of binding compounds is different that the buffer required for either singlet oxygen generation or separation. For example, in the case of antibody-based binding compounds, a high salt buffer is required. If electrophoretic separation of the released tags is employed, then better performance is achieved by exchanging the buffer for one that has a lower salt concentration suitable for electrophoresis. In this embodiment, instead of attaching a photosensitizer directly to a binding compound, such as an antibody, a cleaving probe comprises two components: antibody (232) derivatized with a capture moiety, such as biotin (indicated in FIG. 2C as "bio") and photosensitizer bead (238) whose surface is derivatized with an agent (234) that specifically binds with the capture moiety, such as avidin or streptavidin. Complexes (230) are then captured (236) by photosensitizer beads by way of the capture moiety, such as streptavidin (234). Conveniently, if the pore diameter of the filter membrane is selected so that photosensitizer beads (238) cannot pass, then a buffer exchange also serves to remove unbound binding compounds, which leads to an improved signal. After an appropriate buffer for separation has been added, if necessary, photosensitizer beads (238) are illuminated (240) so that singlet oxygen is generated (242) and molecular tags are released (244). Such released molecular tags (346) are then separated to form separation profile (352) and dimers are quantified ratiometrically from peaks (348) and (350). Photosensitizer beads may be used in either homogeneous or heterogeneous assay formats.

Figure 3:
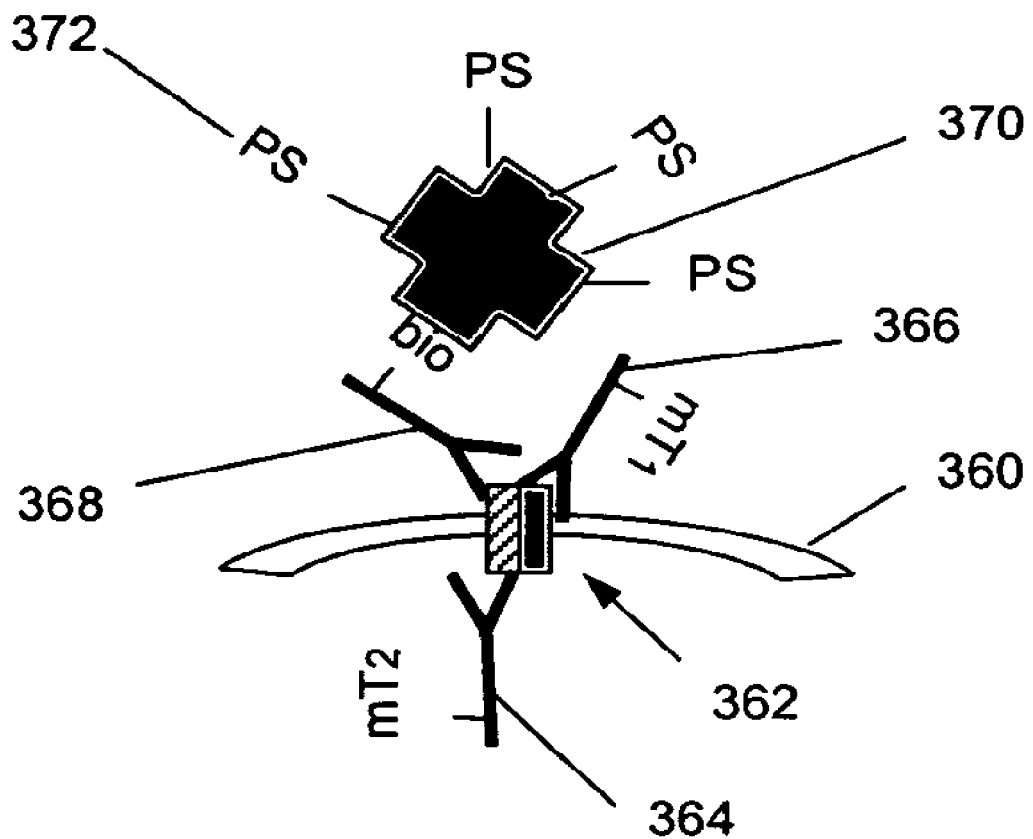
FIG. 3 illustrates the attachment of photosensitizers to antibodies.

Preferably, when analytes, such as cell surface receptors, are being detected or antigen in a fixed sample, a cleaving probe may comprise a primary haptenated antibody and a secondary anti-hapten binding protein derivatized with multiple photosensitizer molecules. A preferred primary haptenated antibody is a biotinylated antibody, and preferred secondary anti-hapten binding proteins may be either an anti-biotin antibody or streptavidin. Other combinations of such primary and secondary reagents are well known in the art, e.g. Haugland, Handbook of Fluorescent Probes and Research Reagents, Ninth Edition (Molecular Probes, Eugene, Oreg., 2002). An exemplary combination of such reagents is illustrated in FIG. 3. There binding compounds (366 and 368) having releasable tags ("$mT_1$" and "$mT_2$" in the Figure), and primary antibody (368) derivatized with biotin (369) are specifically bound to different epitopes of receptor dimer (362) in membrane (360). Biotin-specific binding protein (370), e.g. streptavidin, is attached to biotin (369) bringing multiple photosensitizers (372) into effective proximity of binding compounds (366 and 368). Biotin-specific binding protein (370) may also be an anti-biotin antibody, and photosensitizers may be attached via free amine group on the protein by conventional coupling chemistries, e.g. Hermanson (cited above). An exemplary photosensitizer for such use is an NHS ester of methylene blue prepared as disclosed in Shimadzu et al, European patent publication 0510688.

Assay Conditions

The following general discussion of methods and specific conditions and materials are by way of illustration and not limitation. One of ordinary skill in the art will understand how the methods described herein can be adapted to other applications, particularly with using different samples, cell types and target complexes.

In conducting the methods of the invention, a combination of the assay components is made, including the sample being tested, the binding compounds, and optionally the cleaving probe. Generally, assay components may be combined in any order. In certain applications, however, the order of addition may be relevant. For example, one may wish to monitor competitive binding, such as in a quantitative assay. Or one may wish to monitor the stability of an assembled complex. In such applications, reactions may be assembled in stages, and may require incubations before the complete mixture has been assembled, or before the cleaving reaction is initiated.

The amounts of each reagent are usually determined empirically. The amount of sample used in an assay will be determined by the predicted number of target complexes present and the means of separation and detection used to monitor the signal of the assay. In general, the amounts of the binding compounds and the cleaving probe are provided in molar excess relative to the expected amount of the target molecules in the sample, generally at a molar excess of at least 1.5, more desirably about 10-fold excess, or more. In specific applications, the concentration used may be higher or lower, depending on the affinity of the binding agents and the expected number of target molecules present on a single cell. Where one is determining the effect of a chemical compound on formation of oligomeric cell surface complexes, the compound may be added to the cells prior to, simultaneously with, or after addition of the probes, depending on the effect being monitored.

The assay mixture is combined and incubated under conditions that provide for binding of the probes to the cell surface molecules, usually in an aqueous medium, generally at a physiological pH (comparable to the pH at which the cells are cultures), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° to 70° C., usually from about 15° to 45° C., more usually 25° to 37°.

After assembly of the assay mixture and incubation to allow the probes to bind to cell surface molecules, the mixture is treated to activate the cleaving agent to cleave the tags from the binding compounds that are within the effective proximity of the cleaving agent, releasing the corresponding tag from the cell surface into solution. The nature of this treatment will depend on the mechanism of action of the cleaving agent. For example, where a photosensitizer is employed as the cleaving agent, activation of cleavage will comprise irradiation of the mixture at the wavelength of light appropriate to the particular sensitizer used.

Following cleavage, the sample is then analyzed to determine the identity of tags that have been released. Where an assay employing a plurality of binding compounds is employed, separation of the released tags will generally precede their detection. The methods for both separation and detection are determined in the process of designing the tags for the assay. A preferred mode of separation employs electrophoresis, in which the various tags are separated based on known differences in their electrophoretic mobilities.

As mentioned above, in some embodiments, if the assay reaction conditions may interfere with the separation technique employed, it may be necessary to remove, or exchange, the assay reaction buffer prior to cleavage and separation of the molecular tags. For example, assay conditions may include salt concentrations (e.g. required for specific binding) that degrade separation performance when molecular tags are separated on the basis of electrophoretic mobility. Thus, such high salt buffers may be removed, e.g. prior to cleavage of molecular tags, and replaced with another buffer suitable for electrophoretic separation through filtration, aspiration, dilution, or other means.

EXAMPLES

Sources of Materials Used in Examples

Antibodies specific for Her receptors, adaptor molecules, and normalization standards are obtained from commercial vendors, including Labvision, Cell Signaling Technology, and BD Biosciences. All cell lines were purchased from ATCC. All human snap-frozen tissue samples were purchased from either William Bainbridge Genome Foundation (Seattle, Wash.) or Bio Research Support (Boca Raton, Fla.) and were approved by Institutional Research Board (IRB) at the supplier.

The molecular tag-antibody conjugates used below are formed by reacting NHS esters of the molecular tag with a free amine on the indicated antibody using conventional procedures. Molecular tags, identified below by their "Pro_N" designations, are disclosed in the following references: Singh et al, U.S. patent publications, 2003/017915 and 2002/0013126, which are incorporated by reference. Briefly, binding compounds below are molecular tag-monoclonal antibody conjugates formed by reacting an NHS ester of a molecular tag with free amines of the antibodies in a conventional reaction.

Example 1

Simultaneous Measurement of Her2-Her3 Heterodimerization and Erk1 Phosphorylation In this example, an assay is described for providing a ratiometric measure of phosphorylated Erk1 and Her2-Her3 heterodimerization. The assays are carried out as follows.

Sample Preparation:
1. Serum-starve breast cancer cell line culture (MCF-7) overnight before use.
2. Stimulate cell lines with HRG in culture media for 10 minutes at 37° C. Exemplary doses of HRG are 0, 0.032, 0.16, 0.8, 4, 20, 100 nM for MCF-7 cells.
3. Aspirate culture media, transfer onto ice, and add lysis buffer (described below) to lyse cells in situ.
4. Scrape and transfer lysate to microfuge tube. Incubate on ice for 30 min. Microfuge at 14,000 rpm, 4° C., for 10 min.
5. Collect supernatants as lysates and aliquot for storage at −80° C. until use.

Lysis Buffer (Made Fresh and Stored on Ice):

| Final | ul | Stock |
|---|---|---|
| 1% Triton X-100 | 1000 | 10% |
| 20 mM Tris-HCl (pH 7.5) | 200 | 1 M |
| 100 mM NaCl | 200 | 5 M |
| 50 mM NaF | 500 | 1 M |
| 50 mM Na beta-glycerophosphate | 1000 | 0.5 M |
| 1 mM $Na_3 VO_4$ | 100 | 0.1 M |
| 5 mM EDTA | 100 | 0.5 M |
| 10 ug/ml pepstatin | 100 | 1 mg/ml |
| 1 tablet (per 10 ml) Roche Complete protease inhibitor (#1836170) | N/A | N/A |
| Water | 6500 | N/A |
| | 10 ml | Total |

The total assay volume is 40 ul. The lysate volume is adjusted to 10 ul with lysis buffer. The antibodies are diluted in lysis buffer up to 20 ul. Typically ~5000 to 500,000 cell-equivalent of lysates is used per reaction.

Procedure: Working concentrations of pre-mixed antibodies prior to adding into reaction:
- eTag1_anti-Erk1 (epitope 1) at 10 nM
- eTag2_anti-phospho-Erk1 at 10 nM
- Biotin_anti-Erk1 (epitope 2) at 20 nM
- eTag3_anti-Her2 at 10 nM
- eTag4_anti-phospho-Her2
- Biotin_anti-Her3 at 20 nM
- Universal Standard US-1 at 700 nM
- [The Universal Standard US-1 is BSA conjugated with biotin and molecular tag Pro8, which is used to normalize the amount of streptavidin-photosensitizer beads in an assay].
- The molecular tags are attached directly to antibodies by reacting an NHS-ester of a molecular tag precursor (see FIGS. 15A-15J in U.S. patent publication 2003/0013126 A1, which is incorporated herein by reference) with free amines on the antibodies using conventional techniques, e.g. Hermanson (cited above).
1. To assay 96-well filter plate (Millipore MAGVN2250), add 20 ul antibody mix to 10 ul lysate and incubate for 1 hour at 4° C.
2. Add 10 ul streptavidin-derivatized cleaving probe (final 4 ug/well) to assay well and incubate for 40 min.
3. Add 200 ul wash buffer and apply vacuum to empty.
4. Add 30 ul illumination buffer and illuminate.
5. Transfer 10 ul of each reaction to CE assay plate for analysis.

Data Analysis:
1. Normalize relative fluorescence units (RFU) signal of each molecular tag against that of internal Universal Standard US-1.
2. Subtract RFU of "no lysate" background control from corresponding normalized eTag reporter signals.

Example 2

Analysis of Cell Lysates for Her-2 Heterodimerization and Receptor Phosphorylation In this example, Her1-Her2 and Her2-Her3 heterodimers and phosphorylation states are measured in cell lysates from several cell lines after treatment with various concentrations of epidermal growth factor (EGF) and heregulin (HRG). Measurements are made using three binding compounds and a cleaving probe as described below.

Sample Preparation:
1. Serum-starve breast cancer cell line culture overnight before use.
2. Stimulate cell lines with EGF and/or HRG in culture media for 10 minutes at 37° C. Exemplary doses of EGF/HRG are 0, 0.032, 0.16, 0.8, 4, 20, 100 nM for all cell lines (e.g. MCF-7, T47D, SKBR-3) except BT20 for which the maximal dose is increased to 500 nM because saturation is not achieved with 100 nM EGF.
3. Aspirate culture media, transfer onto ice, and add lysis buffer to lyse cells in situ.
4. Scrape and transfer lysate to microfuge tube. Incubate on ice for 30 min. Microfuge at 14,000 rpm, 4° C., for 10 min. (Centrifugation is optional.)
5. Collect supernatants as lysates and aliquot for storage at −80° C. until use.

Assay:
Assay design: As illustrated diagrammatically in FIG. 4A, Her2-Her3 heterodimers (900) are quantified ratiometrically based on the binding of cleaving probe (902) and binding compounds (904), (906), and (908). A photosensitizer indicated by "PS" is attached to cleaving probe (902) via an avidin-biotin linkage, and binding compounds (904), (906), and (908) are labeled with molecular tags Pro14, Pro10, and Pro11, respectively. Binding compound (904) is specific for a phosphorylation site on Her3.

The total assay volume is 40 ul. The lysate volume is adjusted to 30 ul with lysis buffer. The antibodies are diluted in lysis buffer up to 10 ul. Typically ~5000 to 15000 cell-equivalent of lysates is used per reaction. The detection limit is ~1000 cell-equivalent of lysates.

Procedure: Final concentrations of pre-mixed binding compounds (i.e. molecular tag- or biotin-antibody conjugates) in reaction:
- Pro4_anti-Her-2: 0.1 ug/ml
- Pro10_anti-Her-1: 0.05-0.1 ug/ml
- Pro11_anti-Her-3: 0.1 ug/ml
- Pro2_anti-phospho-Tyr: 0.1 ug/ml
- Biotin_anti-Her-2: 1-2 ug/ml 6. To assay 96-well, add 10 ul antibody mix to 30 ul lysate and incubate for 1 hour at RT.
7. Add 2 ul streptavidin-derivatized cleaving probe (final 2 ug/well) to assay well and incubate for 45 min.
8. Add 150 ul of PBS with 1% BSA to 96-well filter plate (Millipore MAGVN2250) and incubate for 1 hr at RT for blocking.
9. Empty filter plate by vacuum suction. Transfer assay reactions to filter plate and apply vacuum to empty.
10. Add 200 ul wash buffer and apply vacuum to empty. Repeat one time.
11. Add 200 ul illumination buffer and apply vacuum to empty. Repeat one time.
12. Add 30 ul illumination buffer and illuminate for 20 min.
13. Transfer 10 ul of each reaction to CE assay plate for analysis using an ABI3100 CE instrument with a 22 cm capillary (injection conditions: 5 kV, 75 sec, 30° C.; run conditions: 600 sec, 30° C.).

Assay Buffers are as Follows:
Lysis Buffer (Made Fresh and Stored on Ice)

| Final | ul | Stock |
|---|---|---|
| 1% Triton X-100 | 1000 | 10% |
| 20 mM Tris-HCl (pH 7.5) | 200 | 1 M |
| 100 mM NaCl | 200 | 5 M |
| 50 mM NaF | 500 | 1 M |
| 50 mM Na beta-glycerophosphate | 1000 | 0.5 M |
| 1 mM $Na_3 VO_4$ | 100 | 0.1 M |
| 5 mM EDTA | 100 | 0.5 M |
| 10 ug/ml pepstatin | 100 | 1 mg/ml |
| 1 tablet (per 10 ml) Roche Complete protease inhibitor (#1836170) | N/A | N/A |
| Water | 6500 | N/A |
| | 10 ml | Total |

Wash Buffer (Stored at 4° C.)

| Final | ml | Stock |
|---|---|---|
| 1% NP-40 | 50 | 10% |
| 1x PBS | 50 | 10x |
| 150 mM NaCl | 15 | 5 M |
| 5 mM EDTA | 5 | 0.5 M |
| Water | 380 | N/A |
| | 500 ml | Total |

Illumination Buffer:

| Final | ul | Stock |
|---|---|---|
| 0.005x PBS | 50 | 1x |
| CE std | 3 | 100x |
| 10 mM Tris-HCl (pH 8.0) | | 0.1M |
| 10 pM A160 | | 1 nM |
| 10 pM A315 | | 1 nM |
| 10 pM HABA | | 1 nM |
| Water | 10,000 | NA |
| | 10 ml | Total |

Data Analysis:
3. Normalize relative fluorescence units (RFU) signal of each molecular tag against CE reference standard A315 (a fluorescein-derivatized deoxyadenosine monophosphate that has known peak position relative to molecular tags from the assay upon electrophoretic separation).
4. Subtract RFU of "no lysate" background control from corresponding molecular tag signals.
5. Report heterodimerization for Her-1 or Her-3 as the corresponding RFU ratiometric to RFU from Pro4_anti-Her-2 from assay wells using biotin-anti-Her-2.
6. Report receptor phosphorylation for Her-1,2,3 as RFU from Pro2_PT100 anti-phospho-Tyr ratiometric to RFU from Pro4_anti-Her-2 from assay wells using biotin-anti-Her-2.

Figure 4A:
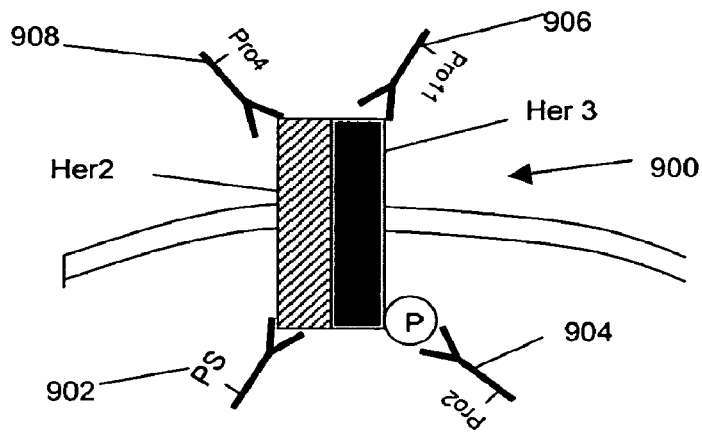
FIGS. 4A-4E illustrate data from assays on SKBR-3 and BT-20 cell lysates for receptor heterodimers using a method of the invention.
Figure 4B:
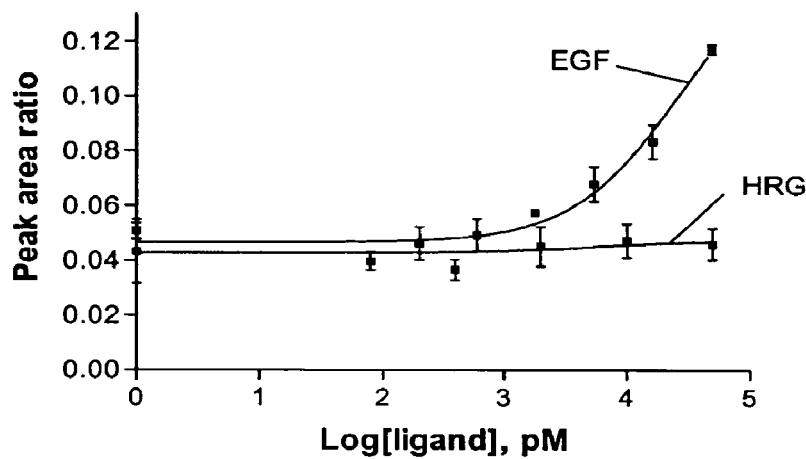
Figure 4C:
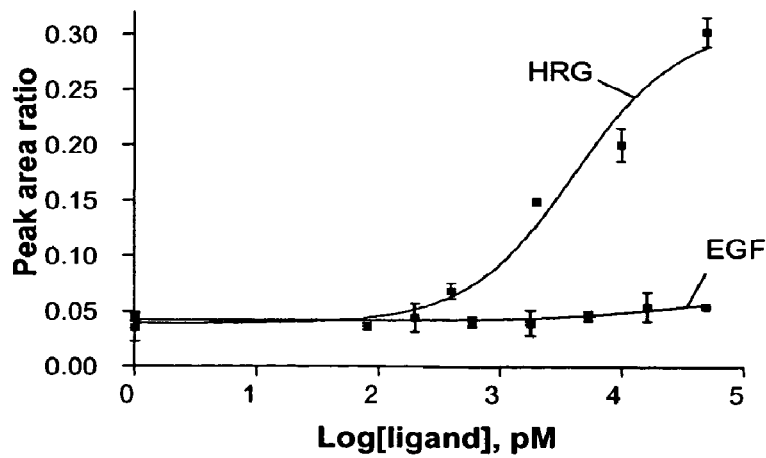
Figure 4D:
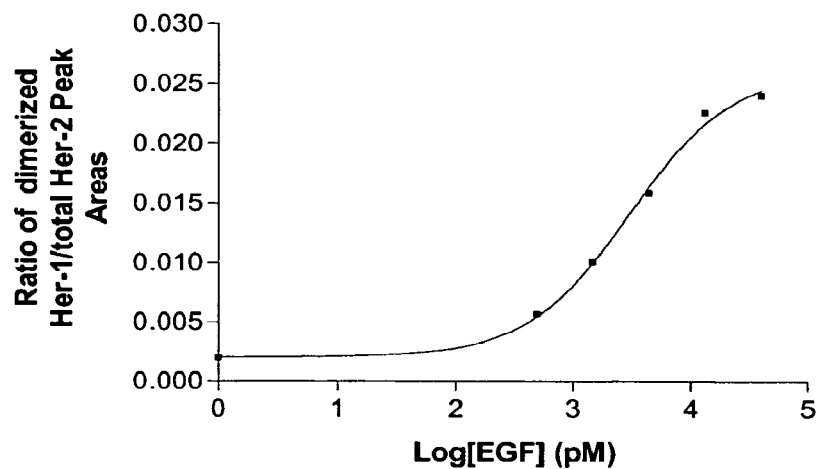
Figure 4E:
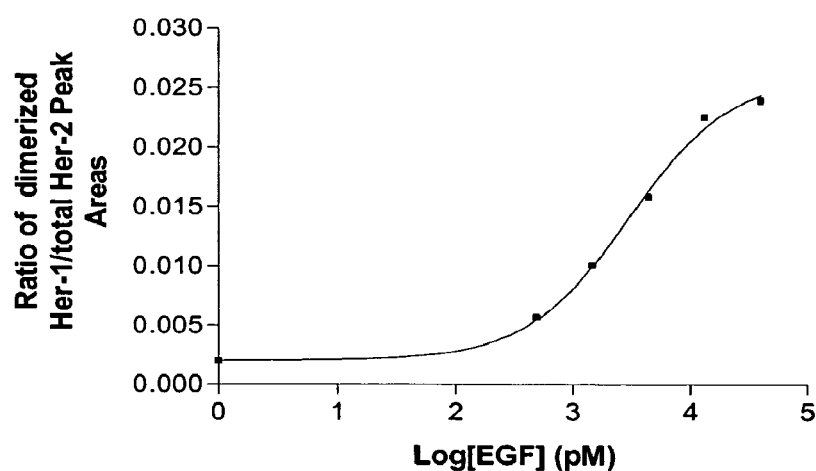

Results of the assays are illustrated in FIGS. 4B-4H. FIG. 4B shows the quantity of Her1-Her2 heterodimers increases on MCF-7 cells with increasing concentrations of EGF, while the quantity of the same dimer show essentially no change with increasing concentrations of HRG. FIG. 4C shows the opposite result for Her2-Her3 heterodimers. That is, the quantity of Her2-Her3 heterodimers increases on MCF-7 cells with increasing concentrations of HRG, while the quantity of the same dimer show essentially no change with increasing concentrations of EGF. FIGS. 4D and 4E show the quantity of Her1-Her2 heterodimers increases on SKBR-3 cells and BT-20 cells, respectively, with increasing concentrations of EGF.

Example 3

Analysis of Tissue Lysates for Her2 Heterodimerization and Receptor Phosphorylation In this example, Her1-Her2 and Her2-Her3 heterodimers and phosphorylation states are measured in tissue lysates from human breast cancer specimens.

Sample Preparation:
1. Snap frozen tissues are mechanically disrupted at the frozen state by cutting.
2. Transfer tissues to microfuge tube and add 3× tissue volumes of lysis buffer (from appendix I) followed by vortexing to disperse tissues in buffer.
3. Incubate on ice for 30 min with intermittent vortexing to mix.
4. Centrifuge at 14,000 rpm, 4° C., for 20 min.
5. Collect supernatants as lysates and determine total protein concentration with BCA assay (Pierce) using a small aliquot.
6. Aliquot the rest for storage at −80° C. until use.

Assay Design:
1. The total assay volume is 40 ul.
2. The lysates are tested in serial titration series of 40, 20, 10, 5, 2.5, 1.25, 0.63, 0.31 ug total-equivalents and the volume is adjusted to 30 ul with lysis buffer. Data from the titration series confirm the specificity of the dimerization or phosphorylation signals.
3. A universal antibody mix comprising all eTag-antibodies diluted in lysis buffer is used at the following concentrations.
4. Individual biotin-antibody for each receptor is added separately to the reactions.
5. Three eTag assays are conducted with each tissue lysate, each using a different biotin-antibody corresponding to specific receptor dimerization to be measured.
6. Expression level of each receptor is determined from different assay containing the biotin-antibody specific to the receptor.
7. Dimerization and phosphorylation signals are determined ratiometrically only in the assay containing the biotin-anti-Her-2.

Assay controls: MCF-10A and MCF-7 cell lines are used as qualitative negative and positive controls, respectively. Cell lines are either unstimulated or stimulated with 100 nM EGF or 100 nM HRG. Lysis buffer is included as a background control when replacing the tissue samples.

Final Concentrations of Pre-Mixed Antibodies in Reactions:
Universal Antibody Mix:
  Pro4_anti-Her-2: 0.1 ug/ml
  Pro10_anti-Her-1: 0.05 ug/ml
  Pro11_anti-Her-3: 0.1 ug/ml
  Pro2_anti-phospho-Tyr: 0.01 ug/ml
Individual Biotin Antibody:
  Biotin_anti-Her-1: 2 ug/ml
  Biotin_anti-Her-2: 2 ug/ml
  Biotin_anti-Her-3: 2 ug/ml Procedure:
1. Prepare antibody reaction mix by adding biotin antibody to universal antibody mix.
2. To assay 96-well, add 10 ul universal reaction mix to 30 ul lysate and incubate for 1 hour at RT.
3. Add 2 ul streptavidin-derivatized cleaving probe (final 2 ug/well) to assay well and incubate for 45 min.
4. Add 150 ul of PBS with 1% BSA to 96-well filter plate (Millipore MAGVN2250) and incubate for 1 hr at RT for blocking.
5. Empty filter plate by vacuum suction. Transfer assay reactions to filter plate and apply vacuum to empty.
6. Add 200 ul wash buffer and apply vacuum to empty. Repeat one time.
7. Add 200 ul illumination buffer and apply vacuum to empty. Repeat one time.
8. Add 30 ul illumination buffer and illuminate for 20 min.
9. Transfer 10 ul of each reaction to CE assay plate for analysis using ABI3100 capillary electrophoresis instrument with a 22 cm capillary (injection conditions: 5 kV, 75 sec, 30° C.; run conditions: 600 sec, 30° C.)

Data Analysis:
1. Normalize RFU signal of each molecular tag against CE reference standard A315.
2. Determine the cut-off values of RFU (each for dimerization or phosphorylation) below which ratios are not calculated because the signals are too low to be reliable. Below the cut-off values, the RFU signals are not titratable in the series of lysate dilution tested. The values can be determined with a large set of normal tissues where dimerization and phosphorylation signals are expected to be absent or at the lowest. These values also represent the basal level of dimerization or phosphorylation on the normal tissues to which tumor tissues will be compared.
3. For the minority of normal tissues, if present, with RFU values above the cut-off, determine the individual RFU level and ratiometric readouts of Her-1 or Her-3 heterodimerization or phosphorylation peaks detected. These samples represent outliers that should be used as matched donor controls for the corresponding tumor tissue samples while scoring.
4. For all tumor samples showing titratable RFU signals, use the lowest signal of each of Her-1, Her-2, Her-3, or phosphorylation from the tissue lysate titration series as the background. Subtract this background from the molecular tag signals of the high dose lysates (e.g. 40 ug) to yield the specific RFU signals. If there is no signal dose response in the titration series, all signals (which are usually very low) are considered background and no specific signals can be used for ratiometric analysis.
5. Report heterodimerization for Her-1 or Her-3 as the corresponding specific RFU ratiometric to the specific RFU from Pro4_anti-Her-2. If no specific RFU is obtained, the dimerization is negative.
6. Report receptor phosphorylation for Her-1,2,3 as specific RFU from Pro2_anti-phospho-Tyr ratiometric to the specific RFU from Pro4_anti-Her-2. If no specific RFU is obtained, the phosphorylation is negative.

Figure 5A:
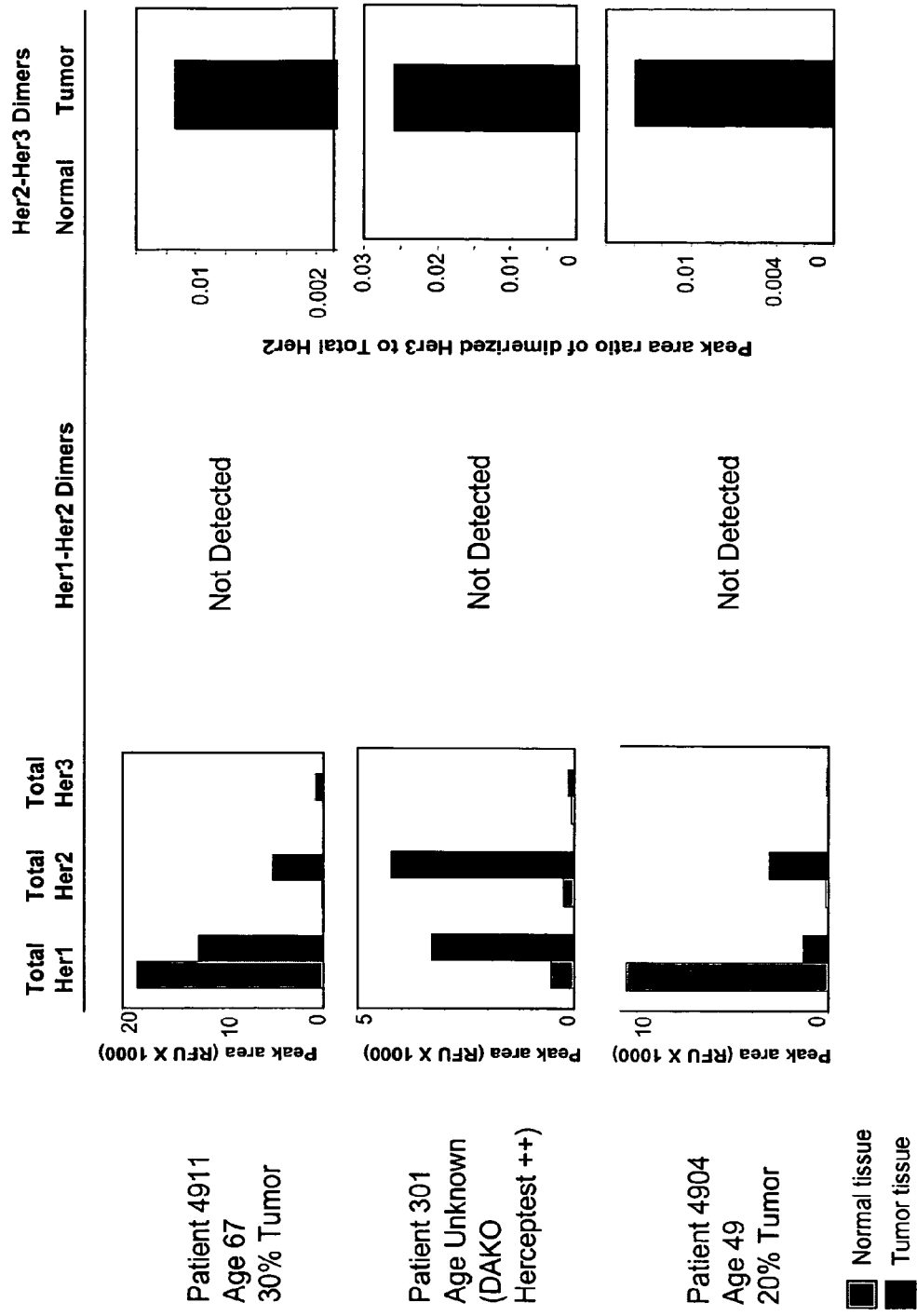
FIGS. 5A-5C illustrate data from assays for receptor heterodimers on human normal and tumor breast tissue samples using a method of the invention.
Figure 5B:
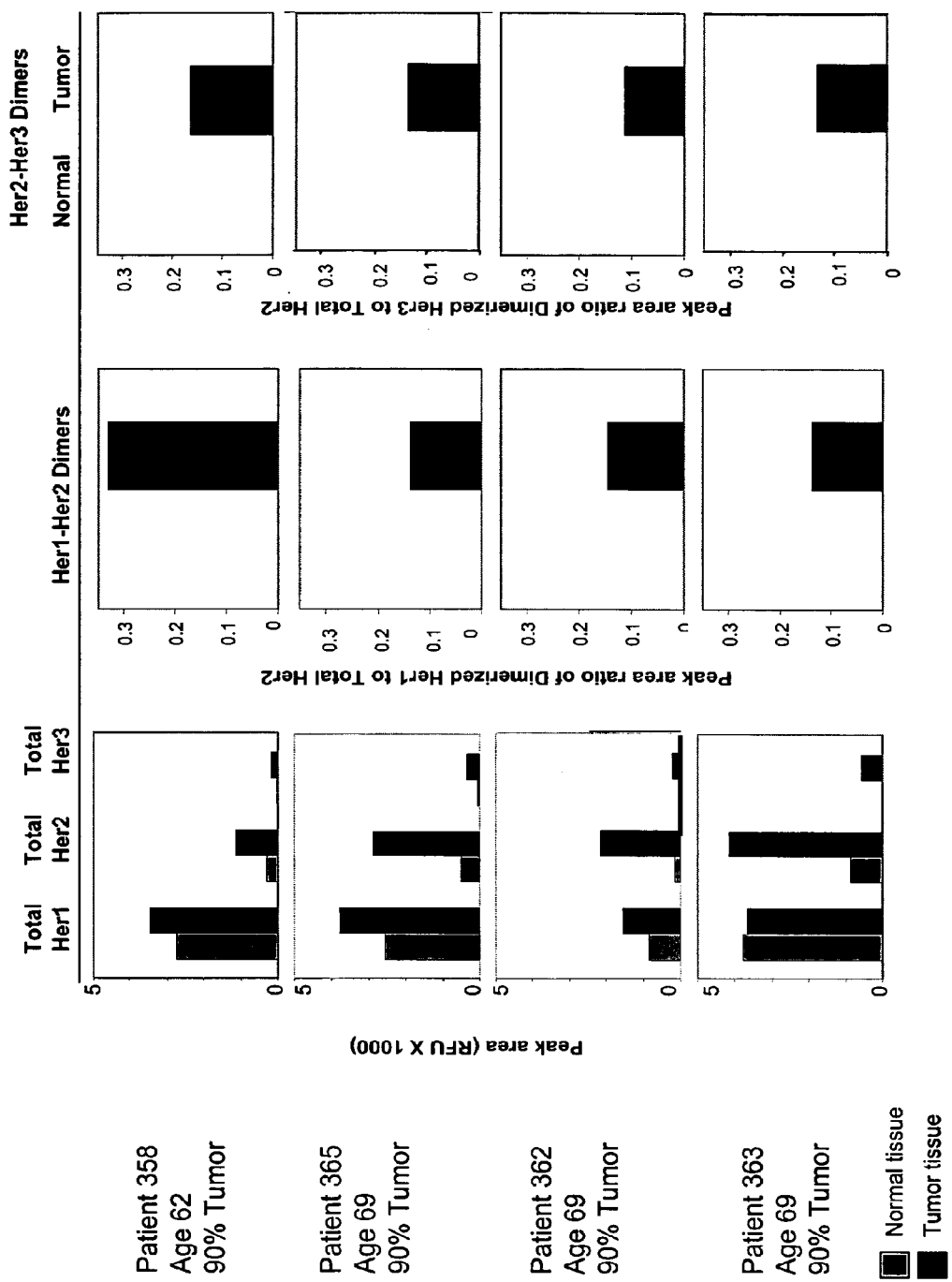
Figure 5C:
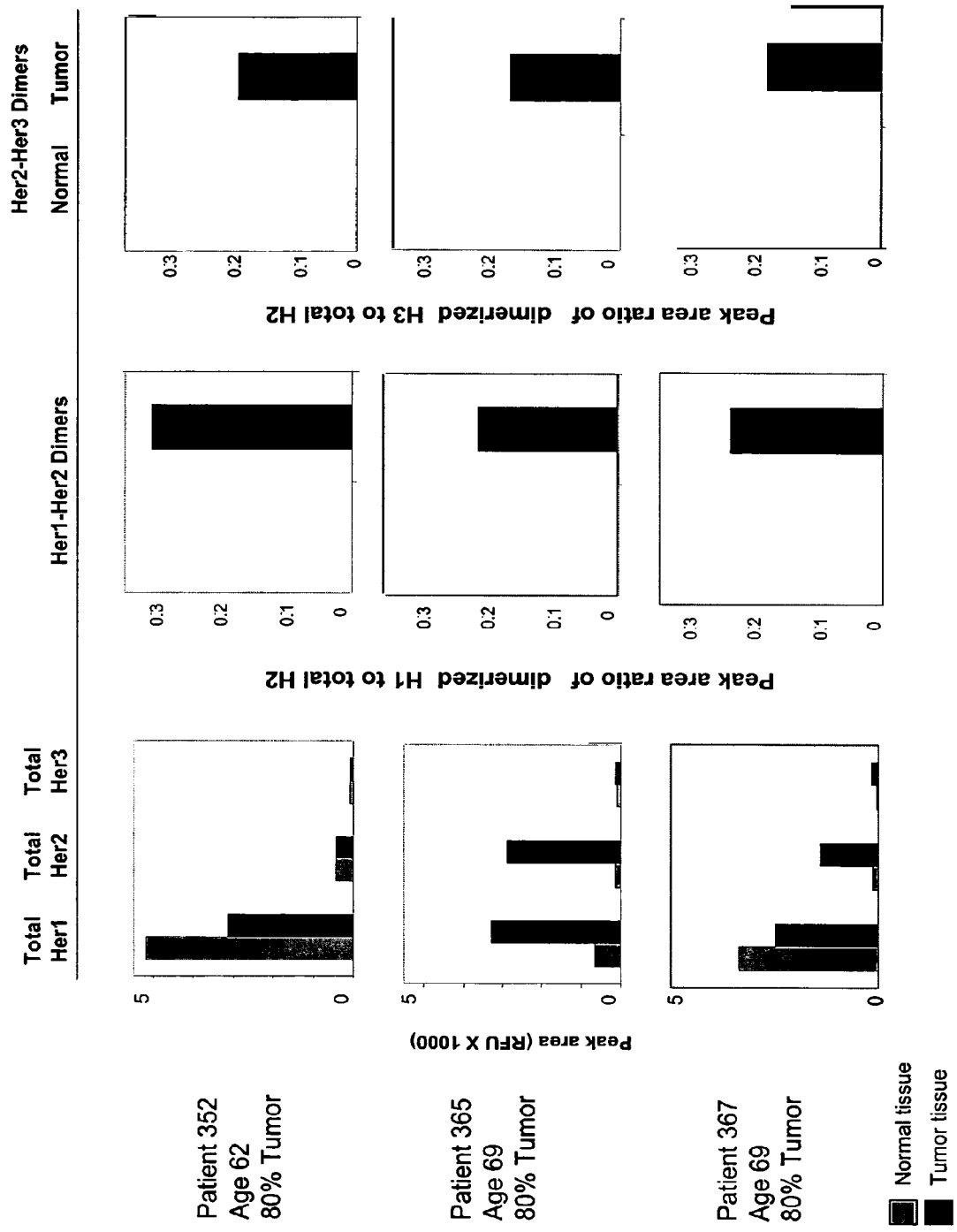

In FIGS. 5A-5C data shown are representative of multiple patients' breast tissue samples tested with assays of the invention. The clinical Her-2 status from immunohistochemistry (DAKO Herceptest) of 9 out of 10 tumor samples was negative, indicative of either undetectable Her-2 staining, or staining of less than 10% of the tumor cells, or a faint and barely perceptible staining on part of the cell membrane of more than 10% tumor cells. The assays of the invention determined the expression of Her-1, Her-2, and Her-3 on both normal and tumor tissues. The heterodimerization of Her1 and the Her2 and of Her2 and Her3 was detected only in tumor tissues but not in any normal tissues.

Example 4

Analysis of Cell Lysates for Her1 or Her2 Homodimerization and Receptor Phosphorylation Sample preparation was carried out essentially as described in Example 2. Her1 homodimerization was induced by treating the cell lines with EGF or TGFα. For homodimerization of Her2 which does not have a ligand, unstimulated SKBR-3 or MDA-MD-453 cells that overexpress Her2 are compared to unstimulated MCF-7 cells that express a low level of Her2.

Assay design: A monoclonal antibody specific to the receptor is separately conjugated with either a molecular tag or biotin (that is then linked to a photosensitizer via an avidin bridge), so that the cleaving probe and a binding compound compete to bind to the same epitope in this example. Another binding compound is used that consists of a second antibody recognizing an overlapping epitope on the receptor, so that a ratiometric signal can be generated as a measure of homodimerization. The signal derived from the second antibody also provides a measure of the total amount of receptor in a sample. The total amount of receptor is determined in a separate assay well. Receptor phosphorylation can be quantified together with either homodimerization or total receptor amount.

Procedure: The assay volume is 40 ul and the general procedure is similar to that of Example 2. Two assay wells, A and B, are set up for each sample to quantify homodimerization and total amount of receptor separately.
For Quantification of Her1-Her1 Homodimers:
Final Concentrations in Antibody Mix in Assay Well A:
  Pro 12_anti-Her-1: 0.05-0.1 ug/ml
  Biotin_anti-Her-1: 1-2 ug/ml
Final Concentrations in Antibody Mix in Assay Well B:
  Pro10_anti-Her-1: 0.05-0.1 ug/ml
  Pro2_anti-phospho-Tyr: 0.1 ug/ml
  Biotin_anti-Her-1: 1-2 ug/ml
For Quantification of Her2-Her2 Homodimers:
Final Concentrations in Antibody Mix in Assay Well A:
  Pro4_anti-Her-1: 0.05-0.1 ug/ml
  Biotin_anti-Her-1: 1-2 ug/ml
Final Concentrations in Antibody Mix in Assay Well B:
  Pro4_anti-Her-1: 0.05-0.1 ug/ml
  Pro2_anti-phospho-Tyr: 0.1 ug/ml
  Biotin_anti-Her-1: 1-2 ug/ml
Data Analysis:
  1. Normalize RFU signal of each molecular tag against CE reference standard A315.
  2. Subtract RFU of "no lysate" background control from corresponding molecular tag signals.
  3. Report homodimerization for Her-1 or Her-2 as the corresponding normalized RFU from assay well A as ratiometric to normalized RFU of total receptor amount from the corresponding assay well B.
  4. Report receptor phosphorylation for Her-1 or Her-2 homodimer as normalized RFU from Pro2_PT 100 anti-phospho-Tyr from assay well B as ratiometric to normalized RFU from total receptor amount from the same assay well B.

Figure 6A:
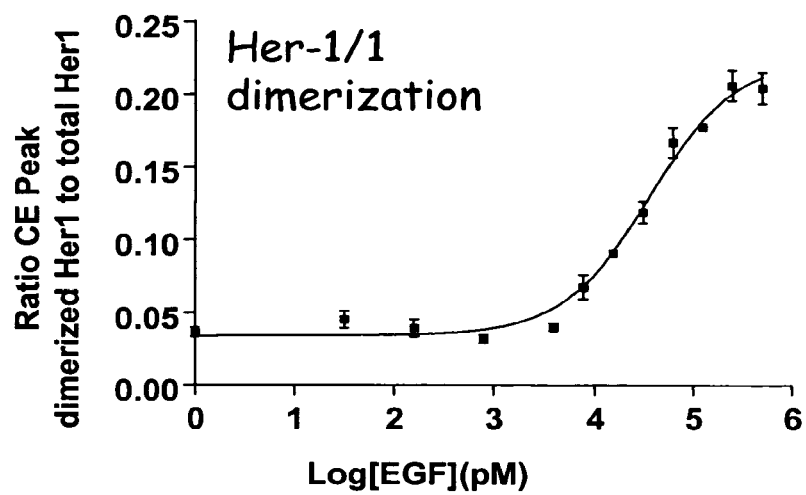
FIGS. 6A and 6B illustrate data from assays of the invention for detecting homodimers and phosphorylation of Her1 in lysates of BT-20 cells.
Figure 6B:
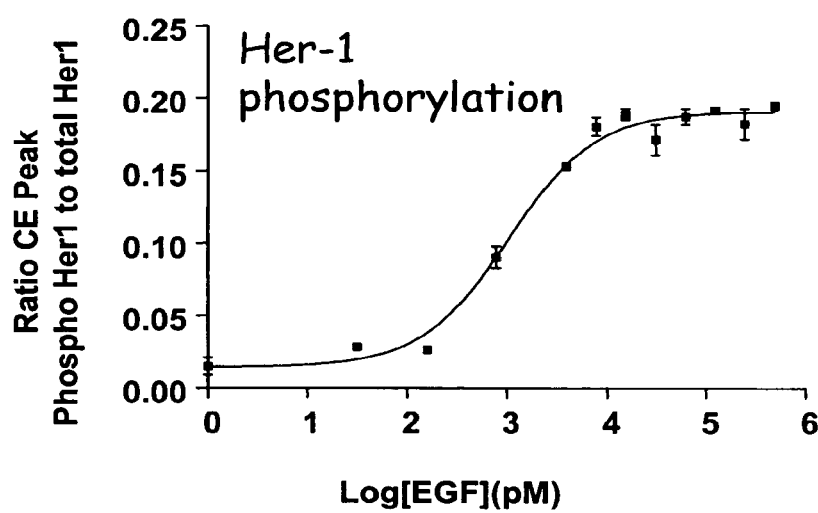
Figure 7:
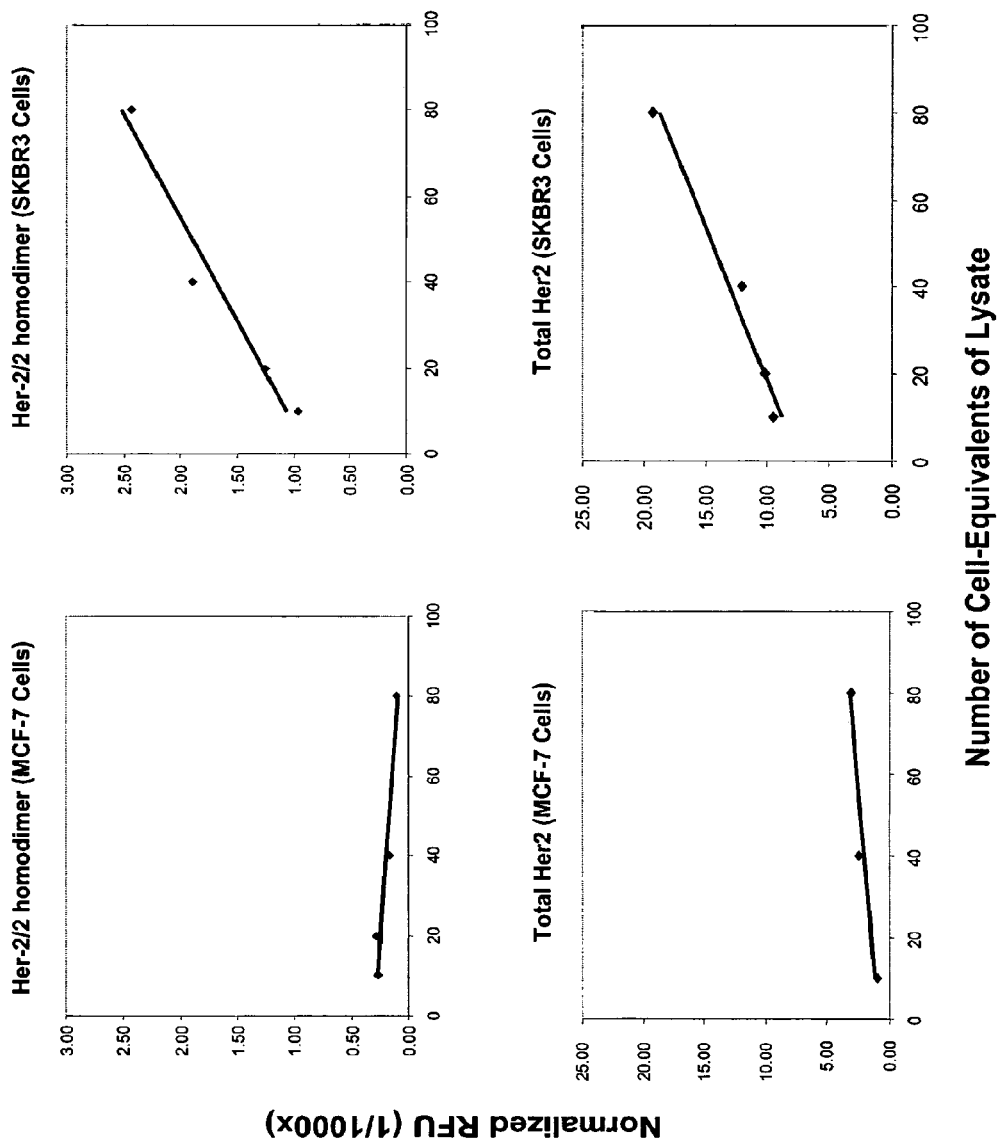
FIG. 7 shows data from assays of the invention that show Her2 homodimer populations on MCF-7 and SKBR-3 cell lines.

Results of the assays are illustrated in FIGS. 6A-6B and FIG. 7. FIG. 6A shows that the quantity of Her1-Her1 homodimers on BT-20 cells increases with increasing concentration of EGF. FIG. 6B shows that the quantity of Her1 phosphorylation in BT-20 cells increases with increasing EGF concentration. The detection of Her2-Her2 homodimers was demonstrated by comparison of signals from SKBR-3 cells expressing Her2 with signals from MCF-7 cells that express reduced level of Her2 on the cell surface. As shown in the charts of FIG. 7, no specific titratable Her2-Her2 homodimer signals were detected with MCF-7 cells whereas Her2-Her2 homodimer signals from SKBR-3 cells were clearly above the signals from MCF-7 cells Example 5

Analysis of Cell Lysates for Her1-Her3 Heterodimerization and Receptor Phosphorylation Samples are Prepared as Follows:
  1. Serum-starve breast cancer cell line culture overnight before use.
  2. Stimulate cell lines with HRG in culture media for 10 minutes at 37° C. Exemplary doses of HRG are 0, 0.032, 0.16, 0.8, 4, 20, 100 nM for T47D cells.
  3. Aspirate culture media, transfer onto ice, and add lysis buffer to lyse cells in situ.
  4. Scrape and transfer lysate to microfuge tube. Incubate on ice for 30 min. Microfuge at 14,000 rpm, 4° C., for 10 min. (Centrifugation is optional.)
  5. Collect supernatants as lysates and aliquot for storage at −80° C. until use.

Assay design: The total assay volume is 40 ul. The lysate volume is adjusted to 30 ul with lysis buffer. The antibodies are diluted in lysis buffer up to 5 ul. Typically ~5000 to 50000 cell-equivalent of lysates is used per reaction. Final concentrations of pre-mixed antibodies in reaction:
Pro10_anti-Her-1: 0.05-0.1 ug/ml
Pro11_anti-Her-3: 0.1 ug/ml
Pro2_anti-phospho-Tyr: 0.1 ug/ml
Biotin_anti-Her-3: 1-2 ug/ml
1. To assay 96-well, add 5 ul antibody mix to 30 ul lysate and incubate for 1 hour at RT.
2. Add 5 ul streptavidin-derivatized molecular scissor (final 4 ug/well) to assay well and incubate for 45 min.
3. Add 150 ul of PBS with 1% BSA to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 Min.
8. Transfer 10 ul of each reaction to CE assay plate for analysis using ABI3100 capillary electrophoresis instrument with a 22 cm capillary (injection conditions: 5 kV, 425 sec, 30° C.; run conditions: 600 sec, 30° C.).

Data Analysis:
1. Normalize RFU signal of each eTag reporter against CE reference standard A315.
2. Subtract RFU of "no lysate" background control from corresponding eTag reporter signals.
3. Report heterodimerization as the Her-1 derived Pro10 RFU ratiometric to Pro11 RFU from anti-Her-3.
4. Report receptor phosphorylation for Her-1/3 as RFU from Pro2_PT100 anti-phospho-Tyr ratiometric to RFU from Pro11_anti-Her-3 from assay wells using biotin-anti-Her-3.

Figures 8A, 8B:
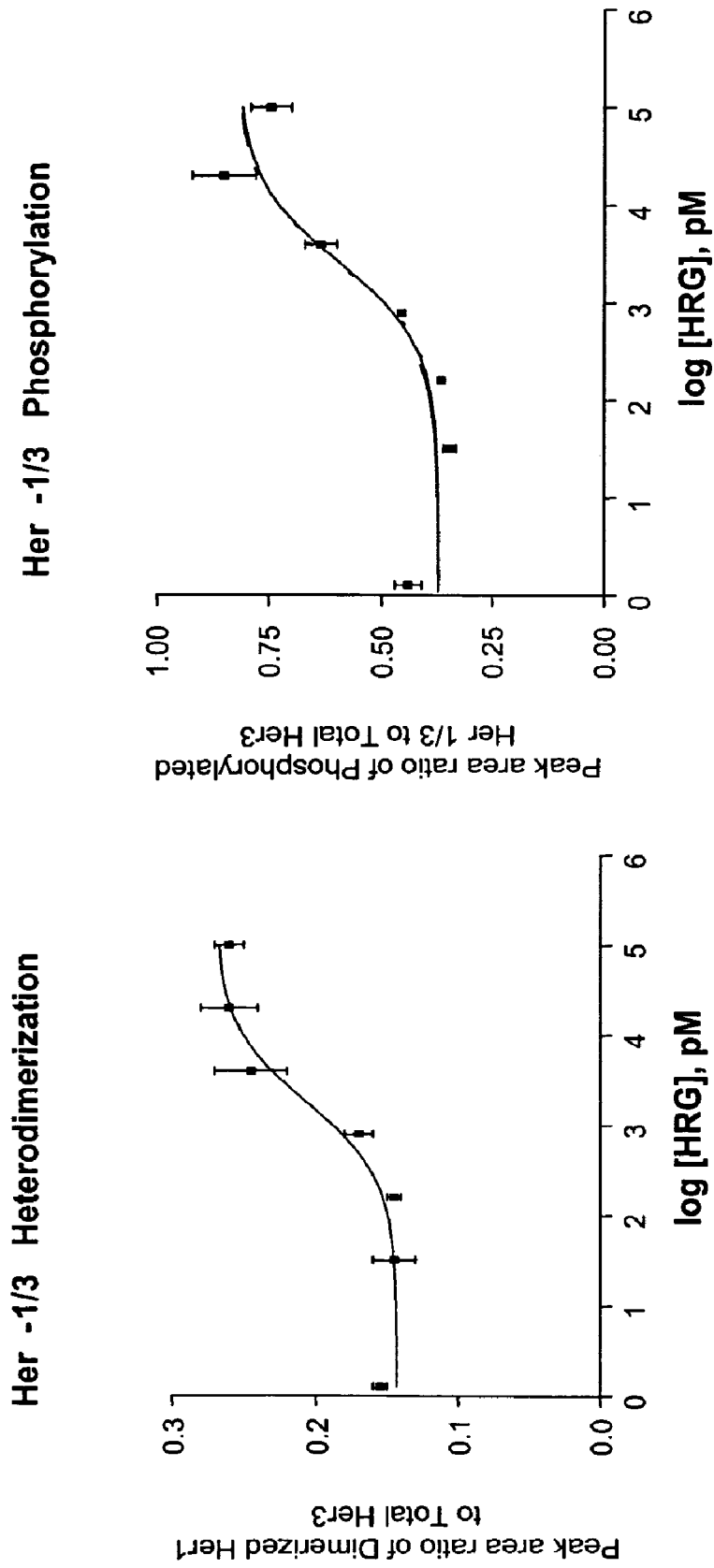
FIGS. 8A-8B show data from assays of the invention that detect heterodimers of Her1 and Her3 on cells in response to increasing concentrations of heregulin (HRG).

Results of the assay are illustrated in FIGS. 8A and 8B. The data show that both Her1-Her3 heterodimerization and dimer phosphorylation increase with increasing concentrations of HRG.

Example 6

Increase in Her1-Her3 Receptor Dimer Expression in Cancer Cell Lines in Response to Increase in Epidermal Growth Factor In this example, Her1-Her3 heterodimers are measured in cell lysates from cancer cell lines 22Rv1 and A549 after treatment with various concentrations of epidermal growth factor (EGF). Measurements are made using three binding compounds and a cleaving probe as described below.

Sample Preparation:
1. Serum-starve breast cancer cell line culture overnight before use.
2. Stimulate cell lines with EGF in culture media for 10 minutes at 37° C. Exemplary doses of EGF applied to both cell lines varied between 0-100 nM.
3. Aspirate culture media, transfer onto ice, and add lysis buffer to lyse cells in situ.
4. Scrape and transfer lysate to microfuge tube. Incubate on ice for 30 min. Microfuge at 14,000 rpm, 4° C., for 10 min. (Centrifugation is optional.) Determine protein concentration.
5. Collect supernatants as lysates and aliquot for storage at −80° C. until use.

The assay design is essentially the same as illustrated in FIG. 4A, with the following exceptions: binding compounds (904), (906), and (908) are labeled with molecular tags Pro10, Pro 11, and Pro 2, respectively. The total assay volume is 40 ul. The lysate volume is adjusted to 30 ul with lysis buffer. The antibodies are diluted in lysis buffer up to 5 ul. Typically ~5000 to 15000 cell-equivalent of lysates is used per reaction. The detection limit is ~1000 cell-equivalent of lysates. Procedure: Final concentrations of pre-mixed binding compounds (i.e. molecular tag- or biotin-antibody conjugates) in reaction:
Pro10_anti-Her-1: 0.05-0.1 ug/ml
Pro11_anti-Her-3: 0.1 ug/ml
Pro2_anti-phospho-Tyr: 0.1 to 0.2 ug/ml
Biotin_anti-Her-3: 1-2 ug/ml
1. To assay 96-well, add 5 ul antibody mix to 30 ul lysate and incubate for 1 hour at RT.
2. Add 5 ul streptavidin-derivatized cleaving probe (final 4 ug/well) to assay well and incubate for 45 min.
3. Add 150 ul of PBS with 1% BSA to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using an ABI3100 CE instrument with a 22 cm capillary (injection conditions: 5 kV, 70 sec, 30° C.; run conditions: 425 sec, 30° C.).

Assay Buffers are as Follows:
Lysis Buffer (Made Fresh and Stored on Ice)

| Final | ul | Stock |
|---|---|---|
| 1% Triton X-100 | 1000 | 10% |
| 20 mM Tris-HCl (pH 7.5) | 500 | 1 M |
| 100 mM NaCl | 200 | 5 M |
| 50 mM NaF | 500 | 1 M |
| 50 mM Na beta-glycerophosphate | 500 | 1.0 M |
| 1 mM $Na_3 VO_4$ | 100 | 0.1 M |
| 5 mM EDTA | 100 | 0.5 M |
| 10 ug/ml pepstatin | 100 | 1 mg/ml |
| 1 tablet (per 10 ml) Roche Complete protease inhibitor (#1836170) | N/A | N/A |
| Water | 7 ml | N/A |
|  | 10 ml | Total |

Wash buffer (stored at 4° C.): 0.5% Triton X100 in 1×PBS.
Illumination Buffer:

| Final | ul | Stock |
|---|---|---|
| 0.005x PBS | 50 | 1x |
| CE std 1 (A27, ACLARA Biosciences, Inc., Mountain View, CA) | 4 | 5000x |
| CE std 2 (fluorescein) | 4 | 5000x |
| Water | 9942 | N/A |
|  | 10 ml | Total |

Data Analysis:
1. Normalize relative fluorescence units (RFU) signal of each molecular tag against CE reference standard 2.
2. Subtract RFU of "no lysate" background control from corresponding molecular tag signals.
3. Report heterodimerization for Her-1 as the corresponding RFU ratiometric to RFU from Pro11_anti-Her-3 from assay wells using biotin-anti-Her-3.
4. Report receptor phosphorylation for Her-1,2,3 as RFU from Pro2_PT100 anti-phospho-Tyr ratiometric to RFU from Pro11_anti-Her-3 from assay wells using biotin-anti-Her-3 (data not shown).

Figure 9A:
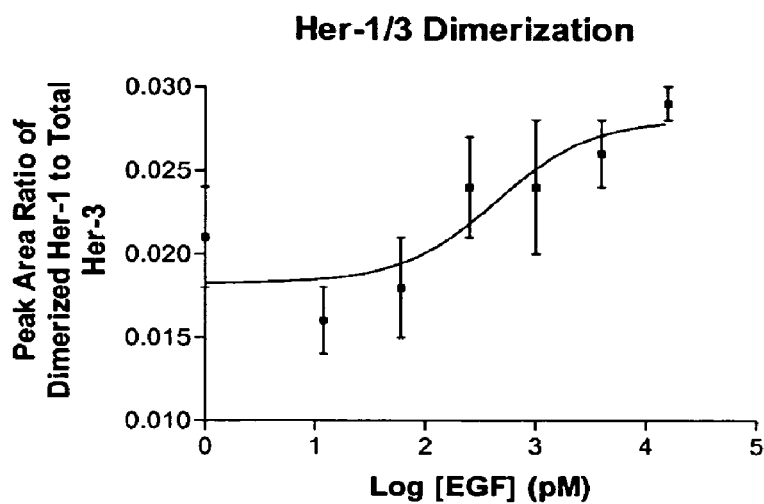
FIGS. 9A and 9B show data on the increases in the numbers of Her1-Her3 heterodimers on 22Rv1 and A549 cells, respectively, with increasing concentrations of epidermal growth factor (EGF).
Figure 9B:
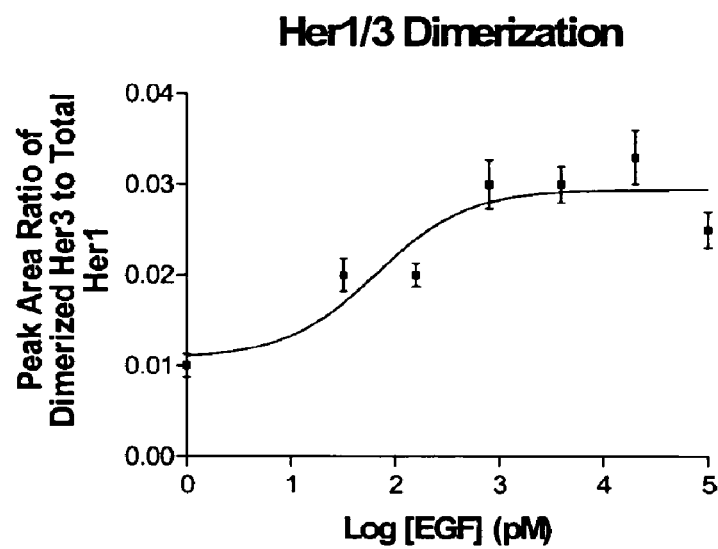

FIGS. 9A and 9B show the increases in the numbers of Her1-Her3 heterodimers on 22Rv1 and A549 cells, respectively, with increasing concentrations of EGF.

Example 7

Occurrence of IGF-1R Heterodimers with Her1, Her2, and Her3 in Breast Tumor Tissue Lysates In this example, cells from 12 different human breast tumor tissues were assayed for the presence of Her1-IGF-1R, Her2-IGF-1R, and Her3-IGF-1R dimers using assays essentially the same as that illustrated in FIG. 4A. Sample Preparation was carried out as follows:
1. Snap frozen tissues are mechanically disrupted at the frozen state by cutting.
2. Transfer tissues to microfuge tube and add 3× tissue volumes of lysis buffer followed by vortexing to disperse tissues in buffer.
3. Incubate on ice for 30 min with intermittent vortexing to mix.
4. Centrifuge at 14,000 rpm, 4° C., for 20 min.
5. Collect supernatants as lysates and determine total protein concentration with BCA assay (Pierce) using a small aliquot.
6. Aliquot the rest for storage at −80° C. until use.

The assay was set up as follows.
1. The total assay volume is 40 ul.
2. The lysates are tested in serial titration series of 40, 20, 10, 5, 2.5, 1.25, 0.63, 0.31 ug total-equivalents and the volume is adjusted to 30 ul with lysis buffer. Data from the titration series confirm the specificity of the dimerization.
3. A universal antibody mix comprising of all binding compounds and biotin antibody diluted in lysis buffer is used at concentrations given below.

Final Concentrations of Pre-Mixed Antibodies in Reactions:
Pro10_anti-Her-2: 0.1 ug/ml
Pro14_anti-Her-1: 0.1 ug/ml
Pro11_anti-Her-3: 0.1 ug/ml
Pro7_anti-IGF-1R: 0.1 ug/ml
Pro2_anti-phospho-Tyr: 0.2 ug/ml
Biotin_anti-Her-2: 2 ug/ml Procedure:
1. To assay 96-wells, add 5 ul universal reaction mix to 30 ul lysate and incubate for 1 hour at RT.
2. Add 5 ul strepatvidin-derivatized molecular scissor (final 4 ug/well) to assay well and 5 incubate for 45 min.
3. Add 150 ul of PBS with 1% BSA to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using: (i) CE equipment: ABI3100, 22 cm capillary, (ii) CE injection conditions: 5 kV, 70 sec, 30° C., and (iii) CE run conditions: 425 sec, 30° C.

Data Analysis:
1. Normalize RFU signal of each molecular tag against CE reference standard 1.
2. Look for titratable signals for each molecular tag. Signals that do not titrate are assumed to be non-specific signals and are not used for data interpretation. A cut off value is determined based on the values from a large set of normal tissues where dimerization signals are expected to be absent or at the lowest. These values also represent the basal level of dimerization on the normal tissues to which tumor tissues are compared.
3. Heterodimerization is reported for IGF-1R with Her-1 or Her-2 or Her-3 as the corresponding specific RFU.

Figure 10A:
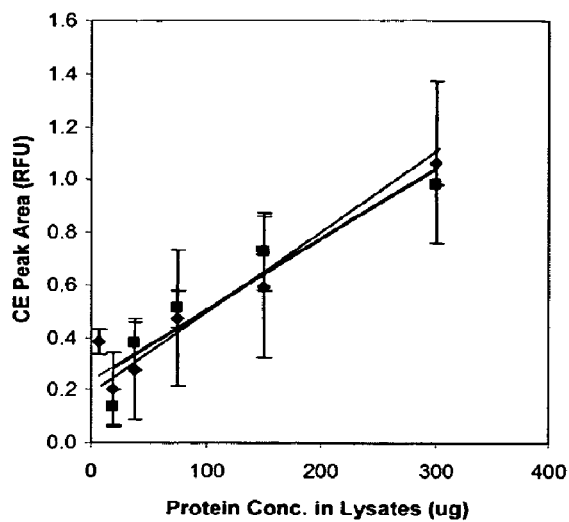
FIGS. 10A-10C show data on the expression of heterodimers of IGF-1R and various Her receptors in frozen samples from human breast tissue.
Figure 10B:
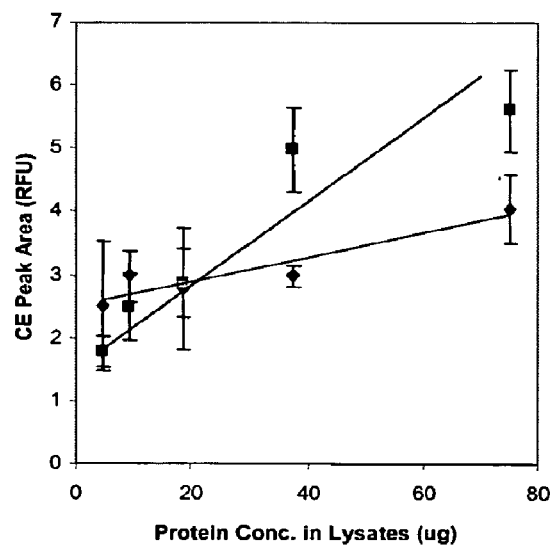
Figure 10C:
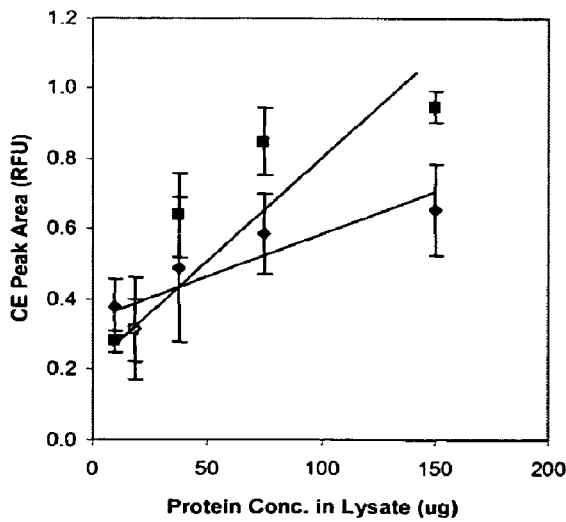

Two out of the twelve breast tumors assayed expressed Her1-IGF-1R, Her2-IGF-1R, and Her3-IGF-1R heterodimers, as shown in FIGS. 10A-C. The lines in each figure panel shows the trend between receptor heterodimer quantity measured and amount of lysate assayed for the two breast tumor samples that were positive for the indicated heterodimers.

Example 8

Measurement of Receptor Dimers in Formalin Fixed Paraffin Embedded Tissue Samples In this example, model fixed tissues made from pelleted cell lines were assayed for the presence of Her receptor dimers. The assay design for heterodimers was essentially the same as that described in FIG. 4A, with exceptions as noted below. That is, four components are employed: (i) a cleaving probe comprising a biotinylated monoclonal antibody conjugated to a cleavage-inducing moiety (in this example, a photosensitizer-derivatized streptavidin, as illustrated in FIG. 3E) and specific for one of the receptors of the dimer, (ii) a monoclonal antibody derivatized with a first molecular tag and specific for the same receptor as the cleaving probe, (iii) a monoclonal antibody derivatized with a second molecular tag and specific for the receptor opposite to that the cleaving probe is specific for, and (iv) a monoclonal antibody derivatized with a third molecular tag and specific for an intracellular phosphorylated tyrosine. The assay design for homodimers was essentially the same as that described in FIG. 1D, with exceptions as noted below.

In each case, model fixed tissues were prepared as follows: cells grown on tissue culture plates were stimulated with either EGF or HRG as described in the prior examples, after which they were washed and removed by scrapping. The removed cells were centrifuged to form a pellet, after which formalin was added and the mixture was incubated overnight at 4° C. The fixed pellet was embedded in paraffin using a Miles Tissue Tek III Embedding Center, after which 10 μm tissue sections were sliced from the pellet using a microtome (Leica model 2145). Tissue sections were placed on positively charged glass microscope slides (usually multiple tissue sections per slide) and baked for 1 hr at 60° C.

Tissue sections on the slides were assayed as follows: Tissue sections on a slide were de-waxed with EZ-Dewax reagent (Biogenex, San Ramon, Calif.) using the manufacturer's recommended protocol. Briefly, 500 μL EZ-Dewax was added to each tissue section and the sections were incubated at RT for 5 min, after which the slide was washed with 70% EtOH. This step was repeated and the slide was finally rinsed with deionized water, after which the slide was incubated in water at RT for 20 min. The slide was then immersed into a 1× Antigen Retrieval solution (Biogenesis, Brentwood, N.H.) at pH 10, after which it was heated for 15 min in a microwave oven (5 min at high power setting followed by 10 min at a low power setting). After cooling to RT (about 45 min), the slide was placed in a water bath for 5 min, then dried. Tissue sections on the dried slide were circled with a hydrophobic wax pen to create regions capable of containing reagents placed on the tissue sections (as illustrated in FIGS. 3H-3I), after which the slide was washed three times in 1× Perm/Wash (BD Biosciences). To each section 50-100 µL blocking buffer was added, and the slide was placed in a covered humidified box containing deionized water for 2 hr at 4° C., after which the blocking buffer was removed from each section by suction. (Blocking buffer is 1× Perm/Wash solution with protease inhibitors (Roche), phosphatase inhibitors (sodium floride, sodium vanadate, β-glycerol phosphate), and 10% mouse serum). To each section 40-50 µL of antibody mix containing binding compounds and cleaving probe was added (each at 5 µg/mL, except that biotin-Ab5 (anti-Her1) was at 10 µg/mL in the Her1-Her2 assay), and the slide was placed in a humidified box overnight at 4° C. The sections were then washed three times with 100 µL Perm/Wash containing protease and phosphatase inhibitors, after which 50 µL of photosensitizer in 1× Perm/Wash solution (containing protease and phosphatase inhibitors) was added. The slide was then incubated for 1-1.5 hr at 4° C. in the dark in a humidified box, after which the photosensitizer was removed by suction while keeping the slide in the dark. While remaining in the dark, the slide was then immersed in 0.01×PBS and incubated on ice for 1 hr. The slide was remove from the PBS, dried, and to each section, 40-50 µL 0.01×PBS with 2 pM fluorescein was added, after which it was illuminated with a high power laser diode (GaAIAs IR emitter, model OD-880W, OPTO DIODE CORP, Newbury Park, Calif.) for 1 hr. The fluorescein acts as a standard to assist in correlating peaks in an electropherogram with molecular tags. After illumination, the solution covering each tissue section was mixed by gentle pipeting and transferred to a CE plate for analysis on an Applied Biosystems (Foster City, Calif.) model 3100 capillary electrophoresis instrument.

Figure 11A:
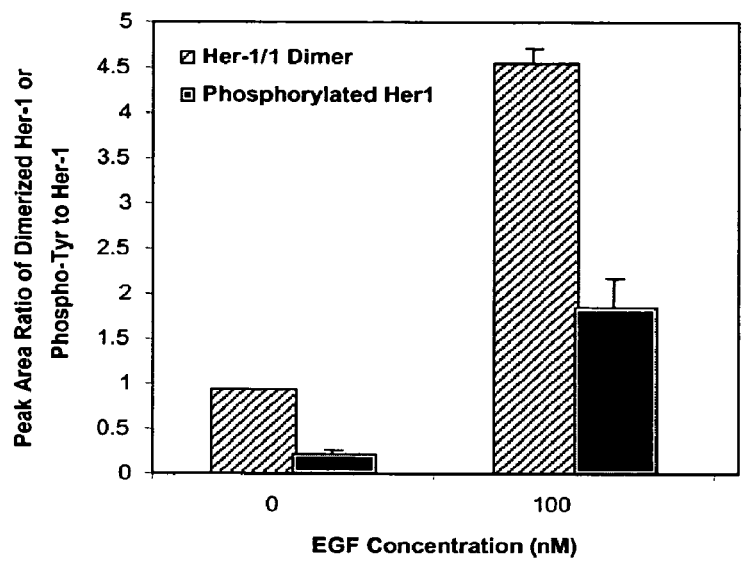
FIGS. 11A-11G illustrate the assay design and experimental results for detecting a PI3 kinase-Her3 receptor activation complex.

FIG. 11A shows data from analysis of Her1-Her1 homodimers and receptor phosphorylation in sections from fixed pellets of breast adenocarcinoma cell line, MDA-MB-468 (ATCC accession no. HTB-132), prepared from either non-stimulated cells or cells stimulated with 100 nM EGF. Biotinylated anti-Her1 monoclonal antibody (Labvision) at 2 µg/mL was use as the primary antibody of the cleaving probe (for cleavage methylene-blue derivatized streptavidin (described above) was attached through the biotin). Pro10-derivatized anti-Her1 monoclonal antibody (Labvision) at 2 µg/mL was used to measure homodimerized Her1. Pro1-derivatized anti-Her1 monoclonal antibody (Labvision) at 0.8 µg/mL was used to measure total Her1. Unlabeled antibody Ab-5 was also included in the reactions at 3.2 µg/mL. Pro2-derivatized monoclonal antibody (anti-phosphorylated-Tyr, Cell Signaling) at 0.5 µg/mL was used to measure intracellular phosphorylation. The data from fixed tissue measurements confirm and are consistent with measurements on cell lysates that show increases in Her1-Her1 homodimer expression and intracellular phosphoryation due to EGF stimulation.

Figure 11B:
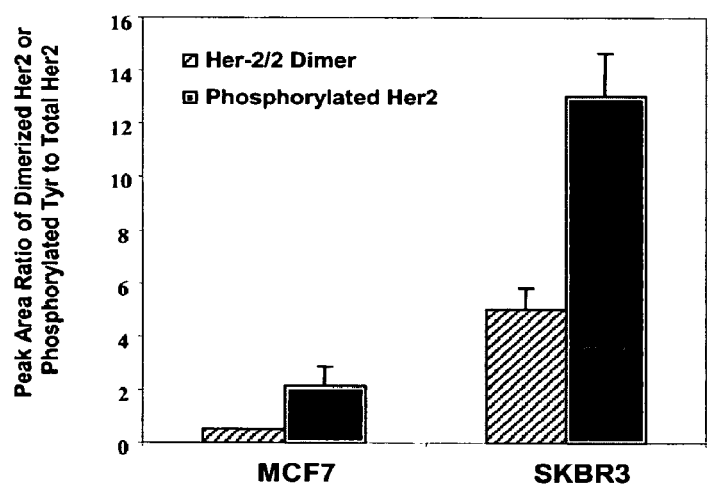

FIG. 11B shows data from analysis of Her2-Her2 homodimers and receptor phosphorylation in sections from fixed pellets of breast cancer cell lines MCF-7 and SKBR-3. All monoclonal antibodies used as cleaving probes or binding compounds were used at concentrations of 5 µg/mL. In order to generate better cleavage, in this assay two cleaving probes were employed, one directed to an extracellular antigenic determinant of Her2 and one directed to an intracellular antigenic determinant of Her2. The data from fixed tissue measurements confirm that SKBR3 cells express higher levels of Her2-Her2 homodimers than MCF-7 cells.

Figure 11C:
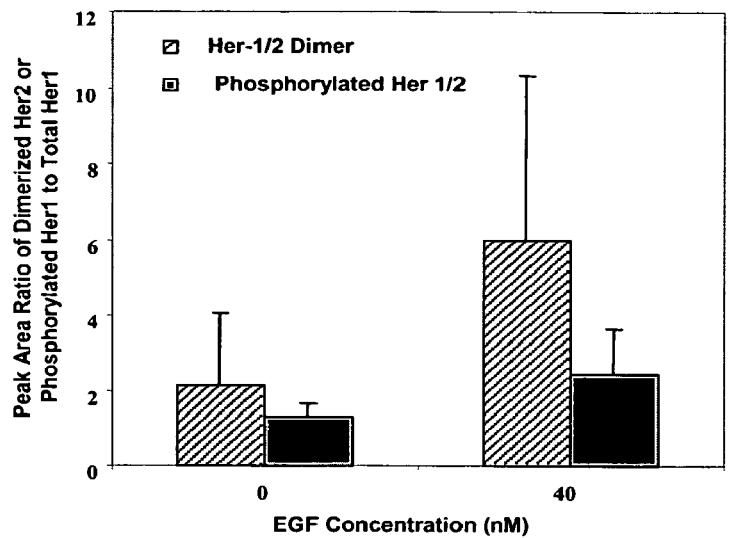

FIG. 11C shows data from analysis of Her1-Her2 heterodimers and receptor phosphorylation in sections from fixed pellets of breast adenocarcinoma cell line, MCF-7, prepared from either non-stimulated cells or cells stimulated with 40 nM EGF. Two cleaving probes were employed one comprising anti-Her1 monoclonal antibody (at 5 µg/mL) and the other comprising anti-Her1 monoclonal antibody (at 10 µg/mL) (both from Labvision) in order to increase the rate at which molecular tags were released. The data show that increases in Her1-Her2 heterodimer expression due to EGF stimulation is detected in fixed tissue.

Figure 11D:
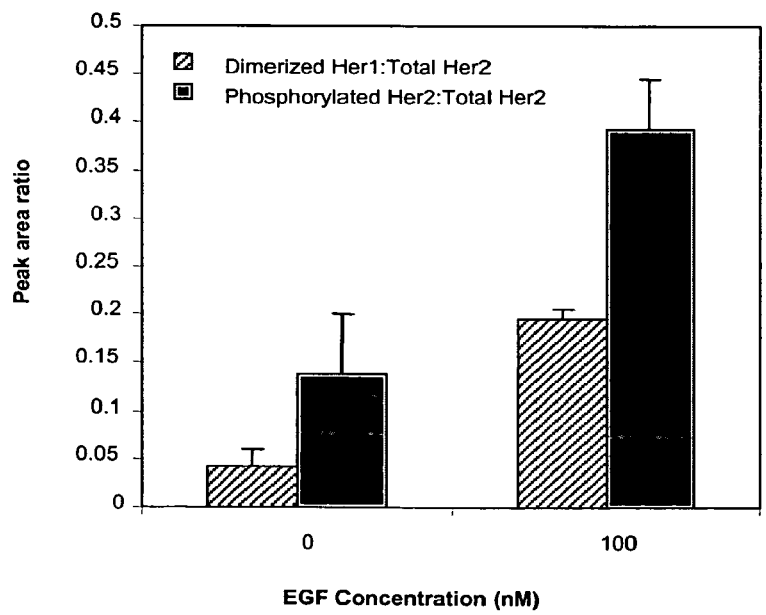

FIG. 11D shows data from analysis of Her1-Her2 heterodimers and receptor phosphorylation in sections from fixed pellets of breast adenocarcinoma cell line, 22Rv1, prepared from either non-stimulated cells or cells stimulated with 100 nM EGF. Again, measurements on fixed tissues demonstrates the up-regulation of Her1-Her2 dimers and Her receptor phosphorylation in response to treatment with EGF.

Figure 11E:
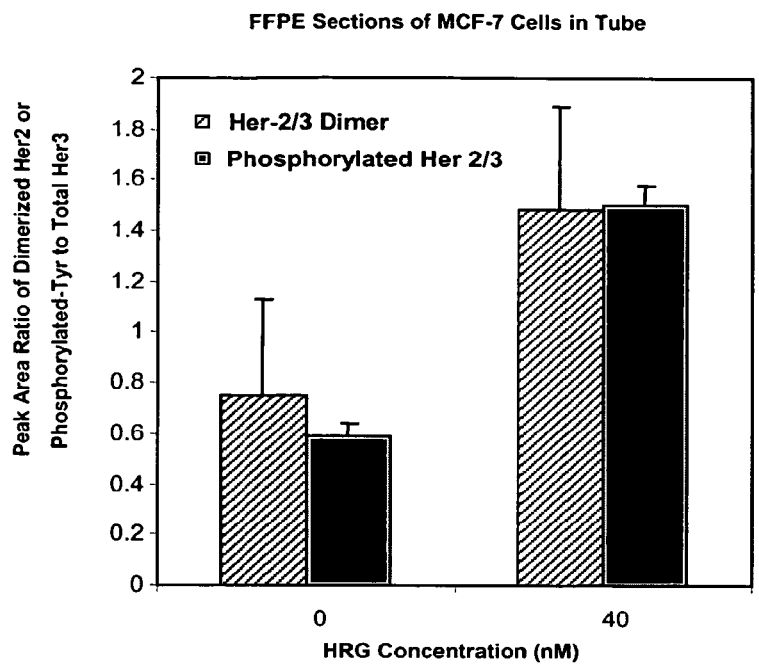

FIG. 11E shows data from analysis of Her2-Her3 heterodimers and receptor phosphorylation in sections from fixed pellets of breast adenocarcinoma cell line, MCF-7, prepared from either non-stimulated cells or cells stimulated with 40 nM HRG. In this example, binding reactions and cleavage reactions took place in tubes containing sections, rather than microscope slides. Otherwise, the protocol was essentially the same as that for detecting the Her1-Her2 dimers. (For example, washing steps are carried out by centrifugation). The data show that increases in Her2-Her3 heterodimer expression due to HRG stimulation is detected in fixed tissue.

Figure 11F:
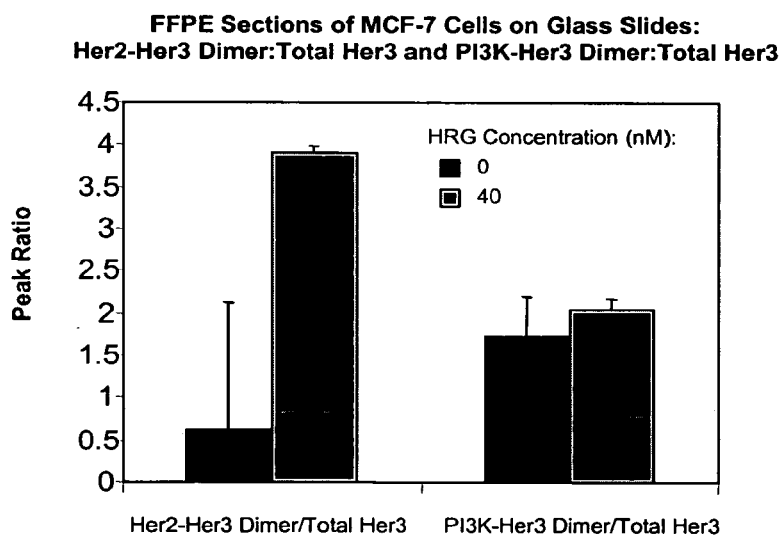

FIG. 11F shows data from analysis of Her2-Her3 heterodimers and PI3K-Her3 dimers in sections from fixed pellets of MCF-7 cells either non-stimulated or stimulated with 40 nM HRG. The assay design for PI3K-Her3 was essentially as described in FIG. 11A. The above fixation protocol was followed in both cases, except that neither sample was treated with antigen retrieval reagents. The data show that Her2-Her3 dimers increased with treatment by HRG, but that the amount of PI3K-Her3 dimer remained essentially unchanged.

Figure 11G:
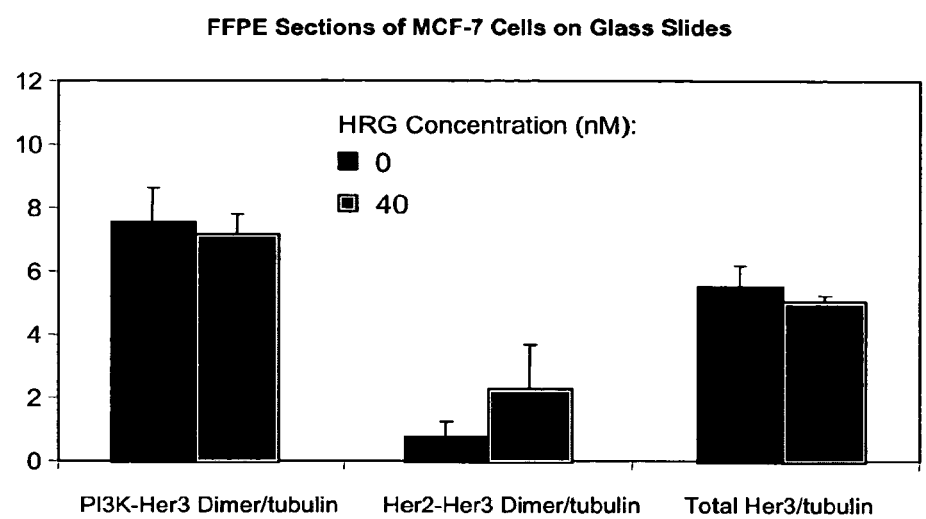

FIG. 11G shows data from analysis of total PI3K, total Her2-Her3 dimer, and total Her3 all relative to amount of tubulin. Tubulin was measured in a conventional sandwich-type assay employing a cleavage probe and a binding compound with a molecular tag. Tubulin was measured to test procedures for normalizing dimer measurement against a target representative of total cell number in a sample, which may be required for measurements on samples with heterogeneous cell types. The data show that the ratios of PI3K-Her3 and Her2-Her3 to tubulin are qualitatively the same as the measurements directly on PI3K-Her3 and Her2-Her3.

What is claimed is:

1. A method of detecting a homodimer comprising a dimer of a membrane-associated analyte on a cell membrane, the method comprising the steps of:
   (a) providing a first binding compound specific for a first antigenic determinant of the membrane-associated analyte, wherein the first binding compound has a first molecular tag attached thereto by a cleavable linkage, and wherein the first molecular tag has a first separation characteristic;

(b) providing a second binding compound specific for a second antigenic determinant of the membrane-associated analyte, wherein the second binding compound has a second molecular tag attached thereto by a cleavable linkage, and wherein the second molecular tag has a second separation characteristic that is different than the first separation characteristic of the first molecular tag of the first binding compound;

(c) providing a cleaving probe specific for the first antigenic determinant of the membrane-associated analyte, wherein:

(i) the cleaving probe has a cleavage-inducing moiety with an effective proximity to the cleavable linkage of the first binding compound when the cleaving probe and the first binding compound are each bound to one first antigenic determinant of membrane-associated analyte in the homodimer, (ii) the cleavage probe has a cleavage-inducing moiety with an effective proximity to the cleavable linkage of the second binding compound when the cleaving probe is bound to the first antigenic determinant of the membrane-associated analyte and the second binding compound is bound to the second antigenic determinant of either the same membrane-associated analyte or the other membrane-associated analyte in the homodimer, and (iii) only one of either the cleaving probe or the first binding composition can specifically bind to the first antigenic determinant of one membrane-associated analyte;

(d) mixing the cleaving probe, the first binding compound, the second binding compound, and the cell membrane such that (i) if a homodimer is present, the cleaving probe and the first binding compound each specifically bind to one first antigenic determinant of the membrane-associated analyte in the homodimer and the first molecular tag is released;

(ii) if a homodimer is present, the cleaving probe binds to the first antigenic determinant of one of the membrane associated analytes in the homodimer and the second binding compound binds to the second antigenic determinant of each membrane associated analytes in the homodimer, and the second molecular tag is released from the second binding compounds; and (iii) if a monomer is present, the cleaving probe binds to the first antigenic determinant of the membrane associated analyte and the second binding compound binds to the second antigenic determinant of the membrane associated analyte, and the second molecular tag is released; and (e) separating and detecting the released molecular tags to determine the presence or the amount of homodimer in the cell membrane.

2. The method of claim 1, wherein the membrane-associated analyte is a cell surface receptor.

3. The method of claim 1, wherein the first and second separation characteristics of the first and second molecular tags are electrophoretic mobilities.

4. The method according to claim 1, wherein the membrane-associated analyte is selected from the group consisting of epidermal growth factor receptors and G-protein coupled receptors.

5. The method of claim 1, wherein said membrane-associated analyte is selected from the group consisting of Her1, Her2, Her3, and Her4.

6. The method of claim 1, wherein the cleaving probe, the first binding compound, and the second binding compound each comprise an antibody binding composition.

7. The method of claim 1, wherein the homodimer complex comprises a Her1 homodimer or a Her2 homodimer.

8. The method of claim 3, wherein the step of separating and detecting the molecular tags comprises electrophoretically separating the released first and second molecular tags to form distinct peaks in an electropherogram.

9. The method of claim 1, wherein the first binding compound is specific for a phosphorylation site of the membrane-associated analyte.

10. The method of claim 1, wherein the second binding compound is specific for a phosphorylation site of the membrane-associated analyte.

11. The method of claim 1, further comprising determining the total amount of membrane-associated analyte in the cell membrane.

12. The method of claim 1, further comprising determining the ratio of the homodimer to total membrane-associated analyte in the cell membrane.

13. The method of claim 1, further comprising providing a third binding composition is specific for a third antigenic determinant, wherein the third antigenic determinant is a post-translational modification of the membrane-associated analyte.

14. The method of claim 13, wherein the post-translational modification is a phosphorylation site.

* * * * *